(12) United States Patent
Renz et al.

(10) Patent No.: US 7,579,517 B2
(45) Date of Patent: Aug. 25, 2009

(54) METHODS FOR INCREASING OIL CONTENT IN PLANTS

(75) Inventors: Andreas Renz, Limburgerhof (DE); Jörg Bauer, Ludwigshafen (DE); Marc Stitt Nigel, Potsdam (DE); Rita Maria Zrenner, Golm (DE); Peter Geigenberger, Berlin (DE); Helene Vigeolas, Potsdam (DE)

(73) Assignee: BASF Plant Science GmbH (DE)

( * ) Notice: Subject to any disclaimer, the term of this patent is extended or adjusted under 35 U.S.C. 154(b) by 834 days.

(21) Appl. No.: 10/513,412

(22) PCT Filed: May 6, 2003

(86) PCT No.: PCT/EP03/04711

§ 371 (c)(1),
(2), (4) Date: Nov. 4, 2004

(87) PCT Pub. No.: WO03/095655

PCT Pub. Date: Nov. 20, 2003

(65) Prior Publication Data

US 2006/0168684 A1 Jul. 27, 2006

(30) Foreign Application Priority Data

May 8, 2002 (DE) ................. 102 20 753
Jun. 13, 2002 (DE) ................. 102 26 413

(51) Int. Cl.
*C12N 15/82* (2006.01)
*A01H 5/00* (2006.01)

(52) U.S. Cl. ..................... 800/281; 800/298; 435/320.1

(58) Field of Classification Search ....................... None
See application file for complete search history.

(56) References Cited

U.S. PATENT DOCUMENTS 6,103,520 A 8/2000 Topfer et al.

FOREIGN PATENT DOCUMENTS

| EP | 0 353 049 | | 1/1990 |
| WO | WO 93/07275 | | 4/1993 |
| WO | WO 9821339 A1 | * | 5/1998 |
| WO | WO 01/21820 A1 | | 3/2001 |

OTHER PUBLICATIONS

Eriksson, Peter, et al., "Cloning and Characterization of *GPD2*, a Second Gene Encoding *sn*-Glycerol 3-Phosphate Dehydrogenase (NAD$_+$) in *Saccharomyces cerevisiae*, and its Comparison with *GPD1*," *Molecular Microbiology*, 17(1):95-107 (1995).
Wang, Hwa-Tang, et al., "Cloning, Sequence, and Disruption of the *Saccharomyces diastaticus DAR1* Gene Enconding a Glycerol-3-Phosphate Dehydrogenase," *Journal of Bacteriology*, 176(22):7091-7095 (1994).
Merkel, Joseph R., et al., "Purification and Some Properties of *sn*-Glycerol-3-Phosphate Dehydrogenase from *Saccharomyces cerevisiae*," *Analytical Biochemistry*, 122:180-185 (1982).
Albertyn, Jacobus, et al., "Purification and Characterization of Glycerol-3-Phosphate Dehydrogenase of *Saccharomyces cerevisiae*," *FEBS Letters*, 308(2):130-132 (1992).
Albertyn, Jacobus, et al., "*GPD1*, Which Encodes Glycerol-3-Phosphate Dehydrogenase, is Essential for Growth Under Osmotic Stress in *Saccharomyces cerevisiae*, and its Expression is Regulated by the High-Osmolarity Glycerol Response Pathway," *Molecular and Cellular Biology*, 14(6):4135-4144 (1994).
Iwaki, Tomoko, et al., "Cloning of Glycerol-3-Phosphate Dehydrogenase Genes (*ZrGPD1* and *ZrGPD2*) and Glycerol Dehydrogenase Genes (*ZrGCY1* and *ZrGCY2*) from the Salt-Tolerant Yeast *Zygosaccharomyces rouxii*," *Yeast*, 18:737-744 (2001).
Ohmiya, Ryusuke, et al., "Osmoregulation of Fission Yeast: Cloning of Two Distinct Genes Encoding Glycerol-3-Phosphate Dehydrogenase, One of which is Responsible for Osmotolerance for Growth," *Molecular Microbiology*, 18(5):963-973 (1995).
Pidoux, Alison L., et al., "Glycerol-3-Phosphate Dehydrogenase Homologue from *Schizosaccharomyces pombe*," *Nucleic Acids Research*, 18(23):7145 (1990).
Bell, Robert M., "Mutants of *Escherichia coli* Defective in Membrane Phospholipid Synthesis: Macromolecular Synthesis in an sn-Glycerol 3-Phosphate Acyltransferase $K_m$ Mutant," *Journal of Bacteriology*, 117(3):1065-1076 (1974).
Hsu, Chuen Chin, et al., "Induction of the Lactose Transport System in a Lipid-Synthesis-Defective Mutant of *Escherichia coli*," *Journal of Bacteriology*, 103(2):410-416 (1970).
Gee, Robert, et al., "Two Isozymes of Dihydroxyacetone Phosphate Reductase in *Dunaliella*," *Plant Physiol.*, 91:345-351 (1989).
Gee, Robert, et al., "Two Isoforms of Dihydroxyacetone Phosphate Reductase from the Chloroplasts of *Dunaliella tertiolecta*," *Plant Physiol.*, 103:243-249 (1993).
Gee, Robert W., et al., "Dihydroxyacetone Phosphate Reductase in Plants," *Plant Physiol.*, 86:98-103 (1988).
Santora, George T., et al., "Isolation of a *sn*-Glycerol 3-Phosphate: NAD Oxidoreductase from Spinach Leaves," *Archives of Biochemistry and Biophysics*, 196(2):403-411 (1979).
Gee, Robert W., et al., "Differential Inhibition and Activation of Two Leaf Dihydroxyacetone Phosphate Reductases," *Plant Physiol.* ,87:379-383 (1988).
Miyata, Keijiro, et al., "Some Properties of NAD-Independent α-Glycerophosphate Dehydrogenase of Yeast," *Plant & Cell Physiol.*, 10:635-643 (1969).

(Continued)

*Primary Examiner*—Elizabeth F McElwain
(74) *Attorney, Agent, or Firm*—Connolly Bove Lodge & Hutz LLP

(57) ABSTRACT

The invention relates to methods for increasing the oil content in plants, preferably in the seeds of plants, by expression of glycerol-3-phosphatdehydrogenases (G3PDH) from yeast, preferably from *Saccharomyces cerevisiae*. The invention also relates to expression constructs for the expression of G3PDH yeast in plants, preferably in the seeds of plants, transgenic plants expressing G3PDH, and to the use of said transgenic plants in the production of foodstuffs, feed, seeds, pharmaceuticals or fine chemicals, especially in the production of oils.

26 Claims, 3 Drawing Sheets

OTHER PUBLICATIONS

Larsson, Christer, et al., "The Importance of the Glycerol 3-Phosphate Shuttle During Aerobic Growth of *Saccharomyces cerevisiae*," *Yeast*, 14:347-357 (1998).

Frentzen, Margrit, "Acyltransferases from Basic Science to Modified Seed Oils," *Lipids*, 100(4-5):161-166 (1998).

Shanklin, John, et al., "Desaturation and Related Modifications of Fatty Acids," *Ann. Rev. Plant Mol. Biol.*, 49:611-641 (1998).

Voelker, Toni, "Plant Acyl-ACP Thioesterases: Chain-Length Determining Enzymes in Plant Fatty Acid Biosynthesis," *Genetic Engineering*, 18:111-132 (1996).

Ohlrogge, John, et al., "Lipid Biosynthesis," *The Plant Cell*, 7:957-970 (1995).

Browse, John, et al., "Fluxes Through the Prokaryotic and Eukaryotic Pathways of Lipid Synthesis in the '16:3' Plant *Arabidopsis thaliana*," *Biochemical J.*, 235:25-31 (1986).

Millar Anthony A., et al., "All Fatty Acids are Not Equal: Discrimination in Plant Membrane Lipids," *Trends in Plant Science*, 5(3):95-101 (2000).

Topfer, Reinhard, et al., "Modification of Plant Lipid Synthesis," *Science*, 268:681-686 (1995).

Thelen, Jay J., et al., "Metabolic Engineering of Fatty Acid Biosynthesis in Plants," *Metabolic Engineering*, 4:12-21 (2002).

GeneBank Accession No. AF210060, last updated Jan. 22, 2004.
GeneBank Accession No. AF228340, last updated Feb. 4, 2001.
GeneBank Accession No. Z35169, last updated Mar. 5, 1996.
GeneBank Accession No. U04621, last updated Mar. 4, 2000.
GeneBank Accession No. X76859, last updated Jun. 28, 1994.
GeneBank Accession No. AB047397, last updated Jan. 12, 2002.
GeneBank Accession No. AB047395, last updated Jan. 12, 2002.
GeneBank Accession No. AB047394, last updated Jan. 12, 2002.
GeneBank Accession No. AJ250328, last updated Oct. 15, 1999.
GeneBank Accession No. D50797, last updated Oct. 3, 1997.
GeneBank Accession No. D50796, last updated Jan. 21, 1999.
GeneBank Accession No. X56162, last updated Dec. 11, 1990.

* cited by examiner

SEQUENCE LISTING

<160> NUMBER OF SEQ ID NOS: 40

<210> SEQ ID NO 1
<211> LENGTH: 1176
<212> TYPE: DNA
<213> ORGANISM: Saccharomyces cerevisiae
<220> FEATURE:
<221> NAME/KEY: CDS
<222> LOCATION: (1)..(1173)
<223> OTHER INFORMATION: coding for G3PDH

<400> SEQUENCE: 1

```
atg tct gct gct gct gat aga tta aac tta act tcc ggc cac ttg aat      48
Met Ser Ala Ala Ala Asp Arg Leu Asn Leu Thr Ser Gly His Leu Asn
 1               5                  10                  15 gct ggt aga aag aga agt tcc tct tct gtt tct ttg aag gct gcc gaa      96
Ala Gly Arg Lys Arg Ser Ser Ser Ser Val Ser Leu Lys Ala Ala Glu
             20                  25                  30 aag cct ttc aag gtt act gtg att gga tct ggt aac tgg ggt act act     144
Lys Pro Phe Lys Val Thr Val Ile Gly Ser Gly Asn Trp Gly Thr Thr
         35                  40                  45 att gcc aag gtg gtt gcc gaa aat tgt aag gga tac cca gaa gtt ttc     192
Ile Ala Lys Val Val Ala Glu Asn Cys Lys Gly Tyr Pro Glu Val Phe
 50                  55                  60 gct cca ata gta caa atg tgg gtg ttc gaa gaa gag atc aat ggt gaa     240
Ala Pro Ile Val Gln Met Trp Val Phe Glu Glu Glu Ile Asn Gly Glu
 65                  70                  75                  80 aaa ttg act gaa atc ata aat act aga cat caa aac gtg aaa tac ttg     288
Lys Leu Thr Glu Ile Ile Asn Thr Arg His Gln Asn Val Lys Tyr Leu
                 85                  90                  95 cct ggc atc act cta ccc gac aat ttg gtt gct aat cca gac ttg att     336
Pro Gly Ile Thr Leu Pro Asp Asn Leu Val Ala Asn Pro Asp Leu Ile
            100                 105                 110 gat tca gtc aag gat gtc gac atc atc gtt ttc aac att cca cat caa     384
Asp Ser Val Lys Asp Val Asp Ile Ile Val Phe Asn Ile Pro His Gln
        115                 120                 125 ttt ttg ccc cgt atc tgt agc caa ttg aaa ggt cat gtt gat tca cac     432
Phe Leu Pro Arg Ile Cys Ser Gln Leu Lys Gly His Val Asp Ser His
    130                 135                 140 gtc aga gct atc tcc tgt cta aag ggt ttt gaa gtt ggt gct aaa ggt     480
Val Arg Ala Ile Ser Cys Leu Lys Gly Phe Glu Val Gly Ala Lys Gly
145                 150                 155                 160 gtc caa ttg cta tcc tct tac atc act gag gaa cta ggt att caa tgt     528
Val Gln Leu Leu Ser Ser Tyr Ile Thr Glu Glu Leu Gly Ile Gln Cys
                165                 170                 175 ggt gct cta tct ggt gct aac att gcc acc gaa gtc gct caa gaa cac     576
Gly Ala Leu Ser Gly Ala Asn Ile Ala Thr Glu Val Ala Gln Glu His
            180                 185                 190 tgg tct gaa aca aca gtt gct tac cac att cca aag gat ttc aga ggc     624
Trp Ser Glu Thr Thr Val Ala Tyr His Ile Pro Lys Asp Phe Arg Gly
        195                 200                 205 gag ggc aag gac gtc gac cat aag gtt cta aag gcc ttg ttc cac aga     672
Glu Gly Lys Asp Val Asp His Lys Val Leu Lys Ala Leu Phe His Arg
    210                 215                 220 cct tac ttc cac gtt agt gtc atc gaa gat gtt gct ggt atc tcc atc     720
Pro Tyr Phe His Val Ser Val Ile Glu Asp Val Ala Gly Ile Ser Ile
225                 230                 235                 240 tgt ggt gct ttg aag aac gtt gtt gcc tta ggt tgt ggt ttc gtc gaa     768
Cys Gly Ala Leu Lys Asn Val Val Ala Leu Gly Cys Gly Phe Val Glu
                245                 250                 255 ggt cta ggc tgg ggt aac aac gct tct gct gcc atc caa aga gtc ggt     816
Gly Leu Gly Trp Gly Asn Asn Ala Ser Ala Ala Ile Gln Arg Val Gly
            260                 265                 270 ttg ggt gag atc atc aga ttc ggt caa atg ttt ttc cca gaa tct aga     864
Leu Gly Glu Ile Ile Arg Phe Gly Gln Met Phe Phe Pro Glu Ser Arg
        275                 280                 285 gaa gaa aca tac tac caa gag tct gct ggt gtt gct gat ttg atc acc     912
Glu Glu Thr Tyr Tyr Gln Glu Ser Ala Gly Val Ala Asp Leu Ile Thr
    290                 295                 300 acc tgc gct ggt ggt aga aac gtc aag gtt gct agg cta atg gct act     960
Thr Cys Ala Gly Gly Arg Asn Val Lys Val Ala Arg Leu Met Ala Thr
```

```
Thr Cys Ala Gly Gly Arg Asn Val Lys Val Ala Arg Leu Met Ala Thr
305                 310                 315                 320 tct ggt aag gac gcc tgg gaa tgt gaa aag gag ttg ttg aat ggc caa      1008
Ser Gly Lys Asp Ala Trp Glu Cys Glu Lys Glu Leu Leu Asn Gly Gln
            325                 330                 335 tcc gct caa ggt tta att acc tgc aaa gaa gtt cac gaa tgg ttg gaa      1056
Ser Ala Gln Gly Leu Ile Thr Cys Lys Glu Val His Glu Trp Leu Glu
        340                 345                 350 aca tgt ggc tct gtc gaa gac ttc cca tta ttt gaa gcc gta tac caa      1104
Thr Cys Gly Ser Val Glu Asp Phe Pro Leu Phe Glu Ala Val Tyr Gln
    355                 360                 365 atc gtt tac aac aac tac cca atg aag aac ctg ccg gac atg att gaa      1152
Ile Val Tyr Asn Asn Tyr Pro Met Lys Asn Leu Pro Asp Met Ile Glu
370                 375                 380 gaa tta gat cta cat gaa gat tag                                      1176
Glu Leu Asp Leu His Glu Asp
385                 390
```

<210> SEQ ID NO 2
<211> LENGTH: 391
<212> TYPE: PRT
<213> ORGANISM: Saccharomyces cerevisiae

<400> SEQUENCE: 2

```
Met Ser Ala Ala Ala Asp Arg Leu Asn Leu Thr Ser Gly His Leu Asn
1               5                   10                  15

Ala Gly Arg Lys Arg Ser Ser Ser Val Ser Leu Lys Ala Ala Glu
            20                  25                  30

Lys Pro Phe Lys Val Thr Val Ile Gly Ser Gly Asn Trp Gly Thr Thr
        35                  40                  45

Ile Ala Lys Val Val Ala Glu Asn Cys Lys Gly Tyr Pro Glu Val Phe
    50                  55                  60

Ala Pro Ile Val Gln Met Trp Val Phe Glu Glu Ile Asn Gly Glu
65                  70                  75                  80

Lys Leu Thr Glu Ile Ile Asn Thr Arg His Gln Asn Val Lys Tyr Leu
                85                  90                  95

Pro Gly Ile Thr Leu Pro Asp Asn Leu Val Ala Asn Pro Asp Leu Ile
            100                 105                 110

Asp Ser Val Lys Asp Val Asp Ile Ile Val Phe Asn Ile Pro His Gln
        115                 120                 125

Phe Leu Pro Arg Ile Cys Ser Gln Leu Lys Gly His Val Asp Ser His
    130                 135                 140

Val Arg Ala Ile Ser Cys Leu Lys Gly Phe Glu Val Gly Ala Lys Gly
145                 150                 155                 160

Val Gln Leu Leu Ser Ser Tyr Ile Thr Glu Glu Leu Gly Ile Gln Cys
                165                 170                 175

Gly Ala Leu Ser Gly Ala Asn Ile Ala Thr Glu Val Ala Gln Glu His
            180                 185                 190

Trp Ser Glu Thr Thr Val Ala Tyr His Ile Pro Lys Asp Phe Arg Gly
        195                 200                 205

Glu Gly Lys Asp Val Asp His Lys Val Leu Lys Ala Leu Phe His Arg
    210                 215                 220

Pro Tyr Phe His Val Ser Val Ile Glu Asp Val Ala Gly Ile Ser Ile
225                 230                 235                 240

Cys Gly Ala Leu Lys Asn Val Val Ala Leu Gly Cys Gly Phe Val Glu
                245                 250                 255
```

```
Gly Leu Gly Trp Gly Asn Asn Ala Ser Ala Ala Ile Gln Arg Val Gly
            260                 265                 270

Leu Gly Glu Ile Ile Arg Phe Gly Gln Met Phe Phe Pro Glu Ser Arg
        275                 280                 285

Glu Glu Thr Tyr Tyr Gln Glu Ser Ala Gly Val Ala Asp Leu Ile Thr
    290                 295                 300

Thr Cys Ala Gly Gly Arg Asn Val Lys Val Ala Arg Leu Met Ala Thr
305                 310                 315                 320

Ser Gly Lys Asp Ala Trp Glu Cys Glu Lys Glu Leu Leu Asn Gly Gln
            325                 330                 335

Ser Ala Gln Gly Leu Ile Thr Cys Lys Glu Val His Glu Trp Leu Glu
            340                 345                 350

Thr Cys Gly Ser Val Glu Asp Phe Pro Leu Phe Glu Ala Val Tyr Gln
        355                 360                 365

Ile Val Tyr Asn Asn Tyr Pro Met Lys Asn Leu Pro Asp Met Ile Glu
    370                 375                 380

Glu Leu Asp Leu His Glu Asp
385                 390

<210> SEQ ID NO 3
<211> LENGTH: 1299
<212> TYPE: DNA
<213> ORGANISM: Saccharomyces cerevisiae
<220> FEATURE:
<221> NAME/KEY: CDS
<222> LOCATION: (1)..(1296)
<223> OTHER INFORMATION: coding for G3PDH
<220> FEATURE:
<221> NAME/KEY: CDS
<222> LOCATION: (145)..(1296)
<223> OTHER INFORMATION: coding for G3PDH (alternative Start codon)

<400> SEQUENCE: 3 atg ctt gct gtc aga aga tta aca aga tac aca ttc ctt aag cga acg      48
Met Leu Ala Val Arg Arg Leu Thr Arg Tyr Thr Phe Leu Lys Arg Thr
  1               5                  10                  15 cat ccg gtg tta tat act cgt cgt gca tat aaa att ttg cct tca aga     96
His Pro Val Leu Tyr Thr Arg Arg Ala Tyr Lys Ile Leu Pro Ser Arg
             20                  25                  30 tct act ttc cta aga aga tca tta tta caa aca caa ctg cac tca aag    144
Ser Thr Phe Leu Arg Arg Ser Leu Leu Gln Thr Gln Leu His Ser Lys
         35                  40                  45 atg act gct cat act aat atc aaa cag cac aaa cac tgt cat gag gac    192
Met Thr Ala His Thr Asn Ile Lys Gln His Lys His Cys His Glu Asp
 50                  55                  60 cat cct atc aga aga tcg gac tct gcc gtg tca att gta cat ttg aaa    240
His Pro Ile Arg Arg Ser Asp Ser Ala Val Ser Ile Val His Leu Lys
 65                  70                  75                  80 cgt gcg ccc ttc aag gtt aca gtg att ggt tct ggt aac tgg ggg acc    288
Arg Ala Pro Phe Lys Val Thr Val Ile Gly Ser Gly Asn Trp Gly Thr
                 85                  90                  95 acc atc gcc aaa gtc att gcg gaa aac aca gaa ttg cat tcc cat atc    336
Thr Ile Ala Lys Val Ile Ala Glu Asn Thr Glu Leu His Ser His Ile
            100                 105                 110 ttc gag cca gag gtg aga atg tgg gtt ttt gat gaa aag atc ggc gac    384
Phe Glu Pro Glu Val Arg Met Trp Val Phe Asp Glu Lys Ile Gly Asp
        115                 120                 125 gaa aat ctg acg gat atc ata aat aca aga cac cag aac gtt aaa tat    432
Glu Asn Leu Thr Asp Ile Ile Asn Thr Arg His Gln Asn Val Lys Tyr
    130                 135                 140
```

-continued

```
cta ccc aat att gac ctg ccc cat aat cta gtg gcc gat cct gat ctt        480
Leu Pro Asn Ile Asp Leu Pro His Asn Leu Val Ala Asp Pro Asp Leu
145                 150                 155                 160 tta cac tcc atc aag ggt gct gac atc ctt gtt ttc aac atc cct cat        528
Leu His Ser Ile Lys Gly Ala Asp Ile Leu Val Phe Asn Ile Pro His
            165                 170                 175 caa ttt tta cca aac ata gtc aaa caa ttg caa ggc cac gtg gcc cct        576
Gln Phe Leu Pro Asn Ile Val Lys Gln Leu Gln Gly His Val Ala Pro
        180                 185                 190 cat gta agg gcc atc tcg tgt cta aaa ggg ttc gag ttg ggc tcc aag        624
His Val Arg Ala Ile Ser Cys Leu Lys Gly Phe Glu Leu Gly Ser Lys
    195                 200                 205 ggt gtg caa ttg cta tcc tcc tat gtt act gat gag tta gga atc caa        672
Gly Val Gln Leu Leu Ser Ser Tyr Val Thr Asp Glu Leu Gly Ile Gln
210                 215                 220 tgt ggc gca cta tct ggt gca aac ttg gca ccg gaa gtg gcc aag gag        720
Cys Gly Ala Leu Ser Gly Ala Asn Leu Ala Pro Glu Val Ala Lys Glu
225                 230                 235                 240 cat tgg tcc gaa acc acc gtg gct tac caa cta cca aag gat tat caa        768
His Trp Ser Glu Thr Thr Val Ala Tyr Gln Leu Pro Lys Asp Tyr Gln
                245                 250                 255 ggt gat ggc aag gat gta gat cat aag att ttg aaa ttg ctg ttc cac        816
Gly Asp Gly Lys Asp Val Asp His Lys Ile Leu Lys Leu Leu Phe His
            260                 265                 270 aga cct tac ttc cac gtc aat gtc atc gat gat gtt gct ggt ata tcc        864
Arg Pro Tyr Phe His Val Asn Val Ile Asp Asp Val Ala Gly Ile Ser
        275                 280                 285 att gcc ggt gcc ttg aag aac gtc gtg gca ctt gca tgt ggt ttc gta        912
Ile Ala Gly Ala Leu Lys Asn Val Val Ala Leu Ala Cys Gly Phe Val
    290                 295                 300 gaa ggt atg gga tgg ggt aac aat gcc tcc gca gcc att caa agg ctg        960
Glu Gly Met Gly Trp Gly Asn Asn Ala Ser Ala Ala Ile Gln Arg Leu
305                 310                 315                 320 ggt tta ggt gaa att atc aag ttc ggt aga atg ttt ttc cca gaa tcc       1008
Gly Leu Gly Glu Ile Ile Lys Phe Gly Arg Met Phe Phe Pro Glu Ser
                325                 330                 335 aaa gtc gag acc tac tat caa gaa tcc gct ggt gtt gca gat ctg atc       1056
Lys Val Glu Thr Tyr Tyr Gln Glu Ser Ala Gly Val Ala Asp Leu Ile
            340                 345                 350 acc acc tgc tca ggc ggt aga aac gtc aag gtt gcc aca tac atg gcc       1104
Thr Thr Cys Ser Gly Gly Arg Asn Val Lys Val Ala Thr Tyr Met Ala
        355                 360                 365 aag acc ggt aag tca gcc ttg gaa gca gaa aag gaa ttg ctt aac ggt       1152
Lys Thr Gly Lys Ser Ala Leu Glu Ala Glu Lys Glu Leu Leu Asn Gly
    370                 375                 380 caa tcc gcc caa ggg ata atc aca tgc aga gaa gtt cac gag tgg cta       1200
Gln Ser Ala Gln Gly Ile Ile Thr Cys Arg Glu Val His Glu Trp Leu
385                 390                 395                 400 caa aca tgt gag ttg acc caa gaa ttc cca att att cga ggc agt cta       1248
Gln Thr Cys Glu Leu Thr Gln Glu Phe Pro Ile Ile Arg Gly Ser Leu
                405                 410                 415 cca gat agt cta caa caa cgt ccg cat gga aga cct acc gga gat gat       1296
Pro Asp Ser Leu Gln Gln Arg Pro His Gly Arg Pro Thr Gly Asp Asp
            420                 425                 430 tga                                                                   1299

<210> SEQ ID NO 4
<211> LENGTH: 432
<212> TYPE: PRT
<213> ORGANISM: Saccharomyces cerevisiae
```

<400> SEQUENCE: 4

```
Met Leu Ala Val Arg Arg Leu Thr Arg Tyr Thr Phe Leu Lys Arg Thr
 1               5                  10                  15

His Pro Val Leu Tyr Thr Arg Arg Ala Tyr Lys Ile Leu Pro Ser Arg
             20                  25                  30

Ser Thr Phe Leu Arg Arg Ser Leu Leu Gln Thr Gln Leu His Ser Lys
         35                  40                  45

Met Thr Ala His Thr Asn Ile Lys Gln His Lys His Cys His Glu Asp
     50                  55                  60

His Pro Ile Arg Arg Ser Asp Ser Ala Val Ser Ile Val His Leu Lys
 65                  70                  75                  80

Arg Ala Pro Phe Lys Val Thr Val Ile Gly Ser Gly Asn Trp Gly Thr
                 85                  90                  95

Thr Ile Ala Lys Val Ile Ala Glu Asn Thr Glu Leu His Ser His Ile
             100                 105                 110

Phe Glu Pro Glu Val Arg Met Trp Val Phe Asp Glu Lys Ile Gly Asp
         115                 120                 125

Glu Asn Leu Thr Asp Ile Ile Asn Thr Arg His Gln Asn Val Lys Tyr
     130                 135                 140

Leu Pro Asn Ile Asp Leu Pro His Asn Leu Val Ala Asp Pro Asp Leu
145                 150                 155                 160

Leu His Ser Ile Lys Gly Ala Asp Ile Leu Val Phe Asn Ile Pro His
                 165                 170                 175

Gln Phe Leu Pro Asn Ile Val Lys Gln Leu Gln Gly His Val Ala Pro
             180                 185                 190

His Val Arg Ala Ile Ser Cys Leu Lys Gly Phe Glu Leu Gly Ser Lys
         195                 200                 205

Gly Val Gln Leu Leu Ser Ser Tyr Val Thr Asp Glu Leu Gly Ile Gln
     210                 215                 220

Cys Gly Ala Leu Ser Gly Ala Asn Leu Ala Pro Glu Val Ala Lys Glu
225                 230                 235                 240

His Trp Ser Glu Thr Thr Val Ala Tyr Gln Leu Pro Lys Asp Tyr Gln
                 245                 250                 255

Gly Asp Gly Lys Asp Val Asp His Lys Ile Leu Lys Leu Leu Phe His
             260                 265                 270

Arg Pro Tyr Phe His Val Asn Val Ile Asp Asp Val Ala Gly Ile Ser
         275                 280                 285

Ile Ala Gly Ala Leu Lys Asn Val Val Ala Leu Ala Cys Gly Phe Val
     290                 295                 300

Glu Gly Met Gly Trp Gly Asn Asn Ala Ser Ala Ala Ile Gln Arg Leu
305                 310                 315                 320

Gly Leu Gly Glu Ile Ile Lys Phe Gly Arg Met Phe Phe Pro Glu Ser
                 325                 330                 335

Lys Val Glu Thr Tyr Tyr Gln Glu Ser Ala Gly Val Ala Asp Leu Ile
             340                 345                 350

Thr Thr Cys Ser Gly Gly Arg Asn Val Lys Val Ala Thr Tyr Met Ala
         355                 360                 365

Lys Thr Gly Lys Ser Ala Leu Glu Ala Glu Lys Glu Leu Leu Asn Gly
     370                 375                 380

Gln Ser Ala Gln Gly Ile Ile Thr Cys Arg Glu Val His Glu Trp Leu
385                 390                 395                 400

Gln Thr Cys Glu Leu Thr Gln Glu Phe Pro Ile Ile Arg Gly Ser Leu
```

-continued

```
                      405                 410                 415
    Pro Asp Ser Leu Gln Gln Arg Pro His Gly Arg Pro Thr Gly Asp Asp
                420                 425                 430

<210> SEQ ID NO 5
<211> LENGTH: 384
<212> TYPE: PRT
<213> ORGANISM: Saccharomyces cerevisiae

<400> SEQUENCE: 5

Met Thr Ala His Thr Asn Ile Lys Gln His Lys His Cys His Glu Asp
  1               5                  10                  15

His Pro Ile Arg Arg Ser Asp Ser Ala Val Ser Ile Val His Leu Lys
                 20                  25                  30

Arg Ala Pro Phe Lys Val Thr Val Ile Gly Ser Gly Asn Trp Gly Thr
             35                  40                  45

Thr Ile Ala Lys Val Ile Ala Glu Asn Thr Glu Leu His Ser His Ile
         50                  55                  60

Phe Glu Pro Glu Val Arg Met Trp Val Phe Asp Glu Lys Ile Gly Asp
 65                  70                  75                  80

Glu Asn Leu Thr Asp Ile Ile Asn Thr Arg His Gln Asn Val Lys Tyr
                 85                  90                  95

Leu Pro Asn Ile Asp Leu Pro His Asn Leu Val Ala Asp Pro Asp Leu
            100                 105                 110

Leu His Ser Ile Lys Gly Ala Asp Ile Leu Val Phe Asn Ile Pro His
        115                 120                 125

Gln Phe Leu Pro Asn Ile Val Lys Gln Leu Gln Gly His Val Ala Pro
    130                 135                 140

His Val Arg Ala Ile Ser Cys Leu Lys Gly Phe Glu Leu Gly Ser Lys
145                 150                 155                 160

Gly Val Gln Leu Leu Ser Ser Tyr Val Thr Asp Glu Leu Gly Ile Gln
                165                 170                 175

Cys Gly Ala Leu Ser Gly Ala Asn Leu Ala Pro Glu Val Ala Lys Glu
            180                 185                 190

His Trp Ser Glu Thr Thr Val Ala Tyr Gln Leu Pro Lys Asp Tyr Gln
        195                 200                 205

Gly Asp Gly Lys Asp Val Asp His Lys Ile Leu Lys Leu Leu Phe His
    210                 215                 220

Arg Pro Tyr Phe His Val Asn Val Ile Asp Asp Val Ala Gly Ile Ser
225                 230                 235                 240

Ile Ala Gly Ala Leu Lys Asn Val Val Ala Leu Ala Cys Gly Phe Val
                245                 250                 255

Glu Gly Met Gly Trp Gly Asn Asn Ala Ser Ala Ala Ile Gln Arg Leu
            260                 265                 270

Gly Leu Gly Glu Ile Ile Lys Phe Gly Arg Met Phe Phe Pro Glu Ser
        275                 280                 285

Lys Val Glu Thr Tyr Tyr Gln Glu Ser Ala Gly Val Ala Asp Leu Ile
    290                 295                 300

Thr Thr Cys Ser Gly Gly Arg Asn Val Lys Val Ala Thr Tyr Met Ala
305                 310                 315                 320

Lys Thr Gly Lys Ser Ala Leu Glu Ala Glu Lys Glu Leu Leu Asn Gly
                325                 330                 335

Gln Ser Ala Gln Gly Ile Ile Thr Cys Arg Glu Val His Glu Trp Leu
            340                 345                 350
```

```
Gln Thr Cys Glu Leu Thr Gln Glu Phe Pro Ile Ile Arg Gly Ser Leu
            355                 360                 365

Pro Asp Ser Leu Gln Gln Arg Pro His Gly Arg Pro Thr Gly Asp Asp
    370                 375                 380

<210> SEQ ID NO 6
<211> LENGTH: 1122
<212> TYPE: DNA
<213> ORGANISM: Schizosaccharomyces pombe
<220> FEATURE:
<221> NAME/KEY: CDS
<222> LOCATION: (1)..(1119)
<223> OTHER INFORMATION: coding for G3PDH

<400> SEQUENCE: 6 atg act gtg gct gct ttg aac aaa ctc agc gct ctc tcc gga agt att      48
Met Thr Val Ala Ala Leu Asn Lys Leu Ser Ala Leu Ser Gly Ser Ile
  1               5                  10                  15 caa aaa tct ttt tca cct aaa ctt att tct gtt ggt atc atc gga tca      96
Gln Lys Ser Phe Ser Pro Lys Leu Ile Ser Val Gly Ile Ile Gly Ser
             20                  25                  30 gga aat tgg gga acc gct att gct aaa ata tgt ggt gaa aat gcc aag     144
Gly Asn Trp Gly Thr Ala Ile Ala Lys Ile Cys Gly Glu Asn Ala Lys
         35                  40                  45 gct cat cct gat att ttc cat cct caa gta cac atg tgg atg tat gaa     192
Ala His Pro Asp Ile Phe His Pro Gln Val His Met Trp Met Tyr Glu
     50                  55                  60 gag aag att caa cat gag gga aaa gag tgc aat ctc acg gaa gtt ttt     240
Glu Lys Ile Gln His Glu Gly Lys Glu Cys Asn Leu Thr Glu Val Phe
 65                  70                  75                  80 aac act act cat gaa aac gtt aaa tat ctc aaa ggt atc aaa tgc cct     288
Asn Thr Thr His Glu Asn Val Lys Tyr Leu Lys Gly Ile Lys Cys Pro
                 85                  90                  95 tct aac gtc ttc gca aac ccg gac att cgt gat gta ggt tca cgt agc     336
Ser Asn Val Phe Ala Asn Pro Asp Ile Arg Asp Val Gly Ser Arg Ser
            100                 105                 110 gac att ctg gta tgg gtt ctc cct cac cag ttc gtt gtg cgt att tgc     384
Asp Ile Leu Val Trp Val Leu Pro His Gln Phe Val Val Arg Ile Cys
        115                 120                 125 aat caa ttg aag gga tgc cta aag aag gat gct gtt gca att tca tgc     432
Asn Gln Leu Lys Gly Cys Leu Lys Lys Asp Ala Val Ala Ile Ser Cys
    130                 135                 140 atc aaa ggt gta tct gtc acc aag gac cgt gtt cgc ctc ttt tct gat     480
Ile Lys Gly Val Ser Val Thr Lys Asp Arg Val Arg Leu Phe Ser Asp
145                 150                 155                 160 att atc gaa gaa aac acg gga atg tat tgt ggc gtt ctc tct ggc gcc     528
Ile Ile Glu Glu Asn Thr Gly Met Tyr Cys Gly Val Leu Ser Gly Ala
                165                 170                 175 aac att gcc agc gaa gtt gct caa gag aag ttt tgc gaa act act atc     576
Asn Ile Ala Ser Glu Val Ala Gln Glu Lys Phe Cys Glu Thr Thr Ile
            180                 185                 190 gga tat ttg cct aat agt tct gtt aat ccc cgc tat act cct aag act     624
Gly Tyr Leu Pro Asn Ser Ser Val Asn Pro Arg Tyr Thr Pro Lys Thr
        195                 200                 205 atc caa gct ttg ttt aac cgt ccc tac ttc cgt gtc aac att gtt gag     672
Ile Gln Ala Leu Phe Asn Arg Pro Tyr Phe Arg Val Asn Ile Val Glu
    210                 215                 220 gat gtt cct ggt gtt gct ttg ggc ggt gca ctc aag aat atc gtc gct     720
Asp Val Pro Gly Val Ala Leu Gly Gly Ala Leu Lys Asn Ile Val Ala
225                 230                 235                 240 gtc gct gcc ggt att att gat gga ctt gaa ttg gga gat aat acc aaa     768
```

-continued

| | | | | | | | | | | | | | | | |
|---|---|---|---|---|---|---|---|---|---|---|---|---|---|---|---|
|Val|Ala|Ala|Gly|Ile|Ile|Asp|Gly|Leu|Glu|Leu|Gly|Asp|Asn|Thr|Lys|
| | | | |245| | | |250| | | | |255| | |

```
tct gct gtt atg cgc att ggc ctt ctg gaa atg cag aaa ttc ggc agg      816
Ser Ala Val Met Arg Ile Gly Leu Leu Glu Met Gln Lys Phe Gly Arg
        260                 265                 270 atg ttt ttc gat tgt aag cct ctt act atg agc gag gaa tct tgt ggc      864
Met Phe Phe Asp Cys Lys Pro Leu Thr Met Ser Glu Glu Ser Cys Gly
    275                 280                 285 ata gcc gat tta att aca act tgc tta ggc ggc cgt aac cac aaa tgc      912
Ile Ala Asp Leu Ile Thr Thr Cys Leu Gly Gly Arg Asn His Lys Cys
290                 295                 300 gct gtg gca ttt gtc aag aca gga aag ccc atg cat gtt gtt gaa caa      960
Ala Val Ala Phe Val Lys Thr Gly Lys Pro Met His Val Val Glu Gln
305                 310                 315                 320 gaa ctt ctt gat ggt cag aag ttg caa ggt gca gct acc gcg aag gag     1008
Glu Leu Leu Asp Gly Gln Lys Leu Gln Gly Ala Ala Thr Ala Lys Glu
                325                 330                 335 gtt tat gag ttc ctt gat aac cag aat aag gta agc gaa ttc cca ttg     1056
Val Tyr Glu Phe Leu Asp Asn Gln Asn Lys Val Ser Glu Phe Pro Leu
            340                 345                 350 ttt aca gct gtt tat cgc att gtt tat gag gga ctt cca cct aat aag     1104
Phe Thr Ala Val Tyr Arg Ile Val Tyr Glu Gly Leu Pro Pro Asn Lys
        355                 360                 365 ctt ctg gag gct att taa                                             1122
Leu Leu Glu Ala Ile
    370

<210> SEQ ID NO 7
<211> LENGTH: 373
<212> TYPE: PRT
<213> ORGANISM: Schizosaccharomyces pombe

<400> SEQUENCE: 7

Met Thr Val Ala Ala Leu Asn Lys Leu Ser Ala Leu Ser Gly Ser Ile
  1               5                  10                  15

Gln Lys Ser Phe Ser Pro Lys Leu Ile Ser Val Gly Ile Ile Gly Ser
             20                  25                  30

Gly Asn Trp Gly Thr Ala Ile Ala Lys Ile Cys Gly Glu Asn Ala Lys
         35                  40                  45

Ala His Pro Asp Ile Phe His Pro Gln Val His Met Trp Met Tyr Glu
     50                  55                  60

Glu Lys Ile Gln His Glu Gly Lys Glu Cys Asn Leu Thr Glu Val Phe
 65                  70                  75                  80

Asn Thr Thr His Glu Asn Val Lys Tyr Leu Lys Gly Ile Lys Cys Pro
                 85                  90                  95

Ser Asn Val Phe Ala Asn Pro Asp Ile Arg Asp Val Gly Ser Arg Ser
            100                 105                 110

Asp Ile Leu Val Trp Val Leu Pro His Gln Phe Val Arg Ile Cys
        115                 120                 125

Asn Gln Leu Lys Gly Cys Leu Lys Lys Asp Ala Val Ala Ile Ser Cys
    130                 135                 140

Ile Lys Gly Val Ser Val Thr Lys Asp Arg Val Arg Leu Phe Ser Asp
145                 150                 155                 160

Ile Ile Glu Glu Asn Thr Gly Met Tyr Cys Gly Val Leu Ser Gly Ala
                165                 170                 175

Asn Ile Ala Ser Glu Val Ala Gln Glu Lys Phe Cys Glu Thr Thr Ile
            180                 185                 190
```

```
Gly Tyr Leu Pro Asn Ser Ser Val Asn Pro Arg Tyr Thr Pro Lys Thr
            195                 200                 205

Ile Gln Ala Leu Phe Asn Arg Pro Tyr Phe Arg Val Asn Ile Val Glu
    210                 215                 220

Asp Val Pro Gly Val Ala Leu Gly Gly Ala Leu Lys Asn Ile Val Ala
225                 230                 235                 240

Val Ala Ala Gly Ile Ile Asp Gly Leu Glu Leu Gly Asp Asn Thr Lys
                245                 250                 255

Ser Ala Val Met Arg Ile Gly Leu Leu Glu Met Gln Lys Phe Gly Arg
            260                 265                 270

Met Phe Phe Asp Cys Lys Pro Leu Thr Met Ser Glu Ser Cys Gly
        275                 280                 285

Ile Ala Asp Leu Ile Thr Thr Cys Leu Gly Gly Arg Asn His Lys Cys
        290                 295                 300

Ala Val Ala Phe Val Lys Thr Gly Lys Pro Met His Val Val Glu Gln
305                 310                 315                 320

Glu Leu Leu Asp Gly Gln Lys Leu Gln Gly Ala Ala Thr Ala Lys Glu
                325                 330                 335

Val Tyr Glu Phe Leu Asp Asn Gln Asn Lys Val Ser Glu Phe Pro Leu
            340                 345                 350

Phe Thr Ala Val Tyr Arg Ile Val Tyr Glu Gly Leu Pro Pro Asn Lys
        355                 360                 365

Leu Leu Glu Ala Ile
    370

<210> SEQ ID NO 8
<211> LENGTH: 1155
<212> TYPE: DNA
<213> ORGANISM: Schizosaccharomyces pombe
<220> FEATURE:
<221> NAME/KEY: CDS
<222> LOCATION: (1)..(1152)
<223> OTHER INFORMATION: coding for G3PDH

<400> SEQUENCE: 8 atg tct gga tat ggt caa caa ggt gtt tct gct gcc aac atc gac agc    48
Met Ser Gly Tyr Gly Gln Gln Gly Val Ser Ala Ala Asn Ile Asp Ser
 1               5                  10                  15 atc cgc ccc aag aaa cgt ttg tca att ggt gta gtt ggc tcc ggt aac    96
Ile Arg Pro Lys Lys Arg Leu Ser Ile Gly Val Val Gly Ser Gly Asn
             20                  25                  30 tgg ggt act gcc att gcc aag att tgc ggt gaa aat gcc cgt gcc cac   144
Trp Gly Thr Ala Ile Ala Lys Ile Cys Gly Glu Asn Ala Arg Ala His
         35                  40                  45 ggt cac cat ttc aga ggt aag ggg cgc atg tgg gtc ttt gag gag gag   192
Gly His His Phe Arg Gly Lys Gly Arg Met Trp Val Phe Glu Glu Glu
     50                  55                  60 att gag tac aag ggt gag aag aga aag ctc acc gaa gta ttc aac gaa   240
Ile Glu Tyr Lys Gly Glu Lys Arg Lys Leu Thr Glu Val Phe Asn Glu
 65                  70                  75                  80 gct cac gag aat gtc aaa tac tta ccc ggc atc gaa tgc cct ccc aac   288
Ala His Glu Asn Val Lys Tyr Leu Pro Gly Ile Glu Cys Pro Pro Asn
                 85                  90                  95 gtt att gcc gtc ccc gat gtt cgt gag gtc gct aga cgt gcc gac atc   336
Val Ile Ala Val Pro Asp Val Arg Glu Val Ala Arg Arg Ala Asp Ile
            100                 105                 110 ctt gtc ttt gtc gtt cct cat caa ttt att gaa cgc gtt tgg cac caa   384
Leu Val Phe Val Val Pro His Gln Phe Ile Glu Arg Val Trp His Gln
        115                 120                 125
```

```
atg gtc ggt ctc att cgc cct ggt gcc gtt ggt att tcc tgt atc aag     432
Met Val Gly Leu Ile Arg Pro Gly Ala Val Gly Ile Ser Cys Ile Lys
    130                 135                 140 ggt gtt gct gtc agc aag gaa ggc tcg ctt tac tct gag gtt atc agc     480
Gly Val Ala Val Ser Lys Glu Gly Ser Leu Tyr Ser Glu Val Ile Ser
145                 150                 155                 160 gag aaa ctc ggt att tac tgt ggt gtt ctt tct ggt gct aac gtt gca     528
Glu Lys Leu Gly Ile Tyr Cys Gly Val Leu Ser Gly Ala Asn Val Ala
                165                 170                 175 aac gaa gtt gcc cgt gag caa ttc tgt gag act act att ggt ttc aac     576
Asn Glu Val Ala Arg Glu Gln Phe Cys Glu Thr Thr Ile Gly Phe Asn
            180                 185                 190 cct cct aat gaa gtt gat atc cct cgc gag caa atc gcc gcc gtc tct     624
Pro Pro Asn Glu Val Asp Ile Pro Arg Glu Gln Ile Ala Ala Val Ser
        195                 200                 205 gat cgc cct tac ttc tca gtt gtc tcc gtt gac gac gtt gcc ggt gtc     672
Asp Arg Pro Tyr Phe Ser Val Val Ser Val Asp Asp Val Ala Gly Val
    210                 215                 220 gcc ttg ggt ggt gct ttg aag aac gta gtt gcc atg gcc gtt ggt ttc     720
Ala Leu Gly Gly Ala Leu Lys Asn Val Val Ala Met Ala Val Gly Phe
225                 230                 235                 240 gct gat ggt ttg gaa tgg ggc ggt aat acc aag gcc gct att atg cgt     768
Ala Asp Gly Leu Glu Trp Gly Gly Asn Thr Lys Ala Ala Ile Met Arg
                245                 250                 255 cgt ggt ttg ttg gag atg caa aag ttt gct act acc ttc ttc gac tct     816
Arg Gly Leu Leu Glu Met Gln Lys Phe Ala Thr Thr Phe Phe Asp Ser
            260                 265                 270 gat cct cgt acc atg gtt gag caa tct tgc ggt atc gct gac ttg gtc     864
Asp Pro Arg Thr Met Val Glu Gln Ser Cys Gly Ile Ala Asp Leu Val
        275                 280                 285 act tct tgt ttg ggt ggc cgt aac aat cgt tgt gct gaa gca ttt gtc     912
Thr Ser Cys Leu Gly Gly Arg Asn Asn Arg Cys Ala Glu Ala Phe Val
    290                 295                 300 aag act ggt aaa tct tta gag acg ctt gaa aaa gag ctc tta ggt ggt     960
Lys Thr Gly Lys Ser Leu Glu Thr Leu Glu Lys Glu Leu Leu Gly Gly
305                 310                 315                 320 caa ctt ctt caa gga gct gcc act tcc aag gat gtt cat gaa ttc ctt    1008
Gln Leu Leu Gln Gly Ala Ala Thr Ser Lys Asp Val His Glu Phe Leu
                325                 330                 335 ctc acc aag gat atg gtc aag gat ttc ccc ttg ttc act gcc gtt tat    1056
Leu Thr Lys Asp Met Val Lys Asp Phe Pro Leu Phe Thr Ala Val Tyr
            340                 345                 350 aac att tcc tat gaa gac atg gat ccc aag gat ttg atc atc gtc ctt    1104
Asn Ile Ser Tyr Glu Asp Met Asp Pro Lys Asp Leu Ile Ile Val Leu
        355                 360                 365 caa ccc ctt aag gag gac tct gag aac gag ggc ggt act gaa acc gag    1152
Gln Pro Leu Lys Glu Asp Ser Glu Asn Glu Gly Gly Thr Glu Thr Glu
    370                 375                 380 taa                                                                1155

<210> SEQ ID NO 9
<211> LENGTH: 384
<212> TYPE: PRT
<213> ORGANISM: Schizosaccharomyces pombe

<400> SEQUENCE: 9

Met Ser Gly Tyr Gly Gln Gln Gly Val Ser Ala Ala Asn Ile Asp Ser
 1               5                  10                  15

Ile Arg Pro Lys Lys Arg Leu Ser Ile Gly Val Val Gly Ser Gly Asn
```

```
                    20                  25                  30

Trp Gly Thr Ala Ile Ala Lys Ile Cys Gly Glu Asn Ala Arg Ala His
         35                  40                  45

Gly His His Phe Arg Gly Lys Gly Arg Met Trp Val Phe Glu Glu Glu
     50                  55                  60

Ile Glu Tyr Lys Gly Glu Lys Arg Lys Leu Thr Glu Val Phe Asn Glu
 65                  70                  75                  80

Ala His Glu Asn Val Lys Tyr Leu Pro Gly Ile Glu Cys Pro Pro Asn
                 85                  90                  95

Val Ile Ala Val Pro Asp Val Arg Glu Val Ala Arg Arg Ala Asp Ile
            100                 105                 110

Leu Val Phe Val Val Pro His Gln Phe Ile Glu Arg Val Trp His Gln
        115                 120                 125

Met Val Gly Leu Ile Arg Pro Gly Ala Val Gly Ile Ser Cys Ile Lys
    130                 135                 140

Gly Val Ala Val Ser Lys Glu Gly Ser Leu Tyr Ser Glu Val Ile Ser
145                 150                 155                 160

Glu Lys Leu Gly Ile Tyr Cys Gly Val Leu Ser Gly Ala Asn Val Ala
                165                 170                 175

Asn Glu Val Ala Arg Glu Gln Phe Cys Glu Thr Thr Ile Gly Phe Asn
            180                 185                 190

Pro Pro Asn Glu Val Asp Ile Pro Arg Glu Gln Ile Ala Ala Val Ser
        195                 200                 205

Asp Arg Pro Tyr Phe Ser Val Ser Val Asp Val Ala Gly Val
    210                 215                 220

Ala Leu Gly Gly Ala Leu Lys Asn Val Val Ala Met Ala Val Gly Phe
225                 230                 235                 240

Ala Asp Gly Leu Glu Trp Gly Gly Asn Thr Lys Ala Ala Ile Met Arg
                245                 250                 255

Arg Gly Leu Leu Glu Met Gln Lys Phe Ala Thr Thr Phe Phe Asp Ser
            260                 265                 270

Asp Pro Arg Thr Met Val Glu Gln Ser Cys Gly Ile Ala Asp Leu Val
        275                 280                 285

Thr Ser Cys Leu Gly Gly Arg Asn Asn Arg Cys Ala Glu Ala Phe Val
    290                 295                 300

Lys Thr Gly Lys Ser Leu Glu Thr Leu Glu Lys Glu Leu Leu Gly Gly
305                 310                 315                 320

Gln Leu Leu Gln Gly Ala Ala Thr Ser Lys Asp Val His Glu Phe Leu
                325                 330                 335

Leu Thr Lys Asp Met Val Lys Asp Phe Pro Leu Phe Thr Ala Val Tyr
            340                 345                 350

Asn Ile Ser Tyr Glu Asp Met Asp Pro Lys Asp Leu Ile Ile Val Leu
        355                 360                 365

Gln Pro Leu Lys Glu Asp Ser Glu Asn Glu Gly Gly Thr Glu Thr Glu
    370                 375                 380

<210> SEQ ID NO 10
<211> LENGTH: 1197
<212> TYPE: DNA
<213> ORGANISM: Yarrowia lipolytica
<220> FEATURE:
<221> NAME/KEY: CDS
<222> LOCATION: (1)..(1194)
<223> OTHER INFORMATION: coding for G3PDH
<220> FEATURE:
<221> NAME/KEY: CDS
```

-continued

<222> LOCATION: (40)..(1194)

<400> SEQUENCE: 10

| atg agc gct cta ctt aga tcg tcc ctg cgt ttt aaa cac atg tcc gcc | 48 |
| Met Ser Ala Leu Leu Arg Ser Ser Leu Arg Phe Lys His Met Ser Ala | |
|   1               5                   10                  15    | |

| gtc aac cgt ctc aca caa cag ctt cga ctg ctg acc gcc tcc gcg cct | 96 |
| Val Asn Arg Leu Thr Gln Gln Leu Arg Leu Leu Thr Ala Ser Ala Pro | |
|              20                  25                  30         | |

| ctc agc gca gcc aac acc gcc ggc aag gct cct ttc aag gtc gcc gtt | 144 |
| Leu Ser Ala Ala Asn Thr Ala Gly Lys Ala Pro Phe Lys Val Ala Val | |
|         35                  40                  45              | |

| gtt ggt tct ggt aac tgg gga acc acc gtc gcc aag att gtc gcc gag | 192 |
| Val Gly Ser Gly Asn Trp Gly Thr Thr Val Ala Lys Ile Val Ala Glu | |
| 50                  55                  60                      | |

| aac tgc act gct cac ccc gag ctc ttt gag ccc gag gtt cga gtc tgg | 240 |
| Asn Cys Thr Ala His Pro Glu Leu Phe Glu Pro Glu Val Arg Val Trp | |
|  65                  70                  75                  80 | |

| gtt cga gaa gag aag gtc aac ggc aag aac ctg acc gac att ttc aac | 288 |
| Val Arg Glu Glu Lys Val Asn Gly Lys Asn Leu Thr Asp Ile Phe Asn | |
|                 85                  90                  95      | |

| gct gag cac gag aac gtg cga tac ctc cct aaa atc aaa ctt cct cac | 336 |
| Ala Glu His Glu Asn Val Arg Tyr Leu Pro Lys Ile Lys Leu Pro His | |
|            100                 105                 110          | |

| aac ctg atc gcc gag ccg gat ctg ctc aag gcc gtc gag ggt gcc aac | 384 |
| Asn Leu Ile Ala Glu Pro Asp Leu Leu Lys Ala Val Glu Gly Ala Asn | |
|       115                 120                 125               | |

| atc atc gtc ttc aac ctg ccc cat cag ttc ctg gct ggt gtc tgc aag | 432 |
| Ile Ile Val Phe Asn Leu Pro His Gln Phe Leu Ala Gly Val Cys Lys | |
|  130                 135                 140                    | |

| cag ctc aag ggc cac gtc aac ccc aag gct aga gcc atc tcc tgc ctc | 480 |
| Gln Leu Lys Gly His Val Asn Pro Lys Ala Arg Ala Ile Ser Cys Leu | |
| 145                 150                 155                 160 | |

| aag ggt cta gat gtc acc ccc cag ggt gtt tac ctg ctc tcc gac gtt | 528 |
| Lys Gly Leu Asp Val Thr Pro Gln Gly Val Tyr Leu Leu Ser Asp Val | |
|                 165                 170                 175     | |

| atc gag aac gag acc ggt ctc cac tgc ggt gtt ctg tcc ggg gct aac | 576 |
| Ile Glu Asn Glu Thr Gly Leu His Cys Gly Val Leu Ser Gly Ala Asn | |
|            180                 185                 190          | |

| ctc gcc acc gag atc gct ctg gag aag tac tcc gag act acc gtt gct | 624 |
| Leu Ala Thr Glu Ile Ala Leu Glu Lys Tyr Ser Glu Thr Thr Val Ala | |
|       195                 200                 205               | |

| tac aac cga ccc aag gac ttc ttt ggc gag ggt gat gtg acc aac gat | 672 |
| Tyr Asn Arg Pro Lys Asp Phe Phe Gly Glu Gly Asp Val Thr Asn Asp | |
|  210                 215                 220                    | |

| gtg ctc aag gct ctg ttc cac cga ccc tac ttc cat gtg cga tgc gtt | 720 |
| Val Leu Lys Ala Leu Phe His Arg Pro Tyr Phe His Val Arg Cys Val | |
| 225                 230                 235                 240 | |

| cag gac gtc gcc ggt gtc tcc atc gga ggt gcc ctt aag aac gtt gtt | 768 |
| Gln Asp Val Ala Gly Val Ser Ile Gly Gly Ala Leu Lys Asn Val Val | |
|                 245                 250                 255     | |

| gcc ctt tgc gcc ggt ttc gtc gag ggc aag aac tgg gga gac aac gcc | 816 |
| Ala Leu Cys Ala Gly Phe Val Glu Gly Lys Asn Trp Gly Asp Asn Ala | |
|            260                 265                 270          | |

| aag gcc gca att atg cga cga ggc atg ctt gag atg atc aac ttc tcc | 864 |
| Lys Ala Ala Ile Met Arg Arg Gly Met Leu Glu Met Ile Asn Phe Ser | |
|       275                 280                 285               | |

| aag cga ttc ttc ccc gaa act gat att aac act ctt aca gtc gag tct | 912 |
| Lys Arg Phe Phe Pro Glu Thr Asp Ile Asn Thr Leu Thr Val Glu Ser | |
|  290                 295                 300                    | |

```
gcc ggt gtg gcc gat ctc atc acc tcg tgc gct gga ggc cga aac ttc    960
Ala Gly Val Ala Asp Leu Ile Thr Ser Cys Ala Gly Gly Arg Asn Phe
305                 310                 315                 320 aag gtc ggc cga gca ttc gga aag gag agc ggc tcc ggc aag acc atc   1008
Lys Val Gly Arg Ala Phe Gly Lys Glu Ser Gly Ser Gly Lys Thr Ile
                325                 330                 335 cag gac gtg gag aag gag ctt ctc aac ggc cag tcc gcc cag ggc gtc   1056
Gln Asp Val Glu Lys Glu Leu Leu Asn Gly Gln Ser Ala Gln Gly Val
            340                 345                 350 atc aca tgt aac gag gtc cac gag ctg ctc aag aac aag aac atg cag   1104
Ile Thr Cys Asn Glu Val His Glu Leu Leu Lys Asn Lys Asn Met Gln
        355                 360                 365 aag gac ttc cct ctg ttc gag tcc acc tgg ggc att atc cac ggt gag   1152
Lys Asp Phe Pro Leu Phe Glu Ser Thr Trp Gly Ile Ile His Gly Glu
370                 375                 380 ctc aag att gat gat ctc ccc gag att ctt tac cac gcc aac    tag   1197
Leu Lys Ile Asp Asp Leu Pro Glu Ile Leu Tyr His Ala Asn
385                 390                 395

<210> SEQ ID NO 11
<211> LENGTH: 398
<212> TYPE: PRT
<213> ORGANISM: Yarrowia lipolytica

<400> SEQUENCE: 11

Met Ser Ala Leu Leu Arg Ser Ser Leu Arg Phe Lys His Met Ser Ala
1               5                   10                  15

Val Asn Arg Leu Thr Gln Gln Leu Arg Leu Leu Thr Ala Ser Ala Pro
            20                  25                  30

Leu Ser Ala Ala Asn Thr Ala Gly Lys Ala Pro Phe Lys Val Ala Val
        35                  40                  45

Val Gly Ser Gly Asn Trp Gly Thr Thr Val Ala Lys Ile Val Ala Glu
    50                  55                  60

Asn Cys Thr Ala His Pro Glu Leu Phe Glu Pro Glu Val Arg Val Trp
65                  70                  75                  80

Val Arg Glu Glu Lys Val Asn Gly Lys Asn Leu Thr Asp Ile Phe Asn
                85                  90                  95

Ala Glu His Glu Asn Val Arg Tyr Leu Pro Lys Ile Lys Leu Pro His
            100                 105                 110

Asn Leu Ile Ala Glu Pro Asp Leu Leu Lys Ala Val Glu Gly Ala Asn
        115                 120                 125

Ile Ile Val Phe Asn Leu Pro His Gln Phe Leu Ala Gly Val Cys Lys
    130                 135                 140

Gln Leu Lys Gly His Val Asn Pro Lys Ala Arg Ala Ile Ser Cys Leu
145                 150                 155                 160

Lys Gly Leu Asp Val Thr Pro Gln Gly Val Tyr Leu Leu Ser Asp Val
                165                 170                 175

Ile Glu Asn Glu Thr Gly Leu His Cys Gly Val Leu Ser Gly Ala Asn
            180                 185                 190

Leu Ala Thr Glu Ile Ala Leu Glu Lys Tyr Ser Glu Thr Thr Val Ala
        195                 200                 205

Tyr Asn Arg Pro Lys Asp Phe Phe Gly Glu Gly Asp Val Thr Asn Asp
    210                 215                 220

Val Leu Lys Ala Leu Phe His Arg Pro Tyr Phe His Val Arg Cys Val
225                 230                 235                 240

Gln Asp Val Ala Gly Val Ser Ile Gly Gly Ala Leu Lys Asn Val Val
```

```
                245                 250                 255
Ala Leu Cys Ala Gly Phe Val Glu Gly Lys Asn Trp Gly Asp Asn Ala
            260                 265                 270

Lys Ala Ala Ile Met Arg Arg Gly Met Leu Glu Met Ile Asn Phe Ser
        275                 280                 285

Lys Arg Phe Phe Pro Glu Thr Asp Ile Asn Thr Leu Thr Val Glu Ser
    290                 295                 300

Ala Gly Val Ala Asp Leu Ile Thr Ser Cys Ala Gly Gly Arg Asn Phe
305                 310                 315                 320

Lys Val Gly Arg Ala Phe Gly Lys Glu Ser Gly Ser Gly Lys Thr Ile
                325                 330                 335

Gln Asp Val Glu Lys Glu Leu Leu Asn Gly Gln Ser Ala Gln Gly Val
            340                 345                 350

Ile Thr Cys Asn Glu Val His Glu Leu Leu Lys Asn Lys Asn Met Gln
        355                 360                 365

Lys Asp Phe Pro Leu Phe Glu Ser Thr Trp Gly Ile Ile His Gly Glu
    370                 375                 380

Leu Lys Ile Asp Asp Leu Pro Glu Ile Leu Tyr His Ala Asn
385                 390                 395

<210> SEQ ID NO 12
<211> LENGTH: 385
<212> TYPE: PRT
<213> ORGANISM: Yarrowia lipolytica

<400> SEQUENCE: 12

Met Ser Ala Val Asn Arg Leu Thr Gln Gln Leu Arg Leu Leu Thr Ala
  1               5                  10                  15

Ser Ala Pro Leu Ser Ala Ala Asn Thr Ala Gly Lys Ala Pro Phe Lys
                 20                  25                  30

Val Ala Val Val Gly Ser Gly Asn Trp Gly Thr Thr Val Ala Lys Ile
             35                  40                  45

Val Ala Glu Asn Cys Thr Ala His Pro Glu Leu Phe Glu Pro Glu Val
         50                  55                  60

Arg Val Trp Val Arg Glu Glu Lys Val Asn Gly Lys Asn Leu Thr Asp
 65                  70                  75                  80

Ile Phe Asn Ala Glu His Glu Asn Val Arg Tyr Leu Pro Lys Ile Lys
                 85                  90                  95

Leu Pro His Asn Leu Ile Ala Glu Pro Asp Leu Leu Lys Ala Val Glu
                100                 105                 110

Gly Ala Asn Ile Ile Val Phe Asn Leu Pro His Gln Phe Leu Ala Gly
            115                 120                 125

Val Cys Lys Gln Leu Lys Gly His Val Asn Pro Lys Ala Arg Ala Ile
130                 135                 140

Ser Cys Leu Lys Gly Leu Asp Val Thr Pro Gln Gly Val Tyr Leu Leu
145                 150                 155                 160

Ser Asp Val Ile Glu Asn Glu Thr Gly Leu His Cys Gly Val Leu Ser
                165                 170                 175

Gly Ala Asn Leu Ala Thr Glu Ile Ala Leu Glu Lys Tyr Ser Glu Thr
            180                 185                 190

Thr Val Ala Tyr Asn Arg Pro Lys Asp Phe Phe Gly Glu Gly Asp Val
        195                 200                 205

Thr Asn Asp Val Leu Lys Ala Leu Phe His Arg Pro Tyr Phe His Val
    210                 215                 220
```

```
Arg Cys Val Gln Asp Val Ala Gly Val Ser Ile Gly Gly Ala Leu Lys
225                 230                 235                 240

Asn Val Val Ala Leu Cys Ala Gly Phe Val Glu Gly Lys Asn Trp Gly
                245                 250                 255

Asp Asn Ala Lys Ala Ile Met Arg Arg Gly Met Leu Glu Met Ile
            260                 265                 270

Asn Phe Ser Lys Arg Phe Phe Pro Glu Thr Asp Ile Asn Thr Leu Thr
            275                 280                 285

Val Glu Ser Ala Gly Val Ala Asp Leu Ile Thr Ser Cys Ala Gly Gly
        290                 295                 300

Arg Asn Phe Lys Val Gly Arg Ala Phe Gly Lys Ser Gly Ser Gly
305                 310                 315                 320

Lys Thr Ile Gln Asp Val Glu Lys Glu Leu Leu Asn Gly Gln Ser Ala
                325                 330                 335

Gln Gly Val Ile Thr Cys Asn Glu Val His Glu Leu Leu Lys Asn Lys
            340                 345                 350

Asn Met Gln Lys Asp Phe Pro Leu Phe Glu Ser Thr Trp Gly Ile Ile
        355                 360                 365

His Gly Glu Leu Lys Ile Asp Asp Leu Pro Glu Ile Leu Tyr His Ala
370                 375                 380

Asn
385

<210> SEQ ID NO 13
<211> LENGTH: 1206
<212> TYPE: DNA
<213> ORGANISM: Zygosaccharomyces rouxii
<220> FEATURE:
<221> NAME/KEY: CDS
<222> LOCATION: (1)..(1203)
<223> OTHER INFORMATION: coding for G3PDH

<400> SEQUENCE: 13 atg gcc gct act gac aga tta aac caa acc tct gat atc cta tcg caa        48
Met Ala Ala Thr Asp Arg Leu Asn Gln Thr Ser Asp Ile Leu Ser Gln
  1               5                  10                  15 tct atg aag aag acc gac tca tca atg tca gtc gtt acc gct gag aat        96
Ser Met Lys Lys Thr Asp Ser Ser Met Ser Val Val Thr Ala Glu Asn
             20                  25                  30 cca tac aaa gtt tcc gtc gtc ggc tct ggt aac tgg ggt acc acc atc       144
Pro Tyr Lys Val Ser Val Val Gly Ser Gly Asn Trp Gly Thr Thr Ile
         35                  40                  45 gcc aag gtc gtt gcc gaa aac acc aag gaa aag cca gaa ttg ttc caa       192
Ala Lys Val Val Ala Glu Asn Thr Lys Glu Lys Pro Glu Leu Phe Gln
     50                  55                  60 gaa cgt gtg gac atg tgg gtg ttt gaa gaa cag atc gac ggt act cca       240
Glu Arg Val Asp Met Trp Val Phe Glu Glu Gln Ile Asp Gly Thr Pro
 65                  70                  75                  80 ttg gcc caa atc atc aac acc aag cac cag aac gtg aaa tac ttg cca       288
Leu Ala Gln Ile Ile Asn Thr Lys His Gln Asn Val Lys Tyr Leu Pro
                 85                  90                  95 aac atc gac ctt ccg gac aat ttg gtc gct aac cca gac ttg att gcc       336
Asn Ile Asp Leu Pro Asp Asn Leu Val Ala Asn Pro Asp Leu Ile Ala
            100                 105                 110 acc acg aag gac gcc gat gtg att gtt ttc aac gtt ccc cat caa ttt       384
Thr Thr Lys Asp Ala Asp Val Ile Val Phe Asn Val Pro His Gln Phe
        115                 120                 125 ttg ggc cgt atc gtt gct caa atg aag ggt caa atc aaa cca act gca       432
Leu Gly Arg Ile Val Ala Gln Met Lys Gly Gln Ile Lys Pro Thr Ala
```

```
                    130                 135                 140
cgt gcg gtc tcc tgt cta aag ggt ttc gaa gtt ggt cca aag ggt gtg    480
Arg Ala Val Ser Cys Leu Lys Gly Phe Glu Val Gly Pro Lys Gly Val
145                 150                 155                 160 cag ctt cta tct gac tac gtc act caa gaa ttg ggt atc gaa tgt ggt    528
Gln Leu Leu Ser Asp Tyr Val Thr Gln Glu Leu Gly Ile Glu Cys Gly
                165                 170                 175 gct cta tct ggt gct aac ttg gcc cca gaa gtc gcc aag gaa cac tgg    576
Ala Leu Ser Gly Ala Asn Leu Ala Pro Glu Val Ala Lys Glu His Trp
            180                 185                 190 tcc gag acc acc gtc gct tac cac atc cca gac gac ttc aag ggt gac    624
Ser Glu Thr Thr Val Ala Tyr His Ile Pro Asp Asp Phe Lys Gly Asp
        195                 200                 205 ggt aag gac atc gac cac cgt gtc ttg aag cag ttg ttc cac aga cca    672
Gly Lys Asp Ile Asp His Arg Val Leu Lys Gln Leu Phe His Arg Pro
    210                 215                 220 tac ttc cac gtg aat gtg att gac gat gtt gct ggt atc tcc atc gca    720
Tyr Phe His Val Asn Val Ile Asp Asp Val Ala Gly Ile Ser Ile Ala
225                 230                 235                 240 ggt gca ttg aag aac gtg gtc gcc ttg ggt tgc ggt ttc gtt acc ggt    768
Gly Ala Leu Lys Asn Val Val Ala Leu Gly Cys Gly Phe Val Thr Gly
                245                 250                 255 cta ggt tgg ggt aac aac gcc gcc gcc atc caa cgt gtc ggt ttg        816
Leu Gly Trp Gly Asn Asn Ala Ala Ala Ile Gln Arg Val Gly Leu
            260                 265                 270 ggt gaa atc atc aag ttc ggt agg atg ttc ttc cca gaa tcc aag gtg    864
Gly Glu Ile Ile Lys Phe Gly Arg Met Phe Phe Pro Glu Ser Lys Val
        275                 280                 285 gag act tac tac caa gaa tcc gca ggt gtt gct gac ttg atc acc acc    912
Glu Thr Tyr Tyr Gln Glu Ser Ala Gly Val Ala Asp Leu Ile Thr Thr
    290                 295                 300 tgt tcc ggt ggt aga aac gtc cgt gtt gcc acc gaa atg gcc aag act    960
Cys Ser Gly Gly Arg Asn Val Arg Val Ala Thr Glu Met Ala Lys Thr
305                 310                 315                 320 ggt aag agc ggt gag caa gtc gaa aaa gac atc ttg aac ggt caa tcc    1008
Gly Lys Ser Gly Glu Gln Val Glu Lys Asp Ile Leu Asn Gly Gln Ser
                325                 330                 335 gct caa ggt ttg gtc acc tgt aag gaa gtt cac cag tgg tta gaa tct    1056
Ala Gln Gly Leu Val Thr Cys Lys Glu Val His Gln Trp Leu Glu Ser
            340                 345                 350 agt gga aac acc gaa gac ttc cca ttg ttc gag gct gtc tac cag atc    1104
Ser Gly Asn Thr Glu Asp Phe Pro Leu Phe Glu Ala Val Tyr Gln Ile
        355                 360                 365 act tac gaa aac gtg ccc atg aag gag ttg cca tct atg atc gaa gaa    1152
Thr Tyr Glu Asn Val Pro Met Lys Glu Leu Pro Ser Met Ile Glu Glu
    370                 375                 380 ttg gat atc gat agc aca tcg aag tgc gta ttg agt tac aag atg ggt    1200
Leu Asp Ile Asp Ser Thr Ser Lys Cys Val Leu Ser Tyr Lys Met Gly
385                 390                 395                 400 ctc tag                                                            1206
Leu

<210> SEQ ID NO 14
<211> LENGTH: 401
<212> TYPE: PRT
<213> ORGANISM: Zygosaccharomyces rouxii

<400> SEQUENCE: 14

Met Ala Ala Thr Asp Arg Leu Asn Gln Thr Ser Asp Ile Leu Ser Gln
 1               5                  10                  15
```

-continued

Ser Met Lys Lys Thr Asp Ser Ser Met Ser Val Val Thr Ala Glu Asn
             20                  25                  30

Pro Tyr Lys Val Ser Val Gly Ser Gly Asn Trp Gly Thr Thr Ile
         35                  40                  45

Ala Lys Val Val Ala Glu Asn Thr Lys Glu Lys Pro Glu Leu Phe Gln
     50                  55                  60

Glu Arg Val Asp Met Trp Val Phe Glu Glu Gln Ile Asp Gly Thr Pro
 65                  70                  75                  80

Leu Ala Gln Ile Ile Asn Thr Lys His Gln Asn Val Lys Tyr Leu Pro
                 85                  90                  95

Asn Ile Asp Leu Pro Asp Asn Leu Val Ala Asn Pro Asp Leu Ile Ala
                100                 105                 110

Thr Thr Lys Asp Ala Asp Val Ile Val Phe Asn Val Pro His Gln Phe
             115                 120                 125

Leu Gly Arg Ile Val Ala Gln Met Lys Gly Gln Ile Lys Pro Thr Ala
         130                 135                 140

Arg Ala Val Ser Cys Leu Lys Gly Phe Glu Val Gly Pro Lys Gly Val
145                 150                 155                 160

Gln Leu Leu Ser Asp Tyr Val Thr Gln Glu Leu Gly Ile Glu Cys Gly
                165                 170                 175

Ala Leu Ser Gly Ala Asn Leu Ala Pro Glu Val Ala Lys Glu His Trp
            180                 185                 190

Ser Glu Thr Thr Val Ala Tyr His Ile Pro Asp Asp Phe Lys Gly Asp
        195                 200                 205

Gly Lys Asp Ile Asp His Arg Val Leu Lys Gln Leu Phe His Arg Pro
    210                 215                 220

Tyr Phe His Val Asn Val Ile Asp Asp Val Ala Gly Ile Ser Ile Ala
225                 230                 235                 240

Gly Ala Leu Lys Asn Val Val Ala Leu Gly Cys Gly Phe Val Thr Gly
                245                 250                 255

Leu Gly Trp Gly Asn Asn Ala Ala Ala Ala Ile Gln Arg Val Gly Leu
            260                 265                 270

Gly Glu Ile Ile Lys Phe Gly Arg Met Phe Phe Pro Glu Ser Lys Val
        275                 280                 285

Glu Thr Tyr Tyr Gln Glu Ser Ala Gly Val Ala Asp Leu Ile Thr Thr
    290                 295                 300

Cys Ser Gly Gly Arg Asn Val Arg Val Ala Thr Glu Met Ala Lys Thr
305                 310                 315                 320

Gly Lys Ser Gly Glu Gln Val Glu Lys Asp Ile Leu Asn Gly Gln Ser
                325                 330                 335

Ala Gln Gly Leu Val Thr Cys Lys Glu Val His Gln Trp Leu Glu Ser
            340                 345                 350

Ser Gly Asn Thr Glu Asp Phe Pro Leu Phe Glu Ala Val Tyr Gln Ile
        355                 360                 365

Thr Tyr Glu Asn Val Pro Met Lys Glu Leu Pro Ser Met Ile Glu Glu
    370                 375                 380

Leu Asp Ile Asp Ser Thr Ser Lys Cys Val Leu Ser Tyr Lys Met Gly
385                 390                 395                 400

Leu

<210> SEQ ID NO 15
<211> LENGTH: 1170
<212> TYPE: DNA

<213> ORGANISM: Zygosaccharomyces rouxii
<220> FEATURE:
<221> NAME/KEY: CDS
<222> LOCATION: (1)..(1167)
<223> OTHER INFORMATION: coding for G3PDH

<400> SEQUENCE: 15

| | | | | | | | | | | | | | | | | |
|---|---|---|---|---|---|---|---|---|---|---|---|---|---|---|---|---|
| atg | gcc | gcc | act | gac | aga | tta | aac | caa | acc | tcc | gat | atc | cta | tct | cat | 48 |
| Met | Ala | Ala | Thr | Asp | Arg | Leu | Asn | Gln | Thr | Ser | Asp | Ile | Leu | Ser | His | |
| 1 | | | | 5 | | | | | 10 | | | | | 15 | | |
| tct | atg | aag | aag | act | gat | acc | tca | atg | tca | att | gtt | acc | gct | gag | aat | 96 |
| Ser | Met | Lys | Lys | Thr | Asp | Thr | Ser | Met | Ser | Ile | Val | Thr | Ala | Glu | Asn | |
| | | | 20 | | | | | 25 | | | | | 30 | | | |
| cct | tac | aag | gtc | gct | gtt | gtc | ggt | tct | ggt | aac | tgg | ggt | acc | act | atc | 144 |
| Pro | Tyr | Lys | Val | Ala | Val | Val | Gly | Ser | Gly | Asn | Trp | Gly | Thr | Thr | Ile | |
| | 35 | | | | | 40 | | | | | 45 | | | | | |
| gct | aag | gtt | gtt | gcc | gaa | aac | acc | aaa | gaa | aag | cca | gag | ttg | ttc | caa | 192 |
| Ala | Lys | Val | Val | Ala | Glu | Asn | Thr | Lys | Glu | Lys | Pro | Glu | Leu | Phe | Gln | |
| 50 | | | | | 55 | | | | | 60 | | | | | | |
| gga | cgt | gtg | gac | atg | tgg | gtt | ttc | gaa | gaa | caa | atc | gat | ggt | act | cca | 240 |
| Gly | Arg | Val | Asp | Met | Trp | Val | Phe | Glu | Glu | Gln | Ile | Asp | Gly | Thr | Pro | |
| 65 | | | | | 70 | | | | | 75 | | | | | 80 | |
| ttg | act | caa | atc | atc | aac | acc | aaa | cac | caa | aac | gtc | aaa | tac | ctt | cca | 288 |
| Leu | Thr | Gln | Ile | Ile | Asn | Thr | Lys | His | Gln | Asn | Val | Lys | Tyr | Leu | Pro | |
| | | | | 85 | | | | | 90 | | | | | 95 | | |
| aac | atc | gat | ctt | ccg | ggg | aat | ttg | gtc | gct | aac | cca | gat | ttg | atc | tct | 336 |
| Asn | Ile | Asp | Leu | Pro | Gly | Asn | Leu | Val | Ala | Asn | Pro | Asp | Leu | Ile | Ser | |
| | | | 100 | | | | | 105 | | | | | 110 | | | |
| act | acc | aag | gac | gct | gat | gtc | atc | gtt | ttc | aac | gtt | cct | cac | caa | ttt | 384 |
| Thr | Thr | Lys | Asp | Ala | Asp | Val | Ile | Val | Phe | Asn | Val | Pro | His | Gln | Phe | |
| | | 115 | | | | | 120 | | | | | 125 | | | | |
| ttg | ggc | cgt | atc | gtt | tct | caa | atg | aag | ggt | caa | atc | aaa | cca | gat | gct | 432 |
| Leu | Gly | Arg | Ile | Val | Ser | Gln | Met | Lys | Gly | Gln | Ile | Lys | Pro | Asp | Ala | |
| | 130 | | | | | 135 | | | | | 140 | | | | | |
| cgt | gcc | atc | tcc | tgt | cta | aag | ggt | ttc | gaa | gtt | ggt | cca | aag | ggt | gtc | 480 |
| Arg | Ala | Ile | Ser | Cys | Leu | Lys | Gly | Phe | Glu | Val | Gly | Pro | Lys | Gly | Val | |
| 145 | | | | | 150 | | | | | 155 | | | | | 160 | |
| caa | cta | ctt | tct | gac | tac | gtc | act | caa | gaa | tta | ggt | atc | caa | tgt | ggt | 528 |
| Gln | Leu | Leu | Ser | Asp | Tyr | Val | Thr | Gln | Glu | Leu | Gly | Ile | Gln | Cys | Gly | |
| | | | | 165 | | | | | 170 | | | | | 175 | | |
| gcc | cta | tct | ggt | gct | aac | ttg | gct | cca | gaa | gtc | gcc | aag | gaa | cac | tgg | 576 |
| Ala | Leu | Ser | Gly | Ala | Asn | Leu | Ala | Pro | Glu | Val | Ala | Lys | Glu | His | Trp | |
| | | | 180 | | | | | 185 | | | | | 190 | | | |
| tcc | gaa | act | acc | gtc | gct | tac | caa | gtc | cca | gat | gac | ttc | aag | ggt | gaa | 624 |
| Ser | Glu | Thr | Thr | Val | Ala | Tyr | Gln | Val | Pro | Asp | Asp | Phe | Lys | Gly | Glu | |
| | | 195 | | | | | 200 | | | | | 205 | | | | |
| ggt | aaa | gat | atc | gac | cac | cgt | gtc | ttg | aaa | caa | ttg | ttc | cac | aga | cca | 672 |
| Gly | Lys | Asp | Ile | Asp | His | Arg | Val | Leu | Lys | Gln | Leu | Phe | His | Arg | Pro | |
| | 210 | | | | | 215 | | | | | 220 | | | | | |
| tac | ttc | cac | gtc | aat | gtg | atc | gac | gat | gtt | gct | ggt | att | tct | atc | gca | 720 |
| Tyr | Phe | His | Val | Asn | Val | Ile | Asp | Asp | Val | Ala | Gly | Ile | Ser | Ile | Ala | |
| 225 | | | | | 230 | | | | | 235 | | | | | 240 | |
| ggt | gca | ttg | aag | aac | gtg | gtt | gcc | ttg | ggt | tgc | ggt | ttc | gtc | acc | ggt | 768 |
| Gly | Ala | Leu | Lys | Asn | Val | Val | Ala | Leu | Gly | Cys | Gly | Phe | Val | Thr | Gly | |
| | | | | 245 | | | | | 250 | | | | | 255 | | |
| cta | ggc | tgg | ggt | aac | aac | gct | gcc | gcc | gcc | atc | caa | cgt | gtt | ggt | ttg | 816 |
| Leu | Gly | Trp | Gly | Asn | Asn | Ala | Ala | Ala | Ala | Ile | Gln | Arg | Val | Gly | Leu | |
| | | | 260 | | | | | 265 | | | | | 270 | | | |
| ggt | gaa | atc | atc | aag | ttc | ggt | aga | atg | ttc | ttc | cca | gaa | tcc | aag | gtg | 864 |
| Gly | Glu | Ile | Ile | Lys | Phe | Gly | Arg | Met | Phe | Phe | Pro | Glu | Ser | Lys | Val | |
| | 275 | | | | | 280 | | | | | 285 | | | | | |

```
gaa act tac tac caa gaa tct gca ggt gtt gct gat ttg atc act acc         912
Glu Thr Tyr Tyr Gln Glu Ser Ala Gly Val Ala Asp Leu Ile Thr Thr
    290                 295                 300 tgt tcc ggt ggt aga aac gtt cgt gtc gcc act gaa atg gcc aag act         960
Cys Ser Gly Gly Arg Asn Val Arg Val Ala Thr Glu Met Ala Lys Thr
305                 310                 315                 320 ggt aag agc ggt gaa caa gtc gaa aag gac atc ttg aac ggt caa tcc        1008
Gly Lys Ser Gly Glu Gln Val Glu Lys Asp Ile Leu Asn Gly Gln Ser
                325                 330                 335 gct caa ggt ttg att act gct aag gaa gtc cac caa tgg ttg gaa tcc        1056
Ala Gln Gly Leu Ile Thr Ala Lys Glu Val His Gln Trp Leu Glu Ser
            340                 345                 350 agc ggt cac acc gaa gaa tac cca ttg ttt gaa gcc gtc tac caa atc        1104
Ser Gly His Thr Glu Glu Tyr Pro Leu Phe Glu Ala Val Tyr Gln Ile
        355                 360                 365 act tac gaa aac gtg ccc atg aag gag ttg cca tcc atg atc gaa gaa        1152
Thr Tyr Glu Asn Val Pro Met Lys Glu Leu Pro Ser Met Ile Glu Glu
370                 375                 380 ttg gat atc gta gaa taa                                                 1170
Leu Asp Ile Val Glu
385
```

<210> SEQ ID NO 16
<211> LENGTH: 389
<212> TYPE: PRT
<213> ORGANISM: Zygosaccharomyces rouxii

<400> SEQUENCE: 16

```
Met Ala Ala Thr Asp Arg Leu Asn Gln Thr Ser Asp Ile Leu Ser His
1               5                   10                  15

Ser Met Lys Lys Thr Asp Thr Ser Met Ser Ile Val Thr Ala Glu Asn
                20                  25                  30

Pro Tyr Lys Val Ala Val Val Gly Ser Gly Asn Trp Gly Thr Thr Ile
            35                  40                  45

Ala Lys Val Val Ala Glu Asn Thr Lys Glu Lys Pro Glu Leu Phe Gln
        50                  55                  60

Gly Arg Val Asp Met Trp Val Phe Glu Glu Gln Ile Asp Gly Thr Pro
65                  70                  75                  80

Leu Thr Gln Ile Ile Asn Thr Lys His Gln Asn Val Lys Tyr Leu Pro
                85                  90                  95

Asn Ile Asp Leu Pro Gly Asn Leu Val Ala Asn Pro Asp Leu Ile Ser
            100                 105                 110

Thr Thr Lys Asp Ala Asp Val Ile Val Phe Asn Val Pro His Gln Phe
        115                 120                 125

Leu Gly Arg Ile Val Ser Gln Met Lys Gly Gln Ile Lys Pro Asp Ala
    130                 135                 140

Arg Ala Ile Ser Cys Leu Lys Gly Phe Glu Val Gly Pro Lys Gly Val
145                 150                 155                 160

Gln Leu Leu Ser Asp Tyr Val Thr Gln Glu Leu Gly Ile Gln Cys Gly
                165                 170                 175

Ala Leu Ser Gly Ala Asn Leu Ala Pro Glu Val Ala Lys Glu His Trp
            180                 185                 190

Ser Glu Thr Thr Val Ala Tyr Gln Val Pro Asp Asp Phe Lys Gly Glu
        195                 200                 205

Gly Lys Asp Ile Asp His Arg Val Leu Lys Gln Leu Phe His Arg Pro
    210                 215                 220
```

-continued

```
Tyr Phe His Val Asn Val Ile Asp Asp Val Ala Gly Ile Ser Ile Ala
225                 230                 235                 240

Gly Ala Leu Lys Asn Val Val Ala Leu Gly Cys Gly Phe Val Thr Gly
            245                 250                 255

Leu Gly Trp Gly Asn Asn Ala Ala Ala Ile Gln Arg Val Gly Leu
        260                 265                 270

Gly Glu Ile Ile Lys Phe Gly Arg Met Phe Phe Pro Glu Ser Lys Val
    275                 280                 285

Glu Thr Tyr Tyr Gln Glu Ser Ala Gly Val Ala Asp Leu Ile Thr Thr
    290                 295                 300

Cys Ser Gly Gly Arg Asn Val Arg Val Ala Thr Glu Met Ala Lys Thr
305                 310                 315                 320

Gly Lys Ser Gly Glu Gln Val Glu Lys Asp Ile Leu Asn Gly Gln Ser
            325                 330                 335

Ala Gln Gly Leu Ile Thr Ala Lys Glu Val His Gln Trp Leu Glu Ser
        340                 345                 350

Ser Gly His Thr Glu Glu Tyr Pro Leu Phe Glu Ala Val Tyr Gln Ile
    355                 360                 365

Thr Tyr Glu Asn Val Pro Met Lys Glu Leu Pro Ser Met Ile Glu Glu
    370                 375                 380

Leu Asp Ile Val Glu
385

<210> SEQ ID NO 17
<211> LENGTH: 8809
<212> TYPE: DNA
<213> ORGANISM: Artificial Sequence
<220> FEATURE:
<223> OTHER INFORMATION: Description of artificial sequence: expression
      vector pSUN-USP containing Saccharomyces G3PDH
<220> FEATURE:
<221> NAME/KEY: misc_feature
<222> LOCATION: (1017)..(2189)
<223> OTHER INFORMATION: coding for G3PDH

<400> SEQUENCE: 17
aatattcaaa caaacacata cagcgcgact tatcatggac atacaaatgg acgaacggat      60 aaacctttc acgccctttt aaatatccga ttattctaat aaacgctctt ttctcttagg     120
tttacccgcc aatatatcct gtcaaacact gatagtttaa actgaaggcg ggaaacgaca    180
atcagatcta gtaggaaaca gctatgacca tgattacgcc aagcttgcat gcctgcaggt    240
cgactctaga ctagtggatc cgatatcgcc cgggctcgag gtaccgagct cgaattcggc    300
gcgccgagct cctcgagcaa atttacacat tgccactaaa cgtctaaacc cttgtaattt    360 gttttttgttt tactatgtgt gttatgtatt tgatttgcga taaattttta tatttggtac    420
taaatttata acacctttta tgctaacgtt tgccaacact tagcaatttg caagttgatt    480
aattgattct aaattatttt tgtcttctaa atacatatac taatcaactg gaaatgtaaa    540
tatttgctaa tatttctact ataggagaat taaagtgagt gaatatggta ccacaaggtt    600
tggagattta attgttgcaa tgatgcatgg atggcatata caccaaacat tcaataattc    660
ttgaggataa taatggtacc acacaagatt tgaggtgcat gaacgtcacg tggacaaaag    720
gtttagtaat ttttcaagac aacaatgtta ccacacacaa gttttgaggt gcatgcatgg    780
atgccctgtg gaaagtttaa aaatattttg gaaatgattt gcatggaagc catgtgtaaa    840
accatgacat ccacttggag gatgcaataa tgaagaaaac tacaaatta catgcaacta    900 gttatgcatg tagtctatat aatgaggatt ttgcaatact ttcattcata cacactcact    960
```

```
aagttttaca cgattataat ttcttcatag ccagcccacc gcggtgggcg gccgccatgt   1020
ctgctgctgc tgatagatta aacttaactt ccggccactt gaatgctggt agaaagagaa   1080
gttcctcttc tgtttctttg aaggctgccg aaaagccttt caaggttact gtgattggat   1140
ctggtaactg gggtactact attgccaagg tggttgccga aaattgtaag ggatacccag   1200
aagttttcgc tccaatagta caaatgtggg tgttcgaaga agagatcaat ggtgaaaaat   1260
tgactgaaat cataaatact agacatcaaa cgtgaaaata cttgcctggc atcactctac   1320
ccgacaattt ggttgctaat ccagacttga ttgattcagt caaggatgtc gacatcatcg   1380
tcttcaacat tccacatcaa tttttgcccc gtatctgtag ccaattgaaa ggtcatgttg   1440
attcacacgt cagagctatc tcctgtctaa agggttttga agttggtgct aaaggtgtcc   1500
aattgctatc ctcttacatc actgaggaac taggtattca atgtggtgct ctatctggtg   1560
ctaacattgc cactgaagtc gctcaagaac actggtctga acaacagtt gcttaccaca   1620 ttccaaagga tttcagaggc gagggcaagg acgtcgacca taaggttcta aaggccttgt   1680
tccacagacc ttacttccac gttagtgtca tcgaagatgt tgctggtatc tccatctgtg   1740
gtgctttgaa gaacgttgtt gccttaggtt gtggtttcgt cgaaggtcta ggctggggta   1800
acaacgcttc tgctgccatc caaagagtcg gtttgggtga gatcatcaga ttcggtcaaa   1860 tgttttttccc agaatctaga gaagaaacat actaccaaga gtctgctggt gttgctgatt   1920
tgatcaccac ctgcgctggt ggtagaaacg tcaaggttgc taggctaatg gctacttctg   1980
gtaaggacgc ctgggaatgt gaaaaggagt tgttgaatgg ccaatccgct caaggtttaa   2040
ttacctgcaa agaagttcac gaatggttgg aaacatgtgg ctctgtcgaa gacttcccat   2100
tatttgaagc cgtataccaa atcgtttaca acaactaccc aatgaagaac ctgccggaca   2160
tgattgaaga attagatcta catgaagatt aggcggccgc ctgcagtcta gaaggcctcc   2220
tgctttaatg agatatgcga gacgcctatg atcgcatgat atttgctttc aattctgttg   2280
tgcacgttgt aaaaaacctg agcatgtgta gctcagatcc ttaccgccgg tttcggttca   2340
ttctaatgaa tatatcaccc gttactatcg tattttatg aataatattc ccgttcaat   2400 ttactgattg tccgtcgacg aattcactgg ccgtcgtttt acaacgactc agagcttgac   2460
aggaggcccg atctagtaac atagatgaca ccgcgcgcga taatttatcc tagttttgcgc   2520 gctatatttt gttttctatc gcgtattaaa tgtataattg cgggactcta atcataaaaa   2580
cccatctcat aaataacgtc atgcattaca tgttaattat tacatgctta acgtaattca   2640
acagaaatta tatgataatc atcgcaagac cggcaacagg attcaatctt aagaaacttt   2700
attgccaaat gtttgaacga tcggggatca tccgggtctg tggcgggaac tccacgaaaa   2760
tatccgaacg cagcaagatc tagagcttgg gtcccgctca aagaactcg tcaagaaggc   2820 gatagaaggc gatgcgctgc gaatcgggag cggcgatacc gtaaagcacg aggaagcggt   2880
cagcccattc gccgccaagc tcttcagcaa tatcacgggt agccaacgct atgtcctgat   2940
agcggtccgc cacacccagc cggccacagt cgatgaatcc agaaaagcgg ccattttcca   3000
ccatgatatt cggcaagcag gcatcgccat gtgtcacgac gagatcctcg ccgtcgggca   3060
tgcgcgcctt gagcctggcg aacagttcgg ctggcgcgag cccctgatgc tcttcgtcca   3120
gatcatcctg atcgacaaga ccggcttcca tccgagtacg tgctcgctcg atgcgatgtt   3180
tcgcttggtg gtcgaatggg caggtagccg atcaagcgt atgcagccgc cgcattgcat   3240
cagccatgat ggatactttc tcggcaggag caaggtgaga tgacaggaga tcctgccccg   3300
```

```
gcacttcgcc caatagcagc cagtcccttc ccgcttcagt gacaacgtcg agcacagctg    3360
cgcaaggaac gcccgtcgtg gccagccacg atagccgcgc tgcctcgtcc tgcagttcat    3420
tcagggcacc ggacaggtcg gtcttgacaa aaagaaccgg gcgcccctgc gctgacagcc    3480
ggaacacggc ggcatcagag cagccgattg tctgttgtgc ccagtcatag ccgaatagcc    3540
tctccaccca agcggccgga gaacctgcgt gcaatccatc ttgttcaatc atgcgaaacg    3600
atccagatcc ggtgcagatt atttggattg agagtgaata tgagactcta attggatacc    3660
gaggggaatt tatggaacgt cagtggagca tttttgacaa gaaatatttg ctagctgata    3720
gtgaccttag gcgacttttg aacgcgcaat aatggtttct gacgtatgtg cttagctcat    3780
taaactccag aaacccgcgg ctgagtggct ccttcaacgt tgcggttctg tcagttccaa    3840
acgtaaaacg gcttgtcccg cgtcatcggc ggggtcata acgtgactcc cttaattctc    3900
cgctcatgat cagattgtcg tttcccgcct tcagtttaaa ctatcagtgt ttgacaggat    3960
cactgcttgg taataattgt cattagattg tttttatgca tagatgcact cgaaatcagc    4020
caattttaga caagtatcaa acggatgtta attcagtaca ttaaagacgt ccgcaatgtg    4080
ttattaagtt gtctaagcgt caatttgttt acaccacaat atatcctgcc accagccagc    4140
caacagctcc ccgaccggca gctcggcaca aaatcaccac gcgtctaaaa aggtgatgtg    4200
tatttgagta aaacagcttg cgtcatgcgg tcgctgcgta tatgatgcga tgagtaaata    4260
aacaaatacg caaggggaac gcatgaaggt tatcgctgta cttaaccaga aaggcgggtc    4320
aggcaagacg accatcgcaa cccatctagc ccgcgccctg caactcgccg gggccgatgt    4380
tctgttagtc gattccgatc cccagggcag tgcccgcgat tgggcggccg tgcgggaaga    4440
tcaaccgcta accgttgtcg gcatcgaccg cccgacgatt gaccgcgacg tgaaggccat    4500
cggccggcgc gacttcgtag tgatcgacgg agcgccccag gcggcggact tggctgtgtc    4560
cgcgatcaag gcagccgact tcgtgctgat tccggtgcag ccaagcccct tacgacatatg    4620 ggccaccgcc gacctggtgg agctggttaa gcagcgcatt gaggtcacgg atggaaggct    4680
acaagcggcc tttgtcgtgt cgcgggcgat caaaggcacg cgcatcggcg gtgaggttgc    4740
cgaggcgctg gccgggtacg agctgcccat tcttgagtcc cgtatcacgc agcgcgtgag    4800
ctacccaggc actgccgccg ccggcacaac cgttcttgaa tcagaacccg agggcgacgc    4860
tgcccgcgag gtccaggcgc tggccgctga aattaaatca aaactcattt gagttaatga    4920
ggtaaagaga aaatgagcaa aagcacaaac acgctaagtg ccggccgtcc gagcgcacgc    4980
agcagcaagg ctgcaacgtt ggccagcctg gcagacacgc cagccatgaa gcgggtcaac    5040
tttcagttgc cggcggagga tcacaccaag ctgaagatgt acgcggtacg ccaaggcaag    5100
accattaccg agctgctatc tgaatacatc gcgcagctac cagagtaaat gagcaaatga    5160
ataaatgagt agatgaattt tagcggctaa aggaggcggc atggaaaatc aagaacaacc    5220
aggcaccgac gccgtggaat gccccatgtg tggaggaacg ggcggttggc caggcgtaag    5280
cggctgggtt gtctgccggc cctgcaatgg cactggaacc cccaagcccg aggaatcggc    5340
gtgagcggtc gcaaaccatc cggcccggta caaatcggcg cggcgctggg tgatgacctg    5400
gtggagaagt tgaaggccgc gcaggccgcc cagcggcaac gcatcgaggc agaagacgcc    5460
ccggtgaatc gtggcaaggg gccgctgatc gaatccgcaa agaatcccgg caaccgccgg    5520
cagccggtgc gccgtcgatt aggaagccgc ccaagggcga cgagcaacca gattttttcg    5580
ttccgatgct ctatgacgtg gcacccgcgc atagtcgcag catcatggac gtggccgttt    5640
tccgtctgtc gaagcgtgac cgacgagctg gcgaggtgat ccgctacgag cttccagacg    5700
```

```
ggcacgtaga ggtttccgca gggccggccg gcatggccag tgtgtgggat tacgacctgg   5760
tactgatggc ggtttcccat ctaaccgaat ccatgaaccg ataccgggaa gggaagggag   5820
acaagcccgg ccgcgtgttc cgtccacacg ttgcggacgt actcaagttc tgccggcgag   5880
ccgatggcgg aaagcagaaa gacgacctgg tagaaacctg cattcggtta aacaccacgc   5940
acgttgccat gcagcgtacg aagaaggcca agaacggccg cctggtgacg gtatccgagg   6000
gtgaagcctt gattagccgc tacaagatcg taaagagcga aaccgggcgg ccggagtaca   6060
tcgagatcga gctagctgat tggatgtacc gcgagatcac agaaggcaag aacccggacg   6120
tgctgacggt tcaccccgat tacttttga tcgatcccgg catcggccgt tttctctacc    6180
gcctggcacg ccgcgccgca ggcaaggcag aagccagatg gttgttcaag acgatctacg   6240
aacgcagtgg cagcgccgga gagttcaaga agttctgttt caccgtgcgc aagctgatcg   6300
ggtcaaatga cctgccggag tacgatttga aggaggaggc ggggcaggct ggcccgatcc   6360
tagtcatgcg ctaccgcaac ctgatcgagg gcgaagcatc cgccggttcc taatgtacgg   6420
agcagatgct agggcaaatt gccctagcag gggaaaaagg tcgaaaaggt ctctttcctg   6480
tggatagcac gtacattggg aacccaaagc cgtacattgg gaaccggaac ccgtacattg   6540
ggaacccaaa gccgtacatt gggaaccggt cacacatgta agtgactgat ataaaagaga   6600
aaaaaggcga ttttccgcc taaaactctt taaaacttat taaaactctt aaaacccgcc   6660
tggcctgtgc ataactgtct ggccagcgca cagccgaaga gctgcaaaaa gcgcctaccc   6720
ttcggtcgct gcgctcccta cgcccgccg cttcgcgtcg gcctatcgcg gcctatgcgg    6780
tgtgaaatac cgcacagatg cgtaaggaga aaataccgca tcaggcgctc ttccgcttcc   6840
tcgctcactg actcgctgcg ctcggtcgtt cggctgcggc gagcggtatc agctcactca   6900
aaggcggtaa tacggttatc cacagaatca ggggataacg caggaaagaa catgtgagca   6960
aaaggccagc aaaaggccag gaaccgtaaa aaggccgcgt tgctggcgtt tttccatagg   7020
ctccgccccc ctgacgagca tcacaaaaat cgacgctcaa gtcagaggtg gcgaaacccg   7080
acaggactat aaagatacca ggcgtttccc cctggaagct ccctcgtgcg ctctcctgtt   7140
ccgaccctgc cgcttaccgg atacctgtcc gcctttctcc cttcgggaag cgtggcgctt   7200
tctcatagct cacgctgtag gtatctcagt tcggtgtagg tcgttcgctc caagctgggc   7260
tgtgtgcacg aaccccccgt tcagcccgac cgctgcgcct tatccggtaa ctatcgtctt   7320
gagtccaacc cggtaagaca cgacttatcg ccactggcag cagccactgg taacaggatt   7380
agcagagcga ggtatgtagg cggtgctaca gagttcttga agtggtggcc taactacggc   7440
tacactagaa ggacagtatt tggtatctgc gctctgctga agccagttac cttcggaaaa   7500
agagttggta gctcttgatc cggcaaacaa accaccgctg gtagcggtgg ttttttgtt    7560 tgcaagcagc agattacgcg cagaaaaaa ggatctcaag aagatccttt gatcttttct    7620
acggggtctg acgctcagtg gaacgaaaac tcacgttaag ggattttggt catgcatgat   7680
atatctccca atttgtgtag gcttattat gcacgcttaa aaataataaa agcagacttg    7740
acctgatagt ttggctgtga gcaattatgt gcttagtgca tctaacgctt gagttaagcc   7800
gcgccgcgaa gcggcgtcgg cttgaacgaa tttctagcta gacattattt gccgactacc   7860
ttggtgatct cgcctttcac gtagtggaca aattcttcca actgatctgc gcgcgaggcc   7920
aagcgatctt cttcttgtcc aagataagcc tgtctagctt caagtatgac gggctgatac   7980
tgggccggca ggcgctccat tgcccagtcg gcagcgacat ccttcggcgc gattttgccg   8040
```

-continued

```
gttactgcgc tgtaccaaat gcgggacaac gtaagcacta catttcgctc atcgccagcc      8100
cagtcgggcg gcgagttcca tagcgttaag gtttcattta gcgcctcaaa tagatcctgt      8160
tcaggaaccg gatcaaagag ttcctccgcc gctggaccta ccaaggcaac gctatgttct      8220
cttgcttttg tcagcaagat agccagatca atgtcgatcg tggctggctc gaagatacct      8280
gcaagaatgt cattgcgctg ccattctcca aattgcagtt cgcgcttagc tggataacgc      8340
cacggaatga tgtcgtcgtg cacaacaatg gtgacttcta cagcgcggag aatctcgctc      8400
tctccagggg aagccgaagt ttccaaaagg tcgttgatca agctcgccg cgttgtttca       8460 tcaagcctta cggtcaccgt aaccagcaaa tcaatatcac tgtgtggctt caggccgcca     8520
tccactgcgg agccgtacaa atgtacggcc agcaacgtcg gttcgagatg gcgctcgatg     8580
acgccaacta cctctgatag ttgagtcgat acttcggcga tcaccgcttc ccccatgatg     8640
tttaactttg ttttagggcg actgccctgc tgcgtaacat cgttgctgct ccataacatc     8700
aaacatcgac ccacggcgta acgcgcttgc tgcttggatg cccgaggcat agactgtacc     8760
ccaaaaaaac agtcataaca agccatgaaa accgccactg cgttccatg               8809
```

<210> SEQ ID NO 18  
<211> LENGTH: 26  
<212> TYPE: DNA  
<213> ORGANISM: Artificial Sequence  
<220> FEATURE:  
<223> OTHER INFORMATION: Description of the artificial sequence: oligonucleotide primer

<400> SEQUENCE: 18
actagtatgt ctgctgctgc tgatag                                           26

<210> SEQ ID NO 19  
<211> LENGTH: 26  
<212> TYPE: DNA  
<213> ORGANISM: Artificial Sequence  
<220> FEATURE:  
<223> OTHER INFORMATION: Description of the Artificial Sequence: oligonucleotide primer

<400> SEQUENCE: 19
ctcgagatct tcatgtagat ctaatt                                           26

<210> SEQ ID NO 20  
<211> LENGTH: 29  
<212> TYPE: DNA  
<213> ORGANISM: Artificial Sequence  
<220> FEATURE:  
<223> OTHER INFORMATION: Description of the Artificial Sequence: oligonucleotide primer

<400> SEQUENCE: 20
gcggccgcca tgtctgctgc tgctgatag                                        29

<210> SEQ ID NO 21  
<211> LENGTH: 28  
<212> TYPE: DNA  
<213> ORGANISM: Artificial Sequence  
<220> FEATURE:  
<223> OTHER INFORMATION: Description of the Artificial Sequence: oligonucleotide primer

<400> SEQUENCE: 21
gcggccgcat cttcatgtag atctaatt                                         28

```
<210> SEQ ID NO 22
<211> LENGTH: 11
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (8)
<223> OTHER INFORMATION: Thr

<400> SEQUENCE: 22

Gly Ser Gly Asn Trp Gly Thr Ala Ile Ala Lys
 1               5                  10

<210> SEQ ID NO 23
<211> LENGTH: 8
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (2)
<223> OTHER INFORMATION: Gln

<400> SEQUENCE: 23

His Glu Gln Asn Val Lys Tyr Leu
 1               5

<210> SEQ ID NO 24
<211> LENGTH: 12
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (1)
<223> OTHER INFORMATION: Asn
<220> FEATURE:
<221> NAME/KEY: VARIANT
<222> LOCATION: (2)
<223> OTHER INFORMATION: Val
<220> FEATURE:
<221> NAME/KEY: VARIANT
<222> LOCATION: (3)
<223> OTHER INFORMATION: Ile
<220> FEATURE:
<221> NAME/KEY: VARIANT
<222> LOCATION: (5)
<223> OTHER INFORMATION: Trp
<220> FEATURE:
<221> NAME/KEY: VARIANT
<222> LOCATION: (6)
<223> OTHER INFORMATION: Asn
<220> FEATURE:
<221> NAME/KEY: VARIANT
<222> LOCATION: (7)
<223> OTHER INFORMATION: Ile or Val
<220> FEATURE:
<221> NAME/KEY: VARIANT
<222> LOCATION: (12)
<223> OTHER INFORMATION: Leu or Ile

<400> SEQUENCE: 24

Asp Ile Leu Val Phe Val Leu Pro His Gln Phe Val
 1               5                  10

<210> SEQ ID NO 25
```

```
<211> LENGTH: 7
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (1)
<223> OTHER INFORMATION: Gly
<220> FEATURE:
<221> NAME/KEY: VARIANT
<222> LOCATION: (2)
<223> OTHER INFORMATION: Val
<220> FEATURE:
<221> NAME/KEY: VARIANT
<222> LOCATION: (5)
<223> OTHER INFORMATION: Ile

<400> SEQUENCE: 25

Ala Ile Ser Cys Leu Lys Gly
 1               5

<210> SEQ ID NO 26
<211> LENGTH: 14
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (3)
<223> OTHER INFORMATION: Ala
<220> FEATURE:
<221> NAME/KEY: VARIANT
<222> LOCATION: (9)
<223> OTHER INFORMATION: Ile or Val
<220> FEATURE:
<221> NAME/KEY: misc_feature
<222> LOCATION: (11)..(11)
<223> OTHER INFORMATION: Xaa is unknown or other
<220> FEATURE:
<221> NAME/KEY: VARIANT
<222> LOCATION: (13)
<223> OTHER INFORMATION: Ile

<400> SEQUENCE: 26

Cys Gly Val Leu Ser Gly Ala Asn Leu Ala Xaa Glu Val Ala
 1               5                  10

<210> SEQ ID NO 27
<211> LENGTH: 9
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (1)
<223> OTHER INFORMATION: Val
<220> FEATURE:
<221> NAME/KEY: misc_feature
<222> LOCATION: (3)..(3)
<223> OTHER INFORMATION: Xaa is unknown or other
<220> FEATURE:
<221> NAME/KEY: misc_feature
<222> LOCATION: (11)..(11)
<223> OTHER INFORMATION: Xaa is unknown or other

<400> SEQUENCE: 27

Leu Phe Xaa Arg Pro Tyr Phe Xaa Val
 1               5
```

```
<210> SEQ ID NO 28
<211> LENGTH: 9
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (2)
<223> OTHER INFORMATION: Met
<220> FEATURE:
<221> NAME/KEY: VARIANT
<222> LOCATION: (3)
<223> OTHER INFORMATION: Gly
<220> FEATURE:
<221> NAME/KEY: VARIANT
<222> LOCATION: (5)
<223> OTHER INFORMATION: Ile
<220> FEATURE:
<221> NAME/KEY: VARIANT
<222> LOCATION: (6)
<223> OTHER INFORMATION: Gln
<220> FEATURE:
<221> NAME/KEY: VARIANT
<222> LOCATION: (7)
<223> OTHER INFORMATION: Lys or Asn
<220> FEATURE:
<221> NAME/KEY: VARIANT
<222> LOCATION: (9)
<223> OTHER INFORMATION: Ser or Ala

<400> SEQUENCE: 28

Gly Leu Leu Glu Met Ile Arg Phe Gly
  1               5

<210> SEQ ID NO 29
<211> LENGTH: 16
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (13)
<223> OTHER INFORMATION: Ile

<400> SEQUENCE: 29

Gly Ser Gly Asn Trp Gly Thr Thr Ile Ala Lys Val Val Ala Glu Asn
  1               5                  10                  15

<210> SEQ ID NO 30
<211> LENGTH: 11
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (3)
<223> OTHER INFORMATION: Arg

<400> SEQUENCE: 30

Asn Thr Lys His Gln Asn Val Lys Tyr Leu Pro
  1               5                  10

<210> SEQ ID NO 31
<211> LENGTH: 12
<212> TYPE: PRT
```

```
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (2)
<223> OTHER INFORMATION: Val
<220> FEATURE:
<221> NAME/KEY: VARIANT
<222> LOCATION: (7)
<223> OTHER INFORMATION: Val

<400> SEQUENCE: 31

Asp Ile Leu Val Phe Asn Ile Pro His Gln Phe Leu
 1               5                  10

<210> SEQ ID NO 32
<211> LENGTH: 10
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (3)
<223> OTHER INFORMATION: Val

<400> SEQUENCE: 32

Arg Ala Ile Ser Cys Leu Lys Gly Phe Glu
 1               5                  10

<210> SEQ ID NO 33
<211> LENGTH: 14
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (11)
<223> OTHER INFORMATION: Thr

<400> SEQUENCE: 33

Cys Gly Ala Leu Ser Gly Ala Asn Leu Ala Pro Glu Val Ala
 1               5                  10

<210> SEQ ID NO 34
<211> LENGTH: 9
<212> TYPE: PRT
<213> ORGANISM: Artificial Sequence
<220> FEATURE:
<223> OTHER INFORMATION: Description of the Artificial Sequence: Yeast
      G3PDH sequence motive

<400> SEQUENCE: 34

Leu Phe His Arg Pro Tyr Phe His Val
 1               5

<210> SEQ ID NO 35
<211> LENGTH: 9
<212> TYPE: PRT
<213> ORGANISM: Artificial Sequence
<220> FEATURE:
<223> OTHER INFORMATION: Description of the Artificial Sequence: Yeast
      G3PDH sequence motive
<220> FEATURE:
<221> NAME/KEY: VARIANT
<222> LOCATION: (7)
```

```
<223> OTHER INFORMATION: Arg

<400> SEQUENCE: 35

Gly Leu Gly Glu Ile Ile Lys Phe Gly
  1               5

<210> SEQ ID NO 36
<211> LENGTH: 13718
<212> TYPE: DNA
<213> ORGANISM: Artificial Sequence
<220> FEATURE:
<223> OTHER INFORMATION: Description of the Artificial Sequence:
      expression vector pGPTV-gpd1
<220> FEATURE:
<221> NAME/KEY: promoter
<222> LOCATION: (10807)..(11951)
<223> OTHER INFORMATION: napin promoter
<220> FEATURE:
<221> NAME/KEY: terminator
<222> LOCATION: (13154)..(13408)
<223> OTHER INFORMATION: nos terminator
<220> FEATURE:
<221> NAME/KEY: misc_feature
<222> LOCATION: (11962)..(13137)
<223> OTHER INFORMATION: coding for yeast G3PDH (gpd1)
<220> FEATURE:
<221> NAME/KEY: misc_feature
<222> LOCATION: (13447)..(13549)
<223> OTHER INFORMATION: n located at 13447, 13457, 13485, 13510, 13514,
      13517 13519, 13523, 13535, 13538-13540, 13549, each n is
      a or c or g or t/u, unknown, or other
<220> FEATURE:
<221> NAME/KEY: misc_feature
<222> LOCATION: (13551)..(13701)
<223> OTHER INFORMATION: n located at 13551, 13560, 13562, 13617, 13660,
      13693, 13701, each n is a or c or g or t/u, unknown, or other

<400> SEQUENCE: 36
gatctggcgc cggccagcga gacgagcaag attggccgcc gcccgaaacg atccgacagc      60
gcgcccagca caggtgcgca ggcaaattgc accaacgcat acagcgccag cagaatgcca     120
tagtgggcgg tgacgtcgtt cgagtgaacc agatcgcgca ggaggcccgg cagcaccggc     180
ataatcaggc cgatgccgac agcgtcgagc gcgacagtgc tcagaattac gatcaggggt     240 atgtttgggtt tcacgtctgg cctccggacc agcctccgct ggtccgattg aacgcgcgga     300
ttctttatca ctgataagtt ggtggacata ttatgtttat cagtgataaa gtgtcaagca     360
tgacaaagtt gcagccgaat acagtgatcc gtgccgccct ggacctgttg aacgaggtcg     420
gcgtagacgg tctgacgaca cgcaaactgg cggaacggtt gggggttcag cagccggcgc     480
tttactggca cttcaggaac aagcgggcgc tgctcgacgc actggccgaa gccatgctgg     540
cggagaatca tacgcattcg gtgccgagag ccgacgacga ctggcgctca tttctgatcg     600
ggaatgcccg cagcttcagg caggcgctgc tcgcctaccg cgatggcgcg cgcatccatg     660
ccggcacgcg accgggcgca ccgcagatgg aaacggccga cgcgcagctt cgcttcctct     720
gcgaggcggg ttttcggcc ggggacgccg tcaatgcgct gatgacaatc agctacttca     780
ctgttggggc cgtgcttgag gagcaggccg gcgacagcga tgccggcgag gcggcggca     840 ccgttgaaca ggctccgctc tcgccgctgt tgcgggccgc gatagacgcc ttcgacgaag     900
ccggtccgga cgcagcgttc gagcaggac tcgcggtgat tgtcgatgga ttggcgaaaa     960
ggaggctcgt tgtcaggaac gttgaaggac cgagaaaggg tgacgattga tcaggaccgc    1020
tgccggagcg caacccactc actacagcag agccatgtag acaacatccc ctccccctt     1080 ccaccgcgtc agacgcccgt agcagcccgc tacgggcttt tcatgccct gcctagcgt     1140
```

```
ccaagcctca cggccgcgct cggcctctct ggcggccttc tggcgctctt ccgcttcctc    1200
gctcactgac tcgctgcgct cggtcgttcg gctgcggcga gcggtatcag ctcactcaaa    1260
ggcggtaata cggttatcca cagaatcagg ggataacgca ggaaagaaca tgtgagcaaa    1320
aggccagcaa aaggccagga accgtaaaaa ggccgcgttg ctggcgtttt tccataggct    1380
ccgcccccct gacgagcatc acaaaaatcg acgctcaagt cagaggtggc gaaacccgac    1440
aggactataa agataccagg cgtttccccc tggaagctcc ctcgtgcgct ctcctgttcc    1500
gaccctgccg cttaccggat acctgtccgc ctttctccct tcgggaagcg tggcgctttt    1560
ccgctgcata accctgcttc ggggtcatta tagcgatttt ttcggtatat ccatcctttt    1620
tcgcacgata tacaggattt tgccaaaggg ttcgtgtaga cttccttgg tgtatccaac     1680 ggcgtcagcc gggcaggata ggtgaagtag gcccacccgc gagcgggtgt tccttcttca    1740
ctgtccctta ttcgcacctg gcggtgctca acgggaatcc tgctctgcga ggctggccgg    1800
ctaccgccgg cgtaacagat gagggcaagc ggatggctga tgaaccaag ccaaccagga     1860 agggcagccc acctatcaag gtgtactgcc ttccagacga cgaagagcg attgaggaaa     1920 aggcggcgg ggccggcatg agcctgtcgg cctacctgct ggccgtcggc cagggctaca     1980
aaatcacggg cgtcgtggac tatgagcacg tccgcgagct ggcccgcatc aatggcgacc    2040
tgggccgcct gggcggcctg ctgaaactct ggctcaccga cgaccgcgc acggcgcggt     2100 tcggtgatgc cacgatcctc gccctgctgg cgaagatcga agagaagcag gacgagcttg    2160
gcaaggtcat gatgggcgtg gtccgcccga gggcagagcc atgactttt tagccgctaa     2220 aacggccggg gggtgcgcgt gattgccaag cacgtcccca tgcgctccat caagaagagc    2280
gacttcgcgg agctggtgaa gtacatcacc gacgagcaag gcaagaccga gcgcctttgc    2340
gacgctcacc gggctggttg ccctcgccgc tgggctggcg gccgtctatg gccctgcaaa    2400
cgcgccagaa acgccgtcga agccgtgtgc gagacaccgc ggccgccggc gttgtggata    2460
cctcgcggaa aacttggccc tcactgacag atgaggggcg gacgttgaca cttgaggggc    2520
cgactcaccc ggcgcggcgt tgacagatga ggggcaggct cgatttcggc cggcgacgtg    2580
gagctggcca gcctcgcaaa tcggcgaaaa cgcctgattt tacgcgagtt tcccacagat    2640
gatgtggaca gcctgggga taagtgccct gcggtattga cattgagggg gcgcgactac    2700
tgacagatga ggggcgcgat ccttgacact tgaggggcag agtgctgaca gatgaggggc    2760
gcacctattg acatttgagg ggctgtccac aggcagaaaa tccagcatt gcaagggttt     2820 ccgcccgttt ttcggccacc gctaacctgt ctttaacct gcttttaaac caatatttat     2880
aaaccttgtt tttaaccagg gctgcgccct gtgcgcgtga ccgcgcacgc cgaagggggg    2940 tgcccccct tctcgaaccc tcccggcccg ctaacgcggg cctcccatcc cccagggggc    3000
tgcgcccctc ggccgcgaac ggcctcaccc caaaaatggc agcgctggca gtccttgcca    3060
ttgccgggat cggggcagta acgggatggg cgatcagccc gagcgcgacg cccggaagca    3120
ttgacgtgcc gcaggtgctg gcatcgacat tcagcgacca ggtgccgggc agtgagggcg    3180
gcggcctggg tggcggcctg cccttcactt cggccgtcgg ggcattcacg gacttcatgg    3240
cggggccggc aattttacc ttgggcattc ttggcatagt ggtcgcgggt gccgtgctcg      3300
tgttcggggg tgcgataaac ccagcgaacc atttgaggtg ataggtaaga ttataccgag    3360
gtatgaaaac gagaattgga cctttacaga attactctat gaagcgccat atttaaaaag    3420
ctaccaagac gaagaggatg aagaggatga ggagcagat tgccttgaat atattgacaa     3480
tactgataag ataatatatc ttttatatag aagatatcgc cgtatgtaag gatttcaggg    3540
```

```
ggcaaggcat aggcagcgcg cttatcaata tatctataga atgggcaaag cataaaaact    3600
tgcatggact aatgcttgaa acccaggaca ataaccttat agcttgtaaa ttctatcata    3660
attgggtaat gactccaact tattgatagt gttttatgtt cagataatgc ccgatgactt    3720
tgtcatgcag ctccaccgat tttgagaacg acagcgactt ccgtcccagc cgtgccaggt    3780
gctgcctcag attcaggtta tgccgctcaa ttcgctgcgt atatcgcttg ctgattacgt    3840
gcagctttcc cttcaggcgg gattcataca gcggccagcc atccgtcatc catatcacca    3900
cgtcaaaggg tgacacgcag gctcataagac gccccagcgt cgccatagtg cgttcaccga    3960
atacgtgcgc aacaaccgtc ttccggagac tgtcatacgc gtaaaacagc cagcgctggc    4020
gcgatttagc cccgacatag ccccactgtt cgtccatttc cgcgcagacg atgacgtcac    4080
tgcccggctg tatgcgcgag gttaccgact gcggcctgag tttttaagt gacgtaaaat    4140
cgtgttgagg ccaacgccca taatgcgggc tgttgcccgg catccaacgc cattcatggc    4200
catatcaatg attttctggt gcgtaccggg ttgagaagcg gtgtaagtga actgcagttg    4260
ccatgtttta cggcagtgag agcagagata gcgctgatgt ccggcggtgc ttttgccgtt    4320
acgcaccacc ccgtcagtag ctgaacagga gggacagctg atagacacag aagccactgg    4380
agcacctcaa aaacaccatc atacactaaa tcagtaagtt ggcagcatca cccataattg    4440
tggtttcaaa atcggctccg tcgatactat gttatacgcc aactttgaaa caactttga    4500
aaaagctgtt ttctggtatt taaggtttta gaatgcaagg aacagtgaat tggagttcgt    4560
cttgttataa ttagcttctt ggggtatctt taaatactgt agaaagagg aaggaaataa    4620
taaatggcta aaatgagaat atcaccggaa ttgaaaaaac tgatcgaaaa ataccgctgc    4680
gtaaaagata cggaaggaat gtctcctgct aaggtatata agctggtggg agaaaatgaa    4740
aacctatatt taaaaatgac ggacagccgg tataagggga ccacctatga tgtggaacgg    4800
gaaaaggaca tgatgctatg gctggaagga aagctgcctg ttccaaaggt cctgcacttt    4860
gaacggcatg atggctggag caatctgctc atgagtgagg ccgatggcgt cctttgctcg    4920
gaagagtatg aagatgaaca aagccctgaa aagattatcg agctgtatgc ggagtgcatc    4980
aggctctttc actccatcga catatcggat tgtccctata cgaatagctt agacagccgc    5040
ttagccgaat tggattactt actgaataac gatctggccg atgtggattg cgaaaactgg    5100
gaagaagaca ctccatttaa agatccgcgc gagctgtatg atttttttaa gacggaaaag    5160
cccgaagagg aacttgtctt ttcccacggc gacctgggag acagcaacat ctttgtgaaa    5220
gatggcaaag taagtggctt tattgatctt gggagaagcg gcagggcgga caagtggtat    5280
gacattgcct tctgcgtccg gtcgatcagg gaggatatcg gggaagaaca gtatgtcgag    5340
ctatttttg acttactggg gatcaagcct gattgggaga aaataaaata ttatatttta    5400
ctggatgaat tgttttagta cctagatgtg gcgcaacgat gccggcgaca agcaggagcg    5460
caccgacttc ttccgcatca gtgtttttgg ctctcaggcc gaggcccacg gcaagtattt    5520
gggcaagggg tcgctggtat tcgtgcaggg caagattcgg aataccaagt acgaaagga    5580
cggccagacg gtctacggga ccgacttcat tgccgataag gtggattatc tggacaccaa    5640
ggcaccaggc gggtcaaatc aggaataagg gcacattgcc ccggcgtgag tcggggcaat    5700
cccgcaagga gggtgaatga atcggacgtt tgaccggaag gcatacaggc aagaactgat    5760
cgacgcgggg ttttccgccg aggatgccga aaccatcgca agccgcaccg tcatgcgtgc    5820
gccccgcgaa accttccagt ccgtcggctc gatggtccag caagctacgg ccaagatcga    5880
```

```
gcgcgacagc gtgcaactgg ctccccctgc cctgcccgcg ccatcggccg ccgtggagcg      5940
ttcgcgtcgt ctcgaacagg aggcggcagg tttggcgaag tcgatgacca tcgacacgcg      6000
aggaactatg acgaccaaga agcgaaaaac cgccggcgag gacctggcaa aacaggtcag      6060
cgaggccaag caggccgcgt tgctgaaaca cacgaagcag cagatcaagg aaatgcagct      6120
ttccttgttc gatattgcgc cgtggccgga cacgatgcga gcgatgccaa acgacacggc      6180
ccgctctgcc ctgttcacca cgcgcaacaa gaaaatcccg cgcgaggcgc tgcaaaacaa      6240
ggtcattttc cacgtcaaca aggacgtgaa gatcacctac accggcgtcg agctgcgggc      6300
cgacgatgac gaactggtgt ggcagcaggt gttggagtac gcgaagcgca cccctatcgg      6360
cgagccgatc accttcacgt tctacgagct tgccaggac ctgggctggt cgatcaatgg       6420
ccggtattac acgaaggccg aggaatgcct gtcgcgccta caggcgacgg cgatgggctt      6480
cacgtccgac cgcgttgggc acctggaatc ggtgtcgctg ctgcaccgct tccgcgtcct      6540
ggaccgtggc aagaaaacgt cccgttgcca ggtcctgatc gacgaggaaa tcgtcgtgct      6600
gtttgctggc gaccactaca cgaaattcat atgggagaag taccgcaagc tgtcgccgac      6660
ggcccgacgg atgttcgact atttcagctc gcaccgggag ccgtacccgc tcaagctgga      6720
aaccttccgc ctcatgtgcg gatcggattc cacccgcgtg aagaagtggc gcgagcaggt      6780
cggcgaagcc tgcgaagagt tgcgaggcag cggcctggtg gaacacgcct gggtcaatga      6840
tgacctggtg cattgcaaac gctagggcct tgtggggtca gttccggctg ggggttcagc      6900
agccagcgct ttactggcat ttcaggaaca agcgggcact gctcgacgca cttgcttcgc      6960
tcagtatcgc tcgggacgca cggcgcgctc tacgaactgc cgataaacag aggattaaaa      7020
ttgacaattg tgattaaggc tcagattcga cggcttggag cggccgacgt gcaggatttc      7080
cgcgagatcc gattgtcggc cctgaagaaa gctccagaga tgttcgggtc cgtttacgag      7140
cacgaggaga aaaagcccat ggaggcgttc gctgaacggt tgcgagatgc cgtggcattc      7200
ggcgcctaca tcgacggcga gatcattggg ctgtcggtct tcaaacagga ggacggcccc      7260
aaggacgctc acaaggcgca tctgtccggc gttttcgtgg agcccgaaca gcgaggccga      7320
ggggtcgccg gtatgctgct gcgggcgttg ccggcgggtt tattgctcgt gatgatcgtc      7380
cgacagattc caacgggaat ctggtggatg cgcatcttca tcctcggcgc acttaatatt      7440
tcgctattct ggagcttgtt gtttatttcg gtctaccgcc tgccgggcgg ggtcgcggcg      7500
acggtaggcg ctgtgcagcc gctgatggtc gtgttcatct ctgccgctct gctaggtagc      7560
ccgatacgat tgatggcggt cctgggggct atttgcggaa ctgcgggcgt ggcgctgttg      7620
gtgttgacac caaacgcagc gctagatcct gtcggcgtcg cagcgggcct ggcggggggcg      7680 gtttccatgg cgttcggaac cgtgctgacc cgcaagtggc aacctcccgt gcctctgctc      7740
acctttaccg cctggcaact ggcggccgga ggacttctgc tcgttccagt agctttagtg      7800
tttgatccgc caatcccgat gcctacagga accaatgttc tcggcctggc gtggctcggc      7860
ctgatcggag cgggtttaac ctacttcctt tggttccggg ggatctcgcg actcgaacct      7920
acagttgttt ccttactggg ctttctcagc cccagatctg gggtcgatca gccggggatg      7980
catcaggccg acagtcggaa cttcgggtcc ccgacctgta ccattcggtg agcaatggat      8040
aggggagtta atatcgtcaa cgttcacttc taaagaaata gcgccactca gcttcctcag      8100
cggctttatc cagcgatttc ctattatgtc ggcatagttc tcaagatcga cagcctgtca      8160
cggttaagcg agaaatgaat aagaaggctg ataattcgga tctctgcgag ggagatgata      8220
tttgatcaca ggcagcaacg ctctgtcatc gttacaatca acatgctacc ctccgcgaga      8280
```

```
tcatccgtgt ttcaaacccg gcagcttagt tgccgttctt ccgaatagca tcggtaacat    8340
gagcaaagtc tgccgcctta caacggctct cccgctgacg ccgtcccgga ctgatgggct    8400
gcctgtatcg agtggtgatt ttgtgccgag ctgccggtcg gggagctgtt ggctggctgg    8460
tggcaggata tattgtggtg taaacaaatt gacgcttaga caacttaata acacattgcg    8520
gacgttttta atgtactggg gtggttttt c ttttcaccag tgagacgggc aacagctgat    8580
tgcccttcac cgcctggccc tgagagagtt gcagcaagcg gtccacgctg gtttgcccca    8640
gcaggcgaaa atcctgtttg atggtggttc cgaaatcggc aaaatccctt ataaatcaaa    8700
agaatagccc gagatagggt tgagtgttgt tccagtttgg aacaagagtc cactattaaa    8760
gaacgtggac tccaacgtca aagggcgaaa aaccgtctat cagggcgatg gcccactacg    8820
tgaaccatca cccaaatcaa gttttttggg gtcgaggtgc cgtaaagcac taaatcggaa    8880
ccctaaaggg agccccgat ttagagcttg acggggaaag ccggcgaacg tggcgagaaa     8940
ggaagggaag aaagcgaaag gagcgggcgc cattcaggct gcgcaactgt tgggaagggc    9000
gatcggtgcg ggcctcttcg ctattacgcc agctggcgaa aggggggatgt gctgcaaggc    9060
gattaagttg ggtaacgcca gggttttccc agtcacgacg ttgtaaaacg acggccagtg    9120
aattaattcc catcttgaaa gaatatagt ttaaatattt attgataaaa taacaagtca     9180
ggtattatag tccaagcaaa aacataaatt tattgatgca agtttaaatt cagaaatatt    9240
tcaataactg attatatcag ctggtacatt gccgtagatg aaagactgag tgcgatatta    9300
tgtgtaatac ataaattgat gatatagcta gcttagctca tcgggggatc cgtcgaagct    9360
agcttgggtc ccgctcagaa gaactcgtca agaaggcgat agaaggcgat gcgctgcgaa    9420
tcgggagcgg cgataccgta aagcacgagg aagcggtcag cccattcgcc gccaagctct    9480
tcagcaatat cacgggtagc caacgctatg tcctgatagc ggtccgccac acccagccgg    9540
ccacagtcga tgaatccaga aaagcggcca ttttccacca tgatattcgg caagcaggca    9600
tcgccatggg tcacgacgag atcctcgccg tcgggcatgc gcgccttgag cctggcgaac    9660
agttcggctg gcgcgagccc ctgatgctct tcgtccagat catcctgatc gacaagaccg    9720
gcttccatcc gagtacgtgc tcgctcgatg cgatgtttcg cttggtggtc gaatgggcag    9780
gtagccggat caagcgtatg cagccgccgc attgcatcag ccatgatgga tactttctcg    9840
gcaggagcaa ggtgagatga caggagatcc tgccccggca cttcgcccaa tagcagccag    9900
tccctt cccg cttcagtgac aacgtcgagc acagctgcgc aaggaacgcc cgtcgtggcc    9960
agccacgata gccgcgctgc ctcgtcctgc agttcattca gggcaccgga caggtcggtc   10020
ttgacaaaaa gaaccgggcg cccctgcgct gacagccgga acacggcggc atcagagcag   10080
ccgattgtct gttgtgccca gtcatagccg aatagcctct ccacccaagc ggccggagaa   10140
cctgcgtgca atccatcttg ttcaatccaa gctcccatgg gcctcgact agagtcgaga   10200
tctggattga gagtgaatat gagactctaa ttggataccg aggggaattt atggaacgtc   10260
agtggagcat ttttgacaag aaatatttgc tagctgatag tgaccttagg cgactttga    10320
acgcgcaata atggtttctg acgtatgtgc ttagctcatt aaactccaga aacccgcggc   10380
tgagtggctc cttcaacgtt gcggttctgt cagttccaaa cgtaaaacgg cttgtcccgc   10440
gtcatcggcg ggggtcataa cgtgactccc ttaattctcc gctcatgatc ttgatcccct   10500
gcgccatcag atccttggcg gcaagaaagc catccagttt actttgcagg gcttcccaac   10560
cttaccagag ggcgccccag ctggcaattc cggttcgctt gctgtccata aaaccgccca   10620
```

```
gtctagctat cgccatgtaa gcccactgca agctacctgc tttctctttg cgcttgcgtt   10680
ttcccttgtc cagatagccc agtagctgac attcatccgg ggtcagcacc gtttctgcgg   10740
actggctttc tacgtgttcc gcttccttta gcagcccttg cgccctgagt gcttgcggca   10800
gcgtgaagct ttcttcatcg gtgattgatt cctttaaaga cttatgtttc ttatcttgct   10860
tctgaggcaa gtattcagtt accagttacc acttatattc tggactttct gactgcatcc   10920 tcattttttcc aacattttaa atttcactat tggctgaatg cttcttcttt gaggaagaaa   10980
caattcagat ggcagaaatg tatcaaccaa tgcatatata caaatgtacc tcttgttctc   11040
aaaacatcta tcggatggtt ccatttgctt tgtcatccaa ttagtgacta ctttatatta   11100
ttcactcctc tttattacta ttttcatgcg aggttgccat gtacattata tttgtaagga   11160
ttgacgctat tgagcgtttt tcttcaattt tcttttatttt agacatgggt atgaaatgtg   11220
tgttagagtt gggttgaatg agatatacgt tcaagtgaat ggcataccgt tctcgagtaa   11280
ggatgaccta cccattcttg agacaaatgt tacattttag tatcagagta aaatgtgtac   11340
ctataactca aattcgattg acatgtatcc attcaacata aaattaaacc agcctgcacc   11400
tgcatccaca tttcaagtat tttcaaaccg ttcggctcct atccaccggg tgtaacaaga   11460
cggattccga atttggaaga ttttgactca aattcccaat ttatattgac cgtgactaaa   11520
tcaactttaa cttctataat tctgattaag ctcccaattt atattcccaa cggcactacc   11580
tccaaaattt atagactctc atccccttttt aaaccaactt agtaaacgtt ttttttttta   11640
attttatgaa gttaagtttt taccttgttt ttaaaaagaa tcgttcataa gatgccatgc   11700
cagaacatta gctacacgtt acacatagca tgcagccgcg gagaattgtt tttcttcgcc   11760
acttgtcact ccccttcaaac acctaagagc ttctctctca cagcacacac atacaatcac   11820
atgcgtgcat gcattattac acgtgatcgc catgcaaatc tcctttatag cctataaatt   11880
aactcatccg cttcactctt tactcaaacc aaaactcatc aatacaaaca agattaaaaa   11940
catacacgag gatccactag tatgtctgct gctgctgata gattaaactt aacttccggc   12000
cacttgaatg ctggtagaaa gagaagttcc tcttctgttt ctttgaaggc tgccgaaaag   12060
cctttcaagg ttactgtgat tggatctggt aactggggta ctactattgc caaggtggtt   12120
gccgaaaatt gtaagggata cccagaagtt ttcgctccaa tagtacaaat gtgggtgttc   12180
gaagaagaga tcaatggtga aaaattgact gaaatcataa atactagaca tcaaaacgtg   12240
aaatacttgc ctggcatcac tctacccgac aatttggttg ctaatccaga cttgattgat   12300
tcagtcaagg atgtcgacat catcgtcttc aacattccac atcaattttt gccccgtatc   12360
tgtagccaat tgaaaggtca tgttgattca cacgtcagag ctatctcctg tctaaagggt   12420
tttgaagttg gtgctaaagg tgtccaattg ctatcctctt acatcactga ggaactaggt   12480
attcaatgtg gtgctctatc tggtgctaac attgccactg aagtcgctca agaacactgg   12540
tctgaaacaa cagttgctta ccacattcca aaggatttca gaggcgaggg caaggacgtc   12600
gaccataagg ttctaaaggc cttgttccac agaccttact ccacgttag tgtcatcgaa   12660 gatgttgctg gtatctccat ctgtggtgct ttgaagaacg ttgttgcctt aggttgtggt   12720
ttcgtcgaag gtctaggctg gggtaacaac gcttctgctg ccatccaaag agtcggtttg   12780
ggtgagatca tcagattcgg tcaaatgttt ttcccagaat ctagaagaa acatactac   12840 caagagtctg ctggtgttgc tgatttgatc accacctgcg ctggtggtag aaacgtcaag   12900
gttgctaggc taatggctac ttctggtaag gacgcctggg aatgtgaaaa ggagttgttg   12960
aatggccaat ccgctcaagg tttaattacc tgcaaagaag ttcacgaatg gttggaaaca   13020
```

-continued

```
tgtggctctg tcgaagactt cccattattt gaagccgtat accaaatcgt ttacaacaac    13080
tacccaatga agaacctgcc ggacatgatt gaagaattag atctacatga agattagctc    13140
gacgaatttc cccgatcgtt caaacatttg gcaataaagt ttcttaagat tgaatcctgt    13200
tgccggtctt gcgatgatta tcatataatt tctgttgaat tacgttaagc atgtaataat    13260
taacatgtaa tgcatgacgt tatttatgag atgggttttt atgattagag tcccgcaatt    13320
atacatttaa tacgcgatag aaaacaaaat atagcgcgca aactaggata aattatcgcg    13380
cgcggtgtca tctatgttac tagatcggga attcagatcg gctgagtggc tccttcaacg    13440
ttgcggntct gtcagtncca aacgtaaaac gggttggtcc gcggnatcgg cgggggggcc    13500
ttaaccgtgn actnccntna ttnctccggc ttcantgnnn agaattggnc ntttccccgn    13560
cntcagttta aactatcagg tgtttgacag gatatatttg gcgggtaaac ctaaganaaa    13620
agagcgttta ttagaataat cggatattta aaagggccgn gaaaaggttt atcccttccg    13680
tccatttgta tgngcatgcc naccaccagg gttcccca                            13718
```

<210> SEQ ID NO 37
<211> LENGTH: 1254
<212> TYPE: DNA
<213> ORGANISM: Emericella nidulans
<220> FEATURE:
<221> NAME/KEY: CDS
<222> LOCATION: (1)..(1251)
<223> OTHER INFORMATION: coding for G3PDH

<400> SEQUENCE: 37

```
atg ggc tct ctt gga ccg tat aag caa aag cac aag gtg act gtg gtg      48
Met Gly Ser Leu Gly Pro Tyr Lys Gln Lys His Lys Val Thr Val Val
 1               5                  10                  15 gga tcg ggt aac tgg ggc acc gct ata gcc aaa atc gtc gcc gag aat      96
Gly Ser Gly Asn Trp Gly Thr Ala Ile Ala Lys Ile Val Ala Glu Asn
             20                  25                  30 act gcc agc aac cct gcg gtc ttt gag aag gat gtt cag atg tgg gtt     144
Thr Ala Ser Asn Pro Ala Val Phe Glu Lys Asp Val Gln Met Trp Val
         35                  40                  45 ttc gag gaa aag gtc gag att ccg aaa tcg tcg aag cat tat gat cct     192
Phe Glu Glu Lys Val Glu Ile Pro Lys Ser Ser Lys His Tyr Asp Pro
     50                  55                  60 gcc tct tct ctt tgc cag ggc ccg cag aat ctg aca gat att atc aac     240
Ala Ser Ser Leu Cys Gln Gly Pro Gln Asn Leu Thr Asp Ile Ile Asn
 65                  70                  75                  80 cat acc cat gag aat atc aag tac ctc ccc gga att acc ctt ccg gaa     288
His Thr His Glu Asn Ile Lys Tyr Leu Pro Gly Ile Thr Leu Pro Glu
                 85                  90                  95 aac ttg att gcc aat cca tcg cta gtc gac gcg gtt caa gac agc act     336
Asn Leu Ile Ala Asn Pro Ser Leu Val Asp Ala Val Gln Asp Ser Thr
            100                 105                 110 atc ctc gtc ttc aac cta ccc cat caa ttc atc atc aat att tgt gaa     384
Ile Leu Val Phe Asn Leu Pro His Gln Phe Ile Ile Asn Ile Cys Glu
        115                 120                 125 cag atc aag ggc aag att gtc cca tac gcg cgt gga att tct tgc ata     432
Gln Ile Lys Gly Lys Ile Val Pro Tyr Ala Arg Gly Ile Ser Cys Ile
    130                 135                 140 aag ggc gtg gat gtg aat gag gaa gga gtc cac ctg ttt tcc gaa aca     480
Lys Gly Val Asp Val Asn Glu Glu Gly Val His Leu Phe Ser Glu Thr
145                 150                 155                 160 att gga aag att ctc ggg atc tac tgt ggc gcc ctg tcc ggt gcc aac     528
Ile Gly Lys Ile Leu Gly Ile Tyr Cys Gly Ala Leu Ser Gly Ala Asn
```

```
                165                 170                 175
atc gcg aat gag gtc gcc cag gaa aag tgg tcc gag tct agc att ggt    576
Ile Ala Asn Glu Val Ala Gln Glu Lys Trp Ser Glu Ser Ser Ile Gly
            180                 185                 190 tat gat cca ccg cat ttt gac tct aaa gcc cct tct cct ccc aac cga    624
Tyr Asp Pro Pro His Phe Asp Ser Lys Ala Pro Ser Pro Pro Asn Arg
        195                 200                 205 tcc cct tcc gca tcg act gac aat atc ctg cac ttc gag cac aaa gac    672
Ser Pro Ser Ala Ser Thr Asp Asn Ile Leu His Phe Glu His Lys Asp
    210                 215                 220 gtt tcg ggt caa ctt tcg cgg gta aag cta cag gct cta cct tcc gaa    720
Val Ser Gly Gln Leu Ser Arg Val Lys Leu Gln Ala Leu Pro Ser Glu
225                 230                 235                 240 ttt cct ccc atc gac cat gcc ctt ctc aag tcg cta ttc cac cgt cct    768
Phe Pro Pro Ile Asp His Ala Leu Leu Lys Ser Leu Phe His Arg Pro
                245                 250                 255 tac ttc cat att ggt gtg gta agt gac gtc gca ggt gtt tcg tta gga    816
Tyr Phe His Ile Gly Val Val Ser Asp Val Ala Gly Val Ser Leu Gly
            260                 265                 270 ggt gcc ctt aag aat gtc gtt gct gtc gcg gca ggg tgg gtt gtg ggc    864
Gly Ala Leu Lys Asn Val Val Ala Val Ala Ala Gly Trp Val Val Gly
        275                 280                 285 aaa gga tgg gga gac aat gcg aag gct gca att atg cga gtt ggg ctt    912
Lys Gly Trp Gly Asp Asn Ala Lys Ala Ala Ile Met Arg Val Gly Leu
    290                 295                 300 ttg gaa atg gtg aag ttc ggc gaa cag ttt ttc ggt gct acc atc aac    960
Leu Glu Met Val Lys Phe Gly Glu Gln Phe Phe Gly Ala Thr Ile Asn
305                 310                 315                 320 act cgc acc ttc act gaa gaa agt gct ggt gtt gcc gat cta atc acg   1008
Thr Arg Thr Phe Thr Glu Glu Ser Ala Gly Val Ala Asp Leu Ile Thr
                325                 330                 335 agt tgc agt ggc gga cga aac ttc cgc tgc gca aag ctt agc att gaa   1056
Ser Cys Ser Gly Gly Arg Asn Phe Arg Cys Ala Lys Leu Ser Ile Glu
            340                 345                 350 aga aac cag ccg att gag aaa atc gag gag aca gag ttg aac ggc cag   1104
Arg Asn Gln Pro Ile Glu Lys Ile Glu Glu Thr Glu Leu Asn Gly Gln
        355                 360                 365 aag ctg caa ggc act ttg act gca gtc gaa gtc aac agt ttc ttg aaa   1152
Lys Leu Gln Gly Thr Leu Thr Ala Val Glu Val Asn Ser Phe Leu Lys
    370                 375                 380 aag caa ggt tta gaa gaa gag ttc cca ttg ttt act gca gtc tac cga   1200
Lys Gln Gly Leu Glu Glu Glu Phe Pro Leu Phe Thr Ala Val Tyr Arg
385                 390                 395                 400 gtt ctt caa ggc acc atg tct gtg gac gag att cct tct ttc att gag   1248
Val Leu Gln Gly Thr Met Ser Val Asp Glu Ile Pro Ser Phe Ile Glu
                405                 410                 415 cgg taa                                                            1254
Arg

<210> SEQ ID NO 38
<211> LENGTH: 417
<212> TYPE: PRT
<213> ORGANISM: Emericella nidulans

<400> SEQUENCE: 38

Met Gly Ser Leu Gly Pro Tyr Lys Gln Lys His Lys Val Thr Val Val
1               5                   10                  15

Gly Ser Gly Asn Trp Gly Thr Ala Ile Ala Lys Ile Val Ala Glu Asn
            20                  25                  30
```

```
Thr Ala Ser Asn Pro Ala Val Phe Glu Lys Asp Val Gln Met Trp Val
        35                  40                  45

Phe Glu Glu Lys Val Glu Ile Pro Lys Ser Ser Lys His Tyr Asp Pro
 50                  55                  60

Ala Ser Ser Leu Cys Gln Gly Pro Gln Asn Leu Thr Asp Ile Ile Asn
 65                  70                  75                  80

His Thr His Glu Asn Ile Lys Tyr Leu Pro Gly Ile Thr Leu Pro Glu
                 85                  90                  95

Asn Leu Ile Ala Asn Pro Ser Leu Val Asp Ala Val Gln Asp Ser Thr
                100                 105                 110

Ile Leu Val Phe Asn Leu Pro His Gln Phe Ile Ile Asn Ile Cys Glu
            115                 120                 125

Gln Ile Lys Gly Lys Ile Val Pro Tyr Ala Arg Gly Ile Ser Cys Ile
130                 135                 140

Lys Gly Val Asp Val Asn Glu Glu Gly Val His Leu Phe Ser Glu Thr
145                 150                 155                 160

Ile Gly Lys Ile Leu Gly Ile Tyr Cys Gly Ala Leu Ser Gly Ala Asn
                165                 170                 175

Ile Ala Asn Glu Val Ala Gln Glu Lys Trp Ser Glu Ser Ile Gly
                180                 185                 190

Tyr Asp Pro Pro His Phe Asp Ser Lys Ala Pro Ser Pro Asn Arg
            195                 200                 205

Ser Pro Ser Ala Ser Thr Asp Asn Ile Leu His Phe Glu His Lys Asp
210                 215                 220

Val Ser Gly Gln Leu Ser Arg Val Lys Leu Gln Ala Leu Pro Ser Glu
225                 230                 235                 240

Phe Pro Pro Ile Asp His Ala Leu Leu Lys Ser Leu Phe His Arg Pro
                245                 250                 255

Tyr Phe His Ile Gly Val Val Ser Asp Val Ala Gly Val Ser Leu Gly
                260                 265                 270

Gly Ala Leu Lys Asn Val Val Ala Val Ala Ala Gly Trp Val Val Gly
            275                 280                 285

Lys Gly Trp Gly Asp Asn Ala Lys Ala Ala Ile Met Arg Val Gly Leu
290                 295                 300

Leu Glu Met Val Lys Phe Gly Glu Gln Phe Phe Gly Ala Thr Ile Asn
305                 310                 315                 320

Thr Arg Thr Phe Thr Glu Glu Ser Ala Gly Val Ala Asp Leu Ile Thr
                325                 330                 335

Ser Cys Ser Gly Gly Arg Asn Phe Arg Cys Ala Lys Leu Ser Ile Glu
            340                 345                 350

Arg Asn Gln Pro Ile Glu Lys Ile Glu Glu Thr Glu Leu Asn Gly Gln
            355                 360                 365

Lys Leu Gln Gly Thr Leu Thr Ala Val Glu Val Asn Ser Phe Leu Lys
370                 375                 380

Lys Gln Gly Leu Glu Glu Glu Phe Pro Leu Phe Thr Ala Val Tyr Arg
385                 390                 395                 400

Val Leu Gln Gly Thr Met Ser Val Asp Glu Ile Pro Ser Phe Ile Glu
                405                 410                 415

Arg

<210> SEQ ID NO 39
<211> LENGTH: 999
<212> TYPE: DNA
<213> ORGANISM: Debaryomyces hansenii
```

```
<220> FEATURE:
<221> NAME/KEY: CDS
<222> LOCATION: (1)..(996)
<223> OTHER INFORMATION: coding for G3PDH (partial)

<400> SEQUENCE: 39 gga tct ggt aac tgg ggt act gct gtt gct aag atc gta tct gaa aac      48
Gly Ser Gly Asn Trp Gly Thr Ala Val Ala Lys Ile Val Ser Glu Asn
  1               5                  10                  15 acg gct gaa aaa cca gaa gtg ttc gaa aag caa gtg aac atg tgg gtt      96
Thr Ala Glu Lys Pro Glu Val Phe Glu Lys Gln Val Asn Met Trp Val
             20                  25                  30 ttt gaa gaa gaa gtt gac gga caa aag ttg act gaa atc atc aac gcc     144
Phe Glu Glu Glu Val Asp Gly Gln Lys Leu Thr Glu Ile Ile Asn Ala
         35                  40                  45 aaa cac gaa aac gtt aag tac ttg cca gaa gtc aag ttg ccg gaa aac     192
Lys His Glu Asn Val Lys Tyr Leu Pro Glu Val Lys Leu Pro Glu Asn
 50                  55                  60 ttg gtt gca aac cca gac gtt gtt gac act gtc aag gat gca gac tta     240
Leu Val Ala Asn Pro Asp Val Val Asp Thr Val Lys Asp Ala Asp Leu
 65                  70                  75                  80 tta att ttt aac att cca cat caa ttc tta cca aga gtg tgt aag caa     288
Leu Ile Phe Asn Ile Pro His Gln Phe Leu Pro Arg Val Cys Lys Gln
                 85                  90                  95 ttg gtt ggc cat gtc aag cca tct gcc aga gcc atc tcc tgt ttg aag     336
Leu Val Gly His Val Lys Pro Ser Ala Arg Ala Ile Ser Cys Leu Lys
            100                 105                 110 ggt ttg gaa gtt ggc cca gaa ggt tgt aag ttg tta tcg caa tct atc     384
Gly Leu Glu Val Gly Pro Glu Gly Cys Lys Leu Leu Ser Gln Ser Ile
        115                 120                 125 aac gat act tta ggt gtc cac tgt ggt gtc tta tct ggt gcc aac att     432
Asn Asp Thr Leu Gly Val His Cys Gly Val Leu Ser Gly Ala Asn Ile
130                 135                 140 gcc aac gaa gtt gcc aga gaa aga tgg tct gaa acc acc att gcc tac     480
Ala Asn Glu Val Ala Arg Glu Arg Trp Ser Glu Thr Thr Ile Ala Tyr
145                 150                 155                 160 aac att cca gaa gat ttc aga ggt aag ggt aga gat atc gac gaa tac     528
Asn Ile Pro Glu Asp Phe Arg Gly Lys Gly Arg Asp Ile Asp Glu Tyr
                165                 170                 175 gtc tta aag caa tta ttc cac aga acc tac ttc cat gtc aga gtc atc     576
Val Leu Lys Gln Leu Phe His Arg Thr Tyr Phe His Val Arg Val Ile
            180                 185                 190 aac gac atc ata ggt gct tct ttc gct ggt gct ttg aag aat gtt gtt     624
Asn Asp Ile Ile Gly Ala Ser Phe Ala Gly Ala Leu Lys Asn Val Val
        195                 200                 205 gcc tgt gct gtt ggt ttc gtt atc ggt gcc ggc tgg ggt gac aac gct     672
Ala Cys Ala Val Gly Phe Val Ile Gly Ala Gly Trp Gly Asp Asn Ala
    210                 215                 220 aag gcc gct atc atg aga atc ggt atc aga gaa atc atc cac ttt gcc     720
Lys Ala Ala Ile Met Arg Ile Gly Ile Arg Glu Ile Ile His Phe Ala
225                 230                 235                 240 tct tac tac caa aag ttc ggt gtc aag ggt cca gct cca gaa tcc act     768
Ser Tyr Tyr Gln Lys Phe Gly Val Lys Gly Pro Ala Pro Glu Ser Thr
                245                 250                 255 act ttc act gag gaa tct gcc ggt gtc gct gac tta atc acc act tgt     816
Thr Phe Thr Glu Glu Ser Ala Gly Val Ala Asp Leu Ile Thr Thr Cys
            260                 265                 270 tcc ggt ggt aga aat gtc aag gtt gct aga tac atg att gaa aac aac     864
Ser Gly Gly Arg Asn Val Lys Val Ala Arg Tyr Met Ile Glu Asn Asn
        275                 280                 285
```

```
gtt gac gct tgg gaa gcc gaa aag att gtc tta aag ggt caa tct tct    912
Val Asp Ala Trp Glu Ala Glu Lys Ile Val Leu Lys Gly Gln Ser Ser
    290                 295                 300 caa ggt atc tta act gcc aag gaa gtc cac gaa ttg tta act aac tac    960
Gln Gly Ile Leu Thr Ala Lys Glu Val His Glu Leu Leu Thr Asn Tyr
305                 310                 315                 320 aac tta tcg aat gaa ttc cca tta ttt gaa gcc gta tac                999
Asn Leu Ser Asn Glu Phe Pro Leu Phe Glu Ala Val Tyr
                325                 330
```

<210> SEQ ID NO 40
<211> LENGTH: 332
<212> TYPE: PRT
<213> ORGANISM: Debaryomyces hansenii

<400> SEQUENCE: 40

```
Gly Ser Gly Asn Trp Gly Thr Ala Val Ala Lys Ile Val Ser Glu Asn
 1               5                  10                  15

Thr Ala Glu Lys Pro Glu Val Phe Glu Lys Gln Val Asn Met Trp Val
             20                  25                  30

Phe Glu Glu Val Asp Gly Gln Lys Leu Thr Glu Ile Ile Asn Ala
         35                  40                  45

Lys His Glu Asn Val Lys Tyr Leu Pro Glu Val Lys Leu Pro Glu Asn
     50                  55                  60

Leu Val Ala Asn Pro Asp Val Val Asp Thr Val Lys Asp Ala Asp Leu
 65                  70                  75                  80

Leu Ile Phe Asn Ile Pro His Gln Phe Leu Pro Arg Val Cys Lys Gln
                 85                  90                  95

Leu Val Gly His Val Lys Pro Ser Ala Arg Ala Ile Ser Cys Leu Lys
            100                 105                 110

Gly Leu Glu Val Gly Pro Glu Gly Cys Lys Leu Leu Ser Gln Ser Ile
        115                 120                 125

Asn Asp Thr Leu Gly Val His Cys Gly Val Leu Ser Gly Ala Asn Ile
130                 135                 140

Ala Asn Glu Val Ala Arg Glu Arg Trp Ser Glu Thr Thr Ile Ala Tyr
145                 150                 155                 160

Asn Ile Pro Glu Asp Phe Arg Gly Lys Gly Arg Asp Ile Asp Glu Tyr
                165                 170                 175

Val Leu Lys Gln Leu Phe His Arg Thr Tyr Phe His Val Arg Val Ile
            180                 185                 190

Asn Asp Ile Ile Gly Ala Ser Phe Ala Gly Ala Leu Lys Asn Val Val
        195                 200                 205

Ala Cys Ala Val Gly Phe Val Ile Gly Ala Gly Trp Gly Asp Asn Ala
210                 215                 220

Lys Ala Ala Ile Met Arg Ile Gly Ile Arg Glu Ile Ile His Phe Ala
225                 230                 235                 240

Ser Tyr Tyr Gln Lys Phe Gly Val Lys Gly Pro Ala Pro Glu Ser Thr
                245                 250                 255

Thr Phe Thr Glu Glu Ser Ala Gly Val Ala Asp Leu Ile Thr Thr Cys
            260                 265                 270

Ser Gly Gly Arg Asn Val Lys Val Ala Arg Tyr Met Ile Glu Asn Asn
        275                 280                 285

Val Asp Ala Trp Glu Ala Glu Lys Ile Val Leu Lys Gly Gln Ser Ser
290                 295                 300
```

```
Gln Gly Ile Leu Thr Ala Lys Glu Val His Glu Leu Leu Thr Asn Tyr
305                 310                 315                 320

Asn Leu Ser Asn Glu Phe Pro Leu Phe Glu Ala Val
                325                 330
```

METHODS FOR INCREASING OIL CONTENT IN PLANTS

RELATED APPLICATIONS

This application is a national stage application (under 35 U.S.C. 371) of PCT/EP03/04711 filed May 6, 2003 which claims benefit to German application 102 20753.4 filed May 8, 2002, German application 102 26 413.9, filed Jun. 13, 2002.

FIELD OF THE INVENTION

The invention relates to methods for increasing the oil content in plants, preferably in plant seeds, by expressing yeast glycerol-3-phosphate dehydrogenases (G3PDH), preferably from *Saccharomyces cerevisiae*. The invention furthermore relates to expression constructs for expressing yeast G3PDH in plants, preferably in plant seeds, transgenic plants expressing yeast G3PDH, and to the use of said transgenic plants for the production of food, feeds, seed, pharmaceuticals or fine chemicals, in particular for the production of oils.

DESCRIPTION OF THE BACKGROUND

Increasing the oil content in plants and, in particular, in plant seeds is of great interest for traditional and modern plant breeding and in particular for plant biotechnology. Owing to the increasing consumption of vegetable oils for nutrition or industrial applications, possibilities of increasing or modifying vegetable oils are increasingly the subject of current research (for example Töpfer et al. (1995) Science 268:681-686). Its aim is in particular increasing the fatty acid content in seed oils.

The fatty acids which can be obtained from the vegetable oils are also of particular interest. They are employed, for example, as bases for plasticizers, lubricants, surfactants, cosmetics and the like and are employed as valuable bases in the food and feed industries. Thus, for example, it is of particular interest to provide rapeseed oils with fatty acids with medium chain length since these are in demand in particular in the production of surfactants.

The targeted modulation of plant metabolic pathways by recombinant methods allows the modification of the plant metabolism in an advantageous manner which, when using traditional breeding methods, could only be achieved after a complicated procedure or not at all. Thus, unusual fatty acids, for example specific polyunsaturated fatty acids, are only synthesized in certain plants or not at all in plants and can therefore only be produced by expressing the relevant enzyme in transgenic plants (for example Millar et al. (2000) Trends Plant Sci 5:95-101).

Triacylgylcerides and other lipids are synthesized from fatty acids. Fatty acid biosynthesis and triacylglyceride biosynthesis can be considered as separate biosynthetic pathways owing to the compartmentalization, but as a single biosynthetic pathway in view of the end product. Lipid synthesis can be divided into two part-mechanisms, one which might be termed "prokaryotic" and another which may be termed "eukaryotic" (Browse et al. (1986) Biochemical J 235:25-31; Ohlrogge & Browse (1995) Plant Cell 7:957-970). The prokaryotic mechanism is localized in the plastids and encompasses the biosynthesis of the free fatty acids which are exported into the cytosol, where they enter the eukaryotic mechanism in the form of fatty acid acyl-CoA esters and are esterified with glycerol-3-phosphate (G3P) to give phosphatidic acid (PA). PA is the starting point for the synthesis of neutral and polar lipids. The neutral lipids are synthesized on the endoplasmic reticulum via the Kennedy pathway (voelker (1996) Genetic Engineering, Setlow (ed.) 18:111-113; Shankline & Cahoon (1998) Annu Rev Plant Physiol Plant Mol Biol 49:611-649; Frentzen (1998) Lipids 100:161-166). Besides the biosynthesis of triacylglycerides, G3P also plays a role in glycerol synthesis (for example for the purposes of osmoregulation and against low-temperature stress for example).

GP3, which is essential for the synthesis, is synthesized here by the reduction of dihydroxyacetone phosphate (DHAP) by means of glycerol-3-phosphate dehydrogenase (G3PDH), also termed dihydroxyacetone phosphate reductase. As a rule, NADH acts as reducing cosubstrate (EC 1.1.1.8). A further class of glycerol-3-phosphate dehydrogenases (EC 1.1.99.5) utilizes. FAD as cosubstrate. The enzymes of this class catalyze the reaction of DHAP to G3P. In eukaryotic cells, the two classes of enzymes are distributed in different compartments, those which are NAD-dependent being localized in the cytosol and those which are FAD-dependent being localized in the mitochondria (for *Saccharomyces cerevisiae*, see, for example, Larsson et al., 1998,. Yeast 14:347-357). EP-A 0 353 049 describes an NAD-independent G3PDH from *Bacillus* sp. In *Saccharomyces cerevisiae* too, an NAD-independent G3PDH is identified (Miyata K, Nagahisa M (1969) Plant Cell Physiol 10(3):635-643).

G3PDH is an essential enzyme in prokaryotes and eukaryotes which, besides having a function in lipid biosynthesis, is one of the enzymes responsible for maintaining the cellular redox status by acting on the NAD+/NADH ratio. Deletion of the GPD2 gene in *Saccharomyces cerevisiae* (one of two G3PDH isoforms in this yeast) results in reduced growth under anaerobic conditions. In addition, G3PDH appears to play a role in the stress response of yeast mainly to osmotic stress. Deletion of the GPD1 gene in *Saccharomyces cerevisiae* causes hypersensitivity to sodium chloride.

Sequences for G3PDHs have been described for insects (*Drosophila melanogaster, Drosophila virilis*), plants (*Arabidopsis thaliana, Cuphea lanceolata*), mammals (*Homo sapiens, Mus musculus, Sus scrofa, Rattus norvegicus*), fish (*Salmo salar, Osmerus mordax*), birds (*Ovis aries*), amphibians (*Xenopus laevis*), nematodes (*Caenorhabditis elegans*), algae and bacteria.

Plant cells have at least two G3PDH isoforms, a cytoplasmic isoform and a plastid isoform (Gee R W et al. (1988) Plant Physiol 86:98-103; Gee R W et al. (1988) Plant Physiol 87:379-383). In plants, the enxymatic activity of glycerol-3-phosphate dehydrogenase was first found in potato tubors (Santora G T et al. (1979) Arch Biochem Biophys 196:403-411). Further G3PDH activities which were localized in the cytosol and the plastids were detected in other plants such as peas, maize or soya (Gee R W et al. (1988) PLANT PHYSIOL 86(1): 98-103). G3PDHs from algae such as, for example, two plastid G3PDH isoforms and one cytosolic G3PDH isoform from *Dunaliella tertiolecta* have furthermore been described (Gee R et al.(1993) Plant Physiol 103 (1):243-249; Gee R et al. (1989) PLANT PHYSIOL 91(1): 345-351). As regards the plant G3PDH from *Cuphea lanceolata*, it has been proposed to obtain an increased oil content or a shift in the fatty acid pattern-by overexpression in plants (WO 95/06733). However, such effects have not been proven.

Bacterial G3PDHs and their function have been described (Hsu and Fox (1970) J Bacteriol 103:410-416; Bell (1974) J Bacteriol 117:1065-1076).

WO 01/21820 describes the heterologous expression of a mutated *E. coli* G3PDH for increased stress tolerance and modification of the fatty acid composition in storage oils. The mutated *E. coli* G3PDH (gpsA2FR) exhibits a single amino acid substitution which brings about reduced inhibition via G3P. The heterologous expression of the gpsA2FR mutant leads to glycerolipids with an increased C16 fatty acid content and, accordingly, a reduced C18 fatty acid content. The modifications in the fatty acid pattern are relatively minor: an increase of 2 to 5% in the 16:0 fatty acids and of 1.5 to 3.5% in the 16:3 fatty acids, and a reduction in 18:2 and 18:3 fatty acids by 2 to 5% were observed. The total glycerolipid content remained unaffected.

G3PDHs from yeasts (Ascomycetes) such as
a) *Schizosaccharomyces pombe* (Pidoux AL et al. (1990) Nucleic Acids Res 18 (23): 7145; GenBank Acc.-No.: X56162; Ohmiya R et al. (1995) Mol Microbiol 18(5):963-73; GenBank Acc.-No.: D50796, D50797),
b) *Yarrowia lipolytica* (GenBank Acc.-No.: AJ250328)
c) *Zygosaccharomyces rouxii* (Iwaki T et al. Yeast (2001) 18(8):737-44; GenBank Acc.-No: AB047394, AB047395, AB047397) or
d) *Saccharomyces cerevisiae* (Albertyn J et al. (1994) Mol Cell Biol 14(6):4135-44; Albertyn J et al. (1992) FEBS LETT 308(2):130-132; Merkel J R et al. (1982) Anal Biochem 122 (1):180-185; Wang H T et al. (1994) J Bacteriol. 176(22):7091-5; Eriksson P et al. (1995) Mol Microbiol. 17(1):95-107; GenBank Acc.-No.: U04621, X76859, Z35169).
e) *Emericella nidulans* (GenBank Acc.-No.: AF228340)
f) *Debaryomyces hansenii* (GenBank Acc.-No.: AF210060) are furthermore described.

Summary of the Invention

The present invention provides, generally, methods for increasing the oil content of plants.

One embodiment of the invention is directed to methods of increasing total oil content in a plant organism or a tissue, organ, part, cell or propagation material thereof, comprising expressing a transgenic yeast glycerol-3-phosphate dehydrogenase in said plant organism or in said tissue, organ, part, cell or propagation material thereof; and selecting the plant organism or the tissue, organ, part, cell or propagation material thereof in which the total oil content in said plant organism or in said tissue, organ, part, cell or propagation material thereof, is increased in comparison with a corresponding untransformed plant organism or a tissue, organ, part, cell or propagation material thereof.

Another embodiment of the invention is directed to transgenic expression cassettes comprising a nucleic acid sequence encoding a yeast glycerol-3-phosphate dehydrogenase under the control of a functional promoter.

Another embodiment of the invention is directed to transgenic plant organisms or tissues, organs, parts, cells or propagation materials thereof, comprising a recombinant yeast glycerol-3-phosphate dehydrogenase.

Another embodiment of the invention is directed to methods for the production of oils, fats, free fatty acids or derivatives thereof, comprising expressing a transgenic yeast glycerol-3-phosphate dehydrogenase in a plant organism or tissue, organ, part, cell or propagation material thereof.

Other embodiments and advantages of the invention are set forth in part in the description, which follows, and in part, may be obvious from this description, or may be learned from the practice of the invention.

DESCRIPTION OF THE INVENTION

Figure 1:
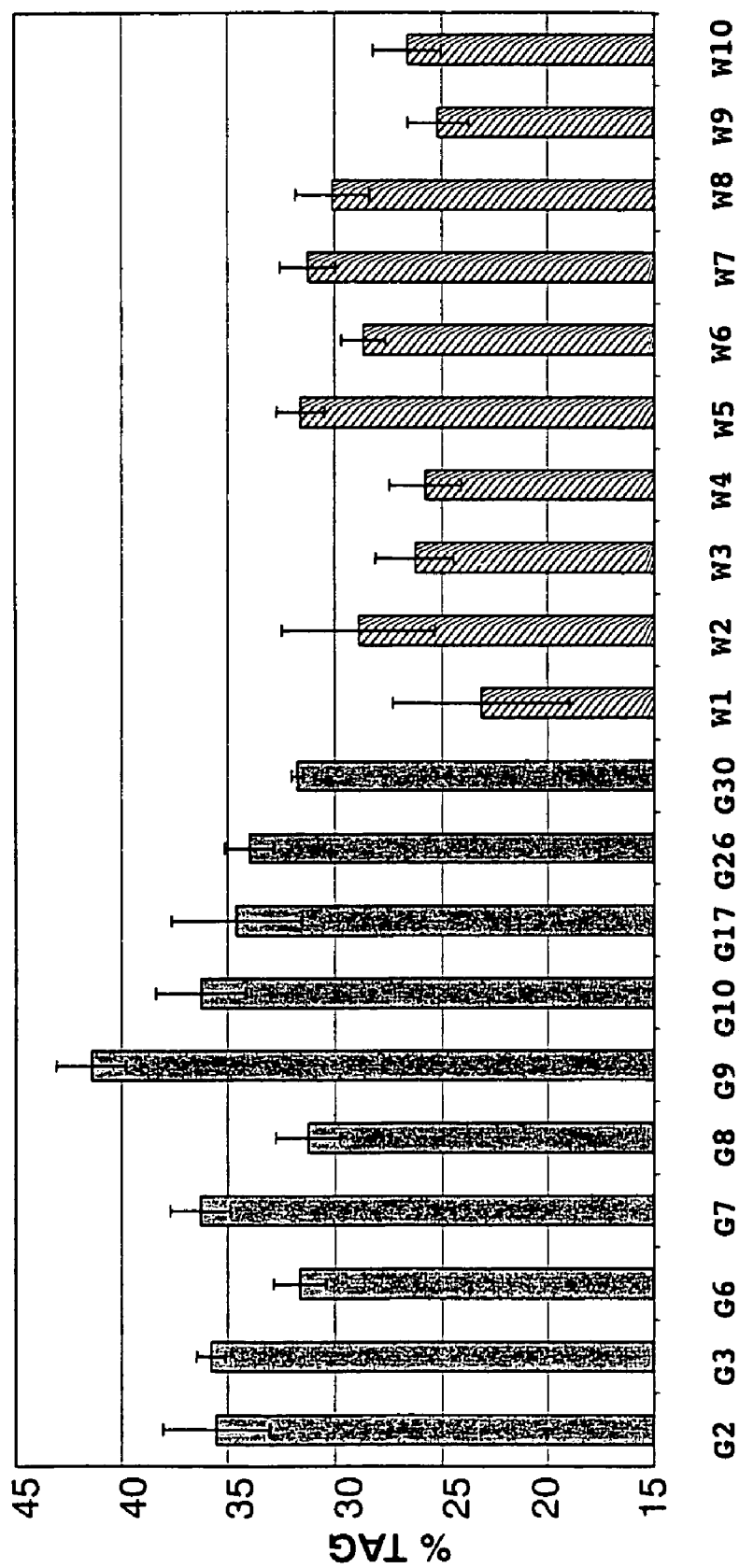
FIG. 1. Oil content in transgenic GDP1p lines.

It is an object of the present invention to provide alternative methods for increasing the oil content in plants. We have found that this object is achieved by the present invention.

A first subject matter of the invention comprises a method of increasing the total oil content in a plant organism or a tissue, organ, part, cell or propagation material thereof, comprising
a) the transgenic expression of yeast glycerol-3-phosphate dehydrogenase in said plant organism or in a tissue, organ, part, cell or propagation material thereof, and
b) the selection of plant organisms in which—in contrast to or comparison with the starting organism—the total oil content in said plant organism or in a tissue, organ, part, cell or propagation material thereof is increased.

Surprisingly, it has been found that the seed-specific heterologous expression of the yeast protein Gpd1p (G3PDH from *Saccharomyces cerevisiae*; SEQ ID NO: 2) in *Arabidopsis* seeds leads to a significantly increased triacylglyceride (storage oils) content. The oil content was increased by approximately 22%, in a transgenic line even by 41%, compared with wild-type control plants (see FIG. 1). The transgenic expression of the yeast glycerol 3-phosphate dehydrogenase had no adverse effects on the growth or other properties of the transformed plants. Since G3PDH is a biosynthetic key enzyme in all plant organisms, the method according to the invention can be applied in principle to all plant species, in addition to the species *Arabidopsis thaliana*, which is employed as model plant. The method according to the invention is preferably applied to oil crops whose oil content is already naturally high and/or for the industrial production of oils.

"Plant" organism or tissue, organ, part, cell or propagation material thereof" is generally understood as meaning any single- or multi-celled organism or a cell, tissue, part or propagation material (such as seeds or fruit) of same which is capable of photosynthesis. Included for the purpose of the invention are all genera and species of higher and lower plants of the Plant Kingdom. Annual, perennial, monocotyledonous and dicotyledonous plants are preferred. Also included are mature plants, seeds, shoots and seedlings, and parts, propagation material (for example tubors, seeds or fruits) and cultures derived from them, for example cell cultures or callus cultures.

For the purposes of the invention, "plant" refers to all genera and species of higher and lower plants of the Plant Kingdom. The term includes the mature plants, seeds, shoots and seedlings, and parts, propagation material, plant organ tissue, protoplasts, callus and other cultures, for example cell cultures, derived from them, and all other species of groups of plant cells giving functional or structural units. Mature plants refers to plants at any developmental stage beyond the seedling. Seedling refers to a young, immature-plant at an early developmental stage.

"Plant" encompasses all annual and perennial monocotyledonous or dicotyledonous plants and includes by way of example, but not by limitation, those of the genera *Cucurbita, Rosa, Vitis, Juglans, Fragaria, Lotus, Medicago, Onobrychis,*

*Trifolium, Trigonella, Vigna, Citrus, Linum, Geranium, Manihot, Daucus, Arabidopsis, Brassica, Raphanus, Sinapis, Atropa, Capsicum, Datura, Hyoscyamus, Lycopersicon, Nicotiana, Solarium, Petunia, Digitalis, Majorana, Cichorium, Helianthus, Lactuca, Bromus, Asparagus, Antirrhinum, Heterocallis, Nemesis, Pelargonium, Panieum, Pennisetum, Ranunculus, Senecio, Salpiglossis, Cucumis, Browaalia, Glycine, Pisum, Phaseolus, Lolium, Oryza, Zea, Avena, Hordeum, Secale, Triticum, Sorghum, Picea* and *Populus*.

Preferred plants are those from the following plant families: Amaranthaceae, Asteraceae, Brassicaceae, Carophyllaceae, Chenopodiaceae, Compositae, Cruciferae, Cucurbitaceae, Labiatae, Leguminosae, Papilionoideae, Liliaceae, Linaceae, Malvaceae, Rosaceae, Rubiaceae, Saxifragaceae, Scrophulariaceae, Solanaceae, Sterculiaceae, Tetragoniaceae, Theaceae, Umbelliferae.

Preferred monocotyledonous plants are selected in particular from the monocotyledonous crop plants such as, for example, the Gramineae family, such as rice, maize, wheat or other cereal species such as barley, millet and sorghum, rye, triticale or oats, and sugar cane, and all grass species.

The invention is applied very particularly preferably from dicotyledonous plant organisms. Preferred dicotyledonous plants are selected in particular from the dicotyledonous crop plants such as, for example, Asteraceae such as sunflower, tagetes or calendula and others, Compositae, especially the genus *Lactuca*, very particularly the species *sativa* (lettuce) and others, Cruciferae, particularly the genus *Brassica*, very particularly the specis *napus* (oilseed rape), *campestris* (beet), *oleracea* cv Tastie (cabbage), *oleracea* cv Snowball Y (cauliflower) and *oleracea* cv Emperor (broccoli) and other cabbages; and the genus *Arabidopsis*, very particularly the species *thaliana*, and cress or canola and others, Cucurbitaceae such as melon, pumpkin/squash or zucchini and others, Leguminosae, particularly the genus *Glycine*, very particularly the species max (soybean), soya, and alfalfa, pea, beans or peanut and others, Rubiaceae, preferably the subclass Lamiidae such as, for example *Coffea arabica* or *Coffea liberica* (coffee bush) and others, Solanaceae, particularly the genus *Lycopersicon*, very particularly the species *esculentum* (tomato), the genus *Solanum*, very particularly the species *tuberosum* (potato) and *melongena* (aubergine) and the genus *Capsicum*, very particularly the genus *annuum* (pepper) and tobacco or paprika and others, Sterculiaceae, preferably the subclass Dilleniidae such as, for example, *Theobroma cacao* (cacao bush) and others, Theaceae, preferably the subclass Dilleniidae such as, for example, *Camellia sinensis* or *Thea sinensis* (tea shrub) and others, Umbelliferae, particularly the genus *Daucus* (very particularly the species *carota* (carrot)) and *Apium* (very particularly the species *graveolens dulce* (celery)) and others;

and linseed, cotton, hemp, flax, cucumber, spinach, carrot, sugar beet and the various tree, nut and grapevine species, in particular banana and kiwi fruit.

Also encompassed are ornamental plants, useful or ornamental trees, flowers, cut flowers, shrubs or turf. Plants which may be mentioned by way of example but not by limitation are angiosperms, bryophytes such as, for example, Hepaticae (liver flowers) and Musci (mosses); pteridophytes such as ferns, horsetail and clubmosses; gymnosperms such as conifers, cycads, ginkgo and Gnetatae, the families of the Rosaceae such as rose, Ericaceae such as rhododendron and azalea, Euphorbiaceae such as poinsettias and croton, Caryophyllaceae such as pinks, Solanaceae such as petunias, Gesneriaceae such as African violet, Balsaminaceae such as touch-me-not, Orchidaceae such as orchids, Iridaceae such as *gladioli*, iris, freesia and *crocus*, Compositae such as marigold, Geraniaceae such as geranium, Liliaceae such as dracena, Moraceae such as ficus, Araceae such as cheeseplant and many others.

Furthermore, plant organisms for the purposes of the invention are further organisms capable of being photosynthetically active such as, for example, algae, cyanobacteria and mosses. Preferred algae are green algae such as, for example, algae from the genus *Haematococcus, Phaedactylum tricornatum, Volvox* or *Dunaliella. Synechocystis* is particularly preferred.

Most preferred are oil crops. Oil crops are understood as being plants whose oil content is already naturally high and/or which can be used for the industrial production of oils. These plants can have a high oil content and/or else a particular fatty acid composition which is of interest industrially. Preferred plants are those with a lipid content of at least 1% by weight. Oil crops encompass by way of example: *Borago officinalis* (borage); *Brassica* species such as *B. campestris, B. napus, B. rapa* (mustard, oilseed rape or turnip rape); *Cannabis sativa* (hemp); *Carthamus tinctorius* (safflower); *Cocos nucifera* (coconut); *Crambe abyssinica* (crambe); *Cuphea* species (*Cuphea* species yield fatty acids of medium chain length, in particular for industrial applications); *Elaeis guinensis* (African oil palm); *Elaeis oleifera* (American oil palm); *Glycine max* (soybean); *Gossypium hirsutum* (American cotton); *Gossypium barbadense* (Egyptian cotton); *Gossypium herbaceum* (Asian cotton); *Helianthus annuus* (sunflower); *Linum usitatissimum* (linseed or flax); *Oenothera biennis* (evening primrose); *Olea europaea* (olive); *Oryza sativa* (rice); *Ricinus communis* (castor); *Sesamum indicum* (sesame); *Triticum* species (wheat); *Zea mays* (maize), and various nut species such as, for example, walnut or almond.

"Total oil content" refers to the sum of all oils, preferably to the sum of the triacylglycerides.

"Oils" encompasses neutral and/or polar lipids and mixtures of these. Those mentioned in Table 1 may be mentioned by way of example, but not by limitation.

TABLE 1

| Classes of plant lipids | |
| --- | --- |
| Neutral lipids | Triacylglycerol (TAG) |
| | Diacylglycerol (DAG) |
| | Monoacylglycerol (MAG) |
| Polar lipids | Monogalactosyldiacylglycerol (MGDG) |
| | Digalactosyldiacylglycerol (DGDG) |
| | Phosphatidylglycerol (PG) |
| | Phosphatidylcholine (PC) |
| | Phosphatidylethanolamine (PE) |
| | Phosphatidylinositol (PI) |
| | Phosphatidylserine (PS) |
| | Sulfoquinovosyldiacylglycerol |

Neutral lipids preferably refers to triacylglycerides. Both neutral and polar lipids may comprise a wide range of various fatty acids. The fatty acids mentioned in Table 2 may be mentioned by way of example, but not by limitation.

TABLE 2

Overview over various fatty acids (selection)

| Nomenclature[1] | Name |
| --- | --- |
| 16:0 | Palmitic acid |
| 16:1 | Palmitoleic acid |
| 16:3 | Roughanic acid |
| 18:0 | Stearic acid |
| 18:1 | Oleic acid |
| 18:2 | Linoleic acid |
| 18:3 | Linolenic acid |
| γ-18:3 | Gamma-linolenic acid* |
| 20:0 | Arachidic acid |
| 22:6 | Docosahexanoic acid (DHA)* |
| 20:2 | Eicosadienoic acid |
| 20:4 | Arachidonic acid (AA)* |
| 20:5 | Eicosapentaenoic acid (EPA)* |
| 22:1 | Erucic acid |

[1]Chain length: number of double bonds
*not naturally occurring in plants

Oils preferably relates to seed oils.

"Increase in" the total oil content refers to the increased oil content in a plant or a part, tissue or organ thereof, preferably in the seed organs of the plants. In this context, the oil content is at least 5%, preferably at least 10%, particularly preferably at least 15%, very particularly preferably at least 20%, most preferably at least 25% increased under otherwise identical conditions in comparison with a starting plant which has not been subjected to the method according to the invention, but is otherwise unmodified. Conditions in this context means all of the conditions which are relevant for germination, culture or growth of the plant, such as soil conditions, climatic conditions, light conditions, fertilization, irrigation, plant protection treatment and the like.

"Yeast glycerol 3-phosphate dehydrogenase" (termed "yeast G3PDH" hereinbelow) generally refers to all those enzymes which are capable of converting dihydroxyacetone phosphate (DHAP) into glycerol-3-phosphate (G3P)—preferably using a cosubstrate such as NADH—and which are naturally expressed in a yeast.

Yeast refers to the group of unicellular fungi with a pronounced cell wall and formation of pseudomycelium (in contrast to molds). They reproduce vegetatively by budding and/or fission (*Schizosaccharomyces* and *Saccharomycodes*, respectively).

Encompassed are what are known as false yeasts, preferably the families Cryptococcaceae, Sporobolomycetaceae with the genera *Cryptococcus, Torulopsis, Pityrosporum, Brettanomyces, Candida, Kloeckera, Trigonopsis, Trichosporon, Rhodotorula* and *Sporobolomyces* and *Bullera*, and true yeasts (yeasts which also reproduce sexually; ascus), preferably the families endo- and saccharomycetaceae, with the genera *Saccharomyces, Debaromyces, Lipomyces, Hansenula, Endomycopsis, Pichia, Hanseniaspora*. Most preferred are the genera *Saccharomyces cerevisiae, Pichia pastoris, Hansenula polymorpha, Schizosaccharomyces pombe, Kluyveromyces lactis, Zygosaccharomyces rouxii, Yarrowia lipolitica, Emericella nidulans, Aspergillus nidulans, Debaryomyces hansenii* and *Torulaspora hansenii*.

Yeast G3PDH refers in particular to polypeptides which have the following characteristics as "essential characteristics":

a) the conversion of dihydroxyacetone phosphate into glycerol-3-phosphate using NADH as cosubstrate (EC 1.1.1.8), and b) a peptide sequence encompassing at least one sequence motif selected from the group of sequence motifs consisting of

| i) | GSGNWGT(A/T)IAK | (SEQ ID NO: 22) |
| --- | --- | --- |
| ii) | CG(V/A)LSGAN(L/I/V)AXE(V/I)A | (SEQ ID NO: 26) |
| iii) | (L/V)FXRPYFXV | (SEQ ID NO: 27) | preferred is the sequence motif selected from the group consisting of

| iv) | GSGNWGTTIAKV(V/I)AEN | (SEQ ID NO: 29) |
| --- | --- | --- |
| v) | NT(K/R)HQNVKYLP | (SEQ ID NO: 30) |
| vi) | D(I/V)LVFN(I/V)PHQFL | (SEQ ID NO: 31) |
| vii) | RA(I/V)SCLKGFE | (SEQ ID NO: 32) |
| viii) | CGALSGANLA(P/T)EVA | (SEQ ID NO: 33) |
| ix) | LFHRPYFHV | (SEQ ID NO: 34) |
| x) | GLGEII(K/R)FG | (SEQ ID NO: 35) | the peptide sequence particularly preferably comprises at least 2 or 3, very particularly preferably at least 4 or 5, most preferably all of the sequence motifs selected from the group of the sequence motifs i), ii) and iii) or selected from the group of the sequence motifs iv), v), vi), vii), viii), ix) and xiv). (Terms in brackets refer to amino acids which are possible at this position as alternatives; for example (V/I) means that valin or isoleucin are possible at this position).

Moreover, a yeast G3PDH may optionally comprise—in addition to at least one of the abovementioned sequence motifs i) to x)—further sequence motifs selected from the group consisting of

| | | (SEQ ID NO: 23) |
| --- | --- | --- |
| xi) | H(E/Q)NVKYL | |
| | | (SEQ ID NO: 24) |
| xii) | (D/N)(I/V)(L/I)V(F/W)(V/N)(L/I/V)PHQF(V/L/I) | |
| | | (SEQ ID NO: 25) |
| xiii) | (A/G)(I/V)SC(L/I)KG | |
| | | (SEQ ID NO: 28) |
| xiv) | G(L/M)(L/G)E(M/I)(I/Q)(R/K/N)F(G/S/A) | |

Most preferably, yeast G3PDH refers to the yeast protein Gpdlp as shown in SEQ ID NO: 2 and functional equivalents or else functionally equivalent portions of the above.

Functional equivalents refers in particular to natural or artificial mutations of the yeast protein Gpdlp as shown in SEQ ID NO: 2 and homologous polypeptides from other yeasts which have the same essential characteristics of a yeast G3PDH as defined above. Mutations encompass substitutions, additions, deletions, inversions or insertions of one or more amino acid residues. Especially preferred are the polypeptides described by SEQ ID NO: 4, 5, 7, 9, 11, 12, 14, 16, 38 or 40.

The yeast G3PDH to be employed advantageously within the scope of the present invention can be found readily by database searches or by screening gene or cDNA libraries using the yeast G3PDH sequence shown in SEQ ID NO: 2, which is given by way of example, or the nucleic acid sequence as shown in SEQ ID NO: 1, which encodes the latter, as search sequence or probe.

Said functional equivalents preferably have at least 60%, particularly preferably at least 70%, particularly preferably at least 80%, most preferably at least 90% homology with the protein ith the SEQ ID NO: 2.

Homology between two polypeptides is understood as meaning the identity of the amino acid sequence over the entire sequence length which is calculated by comparison with the aid of the program algorithm GAP (Wisconsin Package Version 10.0, University of Wisconsin, Genetics Computer Group (GCG), Madison, USA), setting the following parameters:

Gap Weight: 8 Length Weight: 2
Average Match: 2,912 Average Mismatch: −2,003

For example, a sequence with at least 80% homology with the sequence SEQ ID NO: 2 at the protein level is understood as meaning a sequence which, upon comparison with the sequence SEQ ID NO: 2 with the above program algorithm and the above parameter set has at least 80% homology.

Functional equivalents also encompasses those proteins which are encoded by nucleic acid sequences which have at least 60%, particularly preferably at least 70%, particularly preferably at least 80%, most preferably at least 90% homology with the nucleic acid sequence with the SEQ ID NO: 1.

Homology between two nucleic acid sequences is understood as meaning the identity of the two nucleic acid sequences over the entire sequence length which is calculated by comparison with the aid of the program algorithm GAP (Wisconsin Package Version 10.0, University of Wisconsin, Genetics Computer Group (GCG), Madison, USA), setting the following parameters:

| Gap Weight: 50 | Length Weight: 3 |
| Average Match: 10 | Average Mismatch: 0 |

For example, a sequence which has at least 80% homology with the sequence SEQ ID NO: 1 at the nucleic acid level is understood as meaning a sequence which, upon comparison with the sequence SEQ ID NO: 1 with the above program algorithm with-the above. parameter set has a homology of at least 80%.

Functional equivalents also encompass those proteins which are encoded by nucleic acid sequences which hybridize under standard conditions with a nucleic acid sequence described by SEQ ID NO: 1, the nucleic acid sequence which is complementary thereto or parts of the above and which have the essential characteristics for a yeast G3PDH.

"Standard hybridization conditions" is to be understood in the broad sense, but preferably refers to stringent hybridization conditions. Such hybridization conditions are described, for example, by Sambrook J, Fritsch EF, Maniatis T et al., in Molecular Cloning (A Laboratory Manual), 2nd edition, Cold Spring Harbor Laboratory Press, 1989, pages 9.31-9.57) or in Current Protocols in Molecular Biology, John Wiley & Sons, N.Y. (1989), 6.3.1-6.3.6. For example, the conditions during the wash step can be selected from the range of high-stringency conditions (with approximately 0.2×SSC at 50° C., preferably at 65° C.) (20×SSC: 0.3 M sodium citrate, 3 M NaCl, pH 7.0). Denaturing agents such as, for example, formamide or SDS may also be employed during hybridization. In the presence of 50% formamide, hybridization is preferably carried out at 42° C.

The invention furthermore relates to transgenic expression constructs which can ensure a transgenic expression of a yeast G3PDH in a plant organism or a tissue, organ, part, cells or propagation material of said plant organism.

The definition given above applies to yeast G3PDH, with the transgenic expression of a yeast G3PDH described by the sequence with the SEQ ID NO: 2 being particularly preferred.

In said transgenic expression constructs, a nucleic acid molecule encoding a yeast G3PDH is preferably in operable linkage with at least one genetic control element (for example a promoter) which ensures expression in a plant organism or a tissue, organ, part, cell or propagation material of same.

Especially preferred are transgenic expression cassettes wherein the nucleic acid sequence encoding a glycerol-3-phosphate dehydrogenase is described by a) a sequence with the SEQ ID NO: 1, 3, 6, 8, 10, 13, 15, 37 or 39, or b) a sequence derived from a sequence with the SEQ ID NO: 1, 3, 6, 8, 10, 13, 15, 37 or 39 in accordance with the degeneracy of the genetic code c) a sequence which has at least 60% identity with the sequence with the SEQ ID NO: 1.

Operable linkage is understood as meaning, for example, the sequential arrangement of a promoter with the nucleic acid sequence encoding a yeast G3PDH which is to be expressed (for example the sequence as shown in SEQ ID NO: 1) and, if appropriate, further regulatory elements such as, for example, a terminator in such a way that each of the regulatory elements can fulfil its function when the nucleic acid sequence is expressed recombinantly. Direct linkage in the chemical sense is not necessarily required for this purpose. Genetic control sequences such as, for example, enhancer sequences can also exert their function on the target sequence from positions which are further removed or indeed from other DNA molecules. Preferred arrangements are those in which the nucleic acid sequence to be expressed recombinantly is positioned behind the sequence acting as promoter so that the two sequences are linked covalently to each other. The distance between the promoter sequence and the nucleic acid sequence to be expressed recombinantly is preferably less than 200 base pairs, particularly preferably less than 100 base pairs, very particularly preferably less than 50 base pairs.

Operable linkage and a transgenic expression cassette can both be effected by means of conventional recombination and cloning techniques as they are described, for example, in Maniatis T, Fritsch E F and Sambrook J (1989) Molecular Cloning: A Laboratory Manual, Cold Spring Harbor Laboratory, Cold Spring Harbor (N.Y.), in Silhavy T J, Berman M L und Enquist L W (1984) Experiments with Gene Fusions, Cold Spring Harbor Laboratory, Cold Spring Harbor (N.Y.), in Ausubel F M et al. (1987) Current Protocols in Molecular Biology, Greene Publishing Assoc. and Wiley Interscience and in Gelvin et al. (1990) In: Plant Molecular Biology Manual. However, further sequences which, for example, act as a linker with specific cleavage sites for restriction enzymes, or of a signal peptide, may also be positioned between the two sequences. Also, the insertion of sequences may lead to the expression of fusion proteins. Preferably, the expression cassette composed of a promoter linked to a nucleic acid sequence to be expressed can be in a vector-integrated form and can be inserted into a plant genome, for example by transformation.

However, a transgenic expression cassette is also understood as meaning those constructs where the nucleic acid sequence encoding a yeast G3PDH is placed behind an endogenous plant promoter in such a way that the latter brings about the expression of the yeast G3PDH.

Promoters which are preferably introduced into the transgenic expression cassettes are those which are operable in a plant organism or a tissue, organ, part, cell or propagation material of same. Promoters which are operable in plant organisms is understood as meaning any promoter which is capable of governing the expression of genes, in particular foreign genes, in plants or plant parts, plant cells, plant tissues or plant cultures. In this context, expression may be, for example, constitutive, inducible or development-dependent.

The following are preferred:

a) Constitutive promoters

"Constitutive" promoters refers to those-promoters which ensure expression in a large number of, preferably all, tissues over a substantial period of plant development, preferably at all times during plant development (Benfey et al.(1989) EMBO J 8:2195-2202). A plant promoter or promoter originating from a plant virus is especially preferably used. The promoter of the CaMV (cauliflower mosaic virus) 35S transcript (Franck et al. (1980) Cell 21:285-294; Odell et al. (1985) Nature 313:810-812; Shewmaker et al. (1985) Virology 140:281-288; Gardner et al. (1986) Plant Mol Biol 6:221- 228) or the 19S CaMV promoter (U.S. Pat. No. 5,352,605; WO 84/02913; Benfey et al. (1989) EMBO J 8:2195-2202) are especially preferred. Another suitable constitutive promoter is the Rubisco small subunit (SSU) promoter (U.S. Pat. No. 4,962,028), the leguminB promoter (GenBank Acc. No. X03677), the promoter of the nopalin synthase from *Agrobacterium*, the TR dual promoter, the OCS (octopine synthase) promoter from *Agrobacterium*, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits, the promoter of the *Arabidopsis thaliana* nitrilase-1 gene (GenBank Acc. No.: U38846, nucleotides 3862 to 5325 or else 5342) or the promoter of a proline-rich protein from wheat (WO 91/13991), and further promoters of genes whose constitutive expression in plants is known to the skilled worker. The CaMV 35S promoter and the *Arabidopsis thaliana* nitrilase-1 promoter are particularly preferred.

b) Tissue-specific promoters

Furthermore preferred are promoters with specificities for seeds, such as, for example, the phaseolin promoter (U.S. Pat. No. 5,504,200; Bustos M M et al. (1989) Plant Cell 1.(9):839-53), the promoter of the 2S albumin gene (Joseffson L G et al. (1987) J Biol Chem 262:12196-12201), the legumine promoter (Shirsat A et al. (1989) Mol Gen Genet 215(2):326-331), the USP (unknown seed protein) promoter (Bäumlein H et al. (1991) Mol Gen Genet 225(3):459-67), the napin gene promoter (U.S. Pat. No. 5,608,152; Stalberg K et al. (1996) L Planta 199:515-519), the promoter of the sucrose binding proteins (WO 00/26388) or the legumin B4 promoter (LeB4; Bäumlein H et al. (1991) Mol Gen Genet 225: 121-128; Bäumlein et al. (1992) Plant Journal 2(2):233-9; Fiedler U et al. (1995) Biotechnology (NY) 13(10);: 1090f), the *Arabidopsis oleosin* promoter (WO 98/45461), and the *Brassica* Bce4 promoter (Wo 91/13980).

Further suitable seed-specific promoters are those of the gene encoding high-molecular weight glutenin (HMWG), gliadin, branching enyzme, ADP glucose pyrophosphatase (AGPase) or starch synthase. Promoters which are furthermore preferred are those -which permit a seed-specific expression in monocots such as maize, barley, wheat, rye, rice and the like. The promoter of the lpt2 or lptl gene (WO 95/15389, WO 95/23230) or the promoters described in WO 99/16890 (promoters of the hordein gene, the glutelin gene, the oryzin gene, the prolamin gene, the gliadin gene, the glutelin gene, the zein gene, the casirin gene or the secalin gene) can advantageously be employed.

c) Chemically inducible promoters

The expression cassettes may also contain a chemically inducible promoter (review article: Gatz et al. (1997) Annu Rev Plant Physiol Plant Mol Biol 48:89-108), by means of which the expression of the exogenous gene in the plant can be controlled at a particular point in time. Such promoters such as, for example, the PRP1 promoter (Ward et al. (1993) Plant Mol Biol 22:361-366), a salicylic acid-inducible promoter (WO 95/19443), a benzenesulfonamide-inducible promoter (EP 0 388 186), a tetracyclin-inducible promoter (Gatz et al. (1992) Plant J 2:397-404), an abscisic acid-inducible promoter EP 0 335 528) or an ethanol-cyclohexanone-inducible promoter (WO 93/21334) can likewise be used. Also suitable is the promoter of the glutathione-S transferase isoform II gene (GST-II-27), which can be activated by exogenously applied safeners such as, for example, N,N-diallyl-2,2-dichloroacetamide (WO 93/01294) and which is operable in a large number of tissues of both monocots and dicots.

Particularly preferred are constitutive promoters, very particularly preferred seed-specific promoters, in particular the napin promoter and the USP promoter.

In addition, further promoters which make possible expression in further plant tissues or in other organisms such as, for example, *E. coli* bacteria, may be linked operably with the nucleic acid sequence-to be expressed. Suitable plant promoters are, in principle, all of the above-described promoters.

The nucleic acid sequences present in the transgenic expression cassettes according to the invention or transgenic vectors can be linked operably with further genetic control sequences besides a promoter. The term genetic control sequences is to be understood in the broad sense and refers to all those sequences which have an effect on the establishment or the function of the expression cassette according to the invention. Genetic control sequences modify, for example, transcription and translation in prokaryotic or eukaryotic organisms. The transgenic expression cassettes according to the invention preferably encompass a plant-specific promoter 5'-upstream of the nucleic acid sequence to be expressed recombinantly in each case and, as additional genetic control sequence, a terminator sequence 3'-downstream, and, if appropriate, further customary regulatory elements, in each case linked operably with the nucleic acid sequence to be expressed recombinantly.

Genetic control sequences also encompass further promoters, promoter elements or minimal promoters capable of modifying the expression-controlling properties. Thus, genetic control sequences can, for example, bring about tissue-specific expression which is additionally dependent on certain stress factors. Such elements are, for example, described for water stress, abscisic acid (Lam E and Chua N H, J Biol Chem 1991; 266(26): 17131-17135) and thermal stress (Schoffl F et al. (1989) Mol Gen Genetics 217(2-3): 246-53).

Further advantageous control sequences are, for example, in the Gram-positive promoters amy and SPO2, and in the yeast or fungal promoters ADC1, MFa, AC, P-60, CYC1, GAPDH, TEF, rp28, ADH.

In principle all natural promoters with their regulatory sequences like those mentioned above may be used for the method according to the invention. In addition, synthetic promoters may also be used advantageously.

Genetic control sequences further also encompass the 5'-untranslated regions, introns or nonencoding 3'-region of genes, such as, for example, the actin-1 intron, or the Adhl-S intron 1, 2 and 6 (for general reference, see: The Maize Handbook, Chapter 116, Freeling and Walbot, Eds., Springer, N.Y. (1994)). It has been demonstrated that these may play a significant role in regulating gene expression. Thus, it has been demonstrated that 5'-untranslated sequences can enhance the transient expression of heterologous genes. Translation enhancers which may be mentioned by way of example are the tobacco mosaic virus 5' leader sequence (Gallie et al. (1987) Nucl Acids Res 15:8693-8711) and the like. They may furthermore promote tissue specificity (Rouster J et al. (1998) Plant J 15:435-440).

The transient expression cassette can advantageously contain one or more of what are known as enhancer sequences in operable linkage with the promoter, and these make possible an increased recombinant expression of the nucleic acid sequence. Additional advantageous sequences such as further regulatory elements or terminators may also be inserted at the 3' end of the nucleic acid sequences to be expressed recombinantly. One or more copies of the nucleic acid sequences to be expressed recombinanly may be present in the gene construct.

Polyadenylation signals which are suitable as control sequences are plant polyadenylation signals, preferably those which correspond essentially to *Agrobacterium* tumefaciens T-DNA polyadenylation signals, in particular those of gene 3 of the T-DNA (octopine synthase) of the Ti plasmid pTiACHS (Gielen et al. (1984) EMBO J 3:835 et seq.) or functional equivalents thereof. Examples of particularly suitable terminator sequences are the OCS (octopin synthase) terminator and the NOS (nopaline synthase) terminator.

Control sequences are furthermore understood as those which make possible homologous recombination or insertion into the genome of a host organism, or removal from the genome. In the case of homologous recombination, for example, the coding sequence of the specific endogenous gene can be exchanged in a directed fashion for a sequence encoding a dsRNA. Methods such as the cre/lox technology permit the tissue-specific, possibly inducible, removal of the expression cassette from the genome of the host organism (Sauer B (1998) Methods. 14(4):381-92). Here, certain flanking sequences are added to the target gene (lox sequences), and these make possible removal by means of cre recombinase at a later point in time.

A recombinant expression cassette and the recombinant vectors derived from it may comprise further functional elements. The term functional element is to be understood in the broad sense and refers to all those elements which have an effect on generation, replication or function of the expression cassettes, vectors or transgenic organisms according to the invention.

Examples which may be mentioned, but not by way of limitation, are:

a) Selection markers which confer resistance to a metabolism inhibitor such as 2-deoxyglucose-6-phosphate (WO 98/45456), antibiotics or biocides, preferably herbicides, such as, for example, kanamycin, G 418, bleomycin, hygromycin, or phosphinothricin and the like. Particularly preferred selection markers are those which confer resistance to herbicides. The following may be mentioned by way of example: DNA sequences which encode phosphinothricin acetyltransferases (PAT) and which inactivate glutamine synthase inhibitors (bar and pat gene), 5-enolpyruvylshikimate-3-phosphate synthase genes (EPSP synthase genes), which confer resistance to Glyphosate® (N-(phosphonomethyl)glycine), the gox gene, which encodes Glyphosate®-degrading enzyme (Glyphosate oxidoreductase), the deh gene (encoding a dehalogenase which inactivates dalapon), sulfonylurea- and imidazolinone-inactivating acetolactate synthases, and bxn genes which encode nitrilase enzymes which degrade bromoxynil, the aasa gene, which confers resistance to the antibiotic apectinomycin, the streptomycin phosphotransferase (SPT) gene, which permits resistance to streptomycin, the neomycin phosphotransferase (NPTII) gene, which confers resistance to kanamycin or geneticidin, the hygromycin phosphotransferase (HPT) gene, which confers resistance to hygromycin, the acetolactate synthase gene (ALS), which confers resistance to sulfonylurea herbicides (for example mutated ALS variants with, for example, the S4 and/or Hra mutation).

b) Reporter genes which encode readily quantifiable proteins and which allow the transformation efficacy or the expression site or time to be assessed via their color or enzyme activity. Very particularly preferred in this context are reporter proteins (Schenborn E, Groskreutz D. Mol Biotechnol. 1999; 13(1):29-44) such as the "green fluorescence protein" (GFP) (Sheen et al.(1995) Plant Journal 8(5):777-784), chloramphenicol transferase, a luciferase (Ow et al. (1986) Science 234:856-859), the aequorin gene (Prasher et al. (1985) Biochem Biophys Res Commun 126 (3):1259-1268), β-galactosidase, with β-glucuronidase being very particularly preferred (Jefferson et al. (1987) EMBO J 6:3901-3907).

c) Replication origins which allow replication of the expression cassettes or vectors according to the invention in, for example, *E. coli*. Examples which may be mentioned are ORI (origin of DNA replication), the pBR322 ori or the P15A ori (Sambrook et al.: Molecular Cloning. A Laboratory Manual, 2nd ed. Cold Spring Harbor Laboratory Press, Cold Spring Harbor, N.Y., 1989).

d) Elements which are required for *agrobacterium*-mediated plant transformation such as, for example, the right or left border of the T-DNA, or the vir region.

To select cells which have successfully undergone homologous recombination or else cells which have succesfully been transformed, it is generally required additionally to introduce a selectable marker which confers resistance to a biocide (for example a herbicide), a metabolism inhibitor such as 2-deoxyglucose-6-phosphate (WO 98/45456) or an antibiotic to the cells which have successfully undergone recombination. The selection marker permits the selection of the transformed cells from untransformed cells (McCormick et al. (1986) Plant Cell Reports 5:81-84).

In addition, said recombinant expression cassette or vectors may comprise further nucleic acid sequences which do not encode a yeast G3PDH and whose recombinant expression leads to a further increase in fatty acid biosynthesis (as a consequence of proOIL). By way of example, but not by limitation, this proOIL nucleic acid sequence which is additionally expressed recombinantly can be selected from among nucleic acids encoding acetyl-COA carboxylase (AC-Case), glycerol-3-phosphate acyltransferase (GPAT), lysophosphatidate acyltransferase (LPAT), diacylglycerol acyltransferase (DAGAT) and phospholipid:diacylglycerol acyltransferase (PDAT). Such sequences are known to the skilled worker and are readily accessible from databases or suitable cDNA libraries of the respective plants.

An expression cassette according to the invention can advantageously be introduced into an organism or cells, tissues, organs, parts or seeds thereof (preferably into plants or plant cells, tissues, organs, parts or seeds) by using vectors in which the recombinant expression cassettes are present. The invention therefore furthermore relates to said recombinant vectors which encompass a recombinant expression cassette for a yeast G3PDH.

For example, vectors may be plasmids, cosmids, phages, viruses or else agrobacteria. The expression cassette can be introduced into the vector (preferably a plasmid vector) via a suitable restriction cleavage site. The resulting vector is first introduced into *E. coli*. Correctly transformed *E. coli* are selected, grown, and the recombinant vector is obtained with methods known to the skilled worker. Restriction analysis and sequencing may be used for verifying the cloning step. Preferred vectors are those which make possible stable integration of the expression cassette into the host genome.

The invention furthermore relates to transgenic plant organisms or tissues, organs, parts, cells or propagation material thereof which comprise a yeast G3PDH as defined above, a transgenic expression cassette for a yeast G3PDH or a transgenic vector encompassing such an expression cassette.

Such a transgenic plant organism is generated, for example, by means of transformation or transfection by means of the corresponding proteins or nucleic acids. The generation of a transformed organism (or a transformed cell or tissue) requires introducing the DNA in question (for example the expression vector), RNA or protein into the host cell in question. A multiplicity of methods is available for this procedure, which is termed transformation (or transduction or transfection) (Keown et al. (1990) Methods in Enzymology 185:527-537). Thus, the DNA or RNA can be introduced for example directly by microinjection or by bombardment with-DNA-coated microparticles. The cell may also be permeabilized chemically, for example with polyethylene glycol, so that the DNA may reach the cell by diffusion. The DNA can also be carried out by protoplast fusion with other DNA-comprising units such as minicells, cells, lysosomes or liposomes. Electroporation is a further suitable method for introducing DNA; here, the cells are permeabilized reversibly by an electrical pulse. Soaking plant parts in DNA solutions, and pollen or pollen tube transformation, are also possible. Such methods have been described (for example in Bilang et al. (1991) Gene 100:247-250; Scheid et al. (1991) Mol Gen Genet 228:104-112; Guerche et al. (-1987) Plant Science 52:111-116; Neuhause et al. (1987) Theor Appl Genet 75:30-36; Klein et al. (1987) Nature 327:70-73; Howell et al. (1980) Science 208:1265; Horsch et al.(1985) Science 227:1229-1231; DeBlock et al. (1989) Plant Physiology 91:694-701; Methods for Plant Molecular Biology (Weissbach and Weissbach, eds.) Academic Press Inc. (1988); and Methods in Plant Molecular Biology (Schuler and Zielinski, eds.) Academic Press Inc. (1989)).

In plants, the methods which have been described for transforming and regenerating plants from plant tissues or plant cells are exploited for transient or stable transformation. Suitable methods are, in particular, protoplast transformation by polyethylene glycol-induced DNA uptake, the biolistic method with the gene gun, what is known as the particle bombardment method, electroporation, the incubation of dry embryos in DNA-containing solution, and microinjection.

In addition to these "direct" transformation techniques, transformation may also be effected by bacterial infection by means of *Agrobacterium tumefaciens* or *Agrobacterium rhizogenes* and the transfer of corresponding recombinant Ti plasmids or Ri plasmids by or by infection with transgenic plant viruses. *Agrobacterium*-mediated transformation is best suited to cells of dicotyledonous plants. The methods are described, for example, in Horsch R B et al. (1985) Science 225: 1229f).

When agrobacteria are used, the expression cassette is to be integrated into specific plasmids, either into a shuttle vector or into a binary vector. If a Ti or Ri plasmid is to be used for the transformation, at least the right border, but in most cases the right and left border, of the Ti or Ri plasmid T-DNA is linked to the expression cassette to be introduced as flanking region.

Binary vectors are preferably used. Binary vectors are capable of replication both in *E. coli* and in *Agrobacterium*. As a rule, they contain a selection marker gene and a linker or polylinker flanked by the right and left T-DNA border sequence. They can be transformed directly into *Agrobacterium* (Holsters et al. (1978) Mol Gen Genet 163:181-187). The selection marker gene, which is, for example, the nptII gene, which confers resistance to kanamycin, permits a selection of transformed agrobacteria. The agrobacterium which acts as host organism in this case should already contain a plasmid with the vir region. The latter is required for transferring-the T-DNA to the plant cells. An *agrobacterium* transformed in this way can be used for transforming plant cells. The use of T-DNA for the transformation of plant cells has been studied intensively and described (EP 120 516; Hoekema, In: The Binary Plant Vector System, Offsetdrukkerij. Kanters B. V., Alblasserdam, Chapter V; An et al. (1985) EMBO J 4:277-287). Various binary vectors, some of which are commercially available, such as, for example, pBI101.2 or pBIN19 (Clontech Laboratories, Inc. USA), are known.

Further promoters which are suitable for expression in plants have been described (Rogers et al. (1987) Meth in Enzymol 153:253-277; Schardl et al. (1987) Gene 61:1-11; Berger et al. (1989) Proc Natl Acad Sci USA 86:8402-8406).

Direct transformation techniques are suitable for any organism and cell type. In cases where DNA or RNA are injected or electroporated into plant cells, the plasmid used need not meet any particular requirements. Simple plasmids such as those from the pUC series may be used. If intact plants are to be regenerated from the transformed cells, it is necessary for an additional selectable marker gene to be present on the plasmid. Stably transformed cells, i.e. those which contain the inserted DNA integrated into the DNA of the host cell, can be selected from untransformed cells when a selectable marker is part of the inserted DNA. By way of example, any gene which is capable of conferring resistance to antibiotics or herbicides (such as kanamycin, G418, bleomycin, hygromycin or phosphinothricin and the like) is capable of acting as marker (see above). Transformed cells which express such a marker gene are capable of surviving in the presence of concentrations of such an antibiotic or herbicide which kill an untransformed wild type. Examples are mentioned above and preferably comprise the bar gene, which confers resistance to the herbicide phosphinothricin (Rathore K S et al. (1993.) Plant Mol Biol 21(5):871-884), the nptII gene, which confers resistance to kanamycin, the hpt gene, which confers resistance to hygromycin, or the EPSP gene, which confers resistance to the herbicide Glyphosate. The selection marker permits selection of transformed cells from untransformed cells (McCormick et al. (1986) Plant Cell Reports 5:81-84). The plants obtained can be bred and hybridized in the customary manner. Two or more generations should be grown in order to ensure that the genomic integration is stable and hereditary.

The above-described methods are described, for example, in Jenes B et al.(.1993) Techniques for Gene Transfer, in: Transgenic Plants, Vol. 1, Engineering and Utilization, edited by S D Kung and R Wu, Academic Press, pp.128-143, and in Potrykus (1991) Annu Rev Plant Physiol Plant Molec Biol 42:205-225). The construct to be expressed is preferably cloned into a vector which is suitable for transforming *Agrobacterium tumefaciens*, for example pBin19 (Bevan et al. (1984) Nucl Acids Res 12:8711f).

Once a transformed plant cell has been generated, an intact plant can be obtained using methods known to the skilled worker. For example, callus cultures are used as starting material. The development of shoot and root can be induced in this as yet undifferentiated cell biomass in the known fashion. The plantlets obtained can be planted out and used for breeding.

The skilled worker is familiar-with such methods for regenerating plant parts and intact plants from plant cells. Methods which can be used for this purpose are, for example, those described by Fennell et al. (1992) Plant Cell Rep. 11: 567-570; Stoeger et al (1995) Plant Cell Rep. 14:273-278; Jahne et al. (1994) Theor Appl Genet 89:525-533.

"Transgenic", for example in the case of a yeast G3PDH, refers to a nucleic acid sequence, an expression cassette or a vector comprising said G3PDH nucleic acid sequence or to an organism transformed with said nucleic acid sequence, expression cassette or vector all those constructs established by recombinant methods in which either
a) the nucleic acid sequence encoding a yeast G3PDH or
b) a genetic control sequence, for example a promoter which is functional in plant organisms, which is linked operably with said nucleic acid sequence under a), or
c) (a) and (b)

are not in their natural genetic environment or have been modified by recombinant methods, it being possible for the modification to be, for example, a substitution, addition, deletion, inversion or insertion of one or more nucleotide residues. Natural genetic environment refers to the natural chromosomal locus in the source organism or the presence in a genomic library. In the case of a genomic library, the natural genetic environment of the nucleic acid sequence is preferably retained, at least to some extent. The environment flanks the nucleic acid sequence at least on one side and has a sequence length of at least 50 bp, preferably at least 500 bp, particularly preferably at least 1000 bp, very particularly preferably at least 5000 bp. A naturally occurring expression cassette, for example the naturally occurring combination of the promoter of a gene encoding for a yeast G3PDH with the corresponding yeast G3PDH gene, becomes a transgenic expression cassette when the latter is modified by non-natural, synthetic ("artificial") methods such as, for example, a mutagenization. Such methods are described (U.S. Pat. No. 5,565,350; WO 00/15815; see also above).

Host or starting organisms which are preferred as transgenic organisms are, above all, plants in accordance with the above definition. Included for the purposes of the invention are all genera and species of higher and lower plants of the Plant Kingdom, in particular plants which are used for obtaining oils, such as, for example, oilseed rape, sunflower, sesame, safflower, olive tree, soya, maize, wheat and nut species. Furthermore included are the mature plants, seed, shoots and seedlings, and parts, propagation material and cultures, for example cell cultures, derived therefrom. Mature plants refers to plants at any desired developmental stage beyond the seedling stage. Seedling refers to a young, immature plant at an early developmental stage.

The transgenic organisms can be generated with the above-described methods for the transformation or transfection of organisms.

The invention furthermore relates to the use of the transgenic organisms according to the invention and to the cells, cell cultures, parts—such as, for example, in the case of transgenic plant organisms roots, leaves and the like—and transgenic propagation material such as seeds or fruits which are derived therefrom for the production of foodstuffs or feedstuffs, pharmaceuticals or fine chemicals, in particular oils, fats, fatty acids or derivatives of these.

Besides influencing the oil content, the transgenic expression of a yeast G3PDH in plants may mediate yet further advantageous effects such as, for example, an increased stress resistance to, for example, osmotic stress. Via increased glycerol levels, the yeast G3PDH confers protection against this type of stress, with glycerol acting as osmoprotective substance. Such osmotic stress occurs for example in saline soils and water and is an increasing problem in agriculture. Increased stress tolerance makes it possible, for example, to use areas in which conventional arable plants are not capable of thriving for agricultural usage.

Furthermore, recombinant expression of the yeast G3PDH can influence the NADH level and thus the redox balance in the plant organism. Stress such as, for example, drought, high or low temperatures, UV light and the like can lead to increased NADH levels and to an increased formation of reactive oxygen (RO). Transgenic expression of the yeast G3PDH can break down excessive NADH, which accumulates under said stress conditions, and thus stabilize the redox balance and alleviate the effects of the stress.

Sequences
1. SEQ ID NO: 1
   Nucleic acid sequence encoding *Saccharomyces cerevisiae* G3PDH (Gpd1p)
2. SEQ ID NO: 2
   Protein sequence encoding *Saccharomyces cerevisiae* G3PDH (Gpd1p)
3. SEQ ID NO: 3
   Nucleic acid sequence encoding *Saccharomyces cerevisiae* G3PDH (Gpd2p)
4. SEQ ID NO: 4
   Protein sequence encoding *Saccharomyces cerevisiae* G3PDH (Gpd2p)
5. SEQ ID NO: 5
   Protein sequence encoding *Saccharomyces cerevisiae* G3PDH (Gpd2p) with second alternative start codon
6. SEQ ID NO: 6
   Nucleic acid sequence encoding *Schizosaccharomyces pombe* G3PDH
7. SEQ ID NO: 7
   Protein sequence encoding *Schizosaccharomyces pombe* G3PDHD 8. SEQ ID NO: 8
   Nucleic acid sequence encoding *Schizosaccharomyces pombe* G3PDH
9. SEQ ID NO: 9
   Protein sequence encoding *Schizosaccharomyces pombe* G3PDH
10. SEQ ID NO: 10
    Nucleic acid sequence encoding *Yarrowinia lipolytica* G3PDH
11. SEQ ID NO: 11
    Protein sequence encoding *Yarrowinia lipolytica* G3PDH
12. SEQ ID NO: 12
    Protein sequence encoding *Yarrowinia lipolytica* G3PDH, with second alternative start codon
13. SEQ ID NO: 13
    Nucleic acid sequence encoding *Zygosaccharomyces rouxii* G3PDH
14. SEQ ID NO: 14
    Protein sequence encoding *Zygosaccharomyces rouxii* G3PDH
15. SEQ ID NO: 15
    Nucleic acid sequence encoding *Zygosaccharomyces rouxii* G3PDH
16. SEQ ID NO: 16
    Protein sequence encoding *Zygosaccharomyces rouxii* G3PDH
17. SEQ ID NO: 16
    Expression vector based on pSUN-USP for *S. cerevisiae* G3PDH (Gpd1p; 1017-2190 bp insert)

18. SEQ ID NO: 18  Oligonucleotide primer ONP1
    5'-ACTAGTATGTCTGCTGCTGCTGATAG-3'

19. SEQ ID NO: 19  Oligonucleotide primer ONP2
    5'-CTCGAGATCTTCATGTAGATCTAATT-3'

20. SEQ ID NO: 20  Oligonucleotide primer ONP3
    5'-GCGGCCGCCATGTCTGCTGCTGCTGATAG-3'

21. SEQ ID NO: 21  Oligonucleotide primer ONP4
    5'-GCGGCCGCATCTTCATGTAGATCTAATT-3'

22-35: SEQ ID NP 22 to 35: Sequence motifs for yeast G3PDHs;
possible sequence variations are given. The variations of an individual motif may occur in each case alone, but also in the different combinations with each other.

36. SEQ ID NO: 36
    Expression vector pGPTV-gpd1 based on pGPTV-napin for *S. cerevisiae* G3PDH (Gpd1p; gdp1 insert of 11962-13137 bp; nos terminator: 13154-13408; napin promoter: 10807-11951).
37. SEQ ID NO: 37
    Nucleic acid sequence encoding *Emericella nidulans* G3PDH
38. SEQ ID NO: 38
    Amino acid encoding *Emericella nidulans* G3PDH
39. SEQ ID NO: 39
    Nucleic acid sequence encoding *Debaryomyces hansenii* G3PDH (partial)
40. SEQ ID NO: 40
    Amino acid encoding *Debaryomyces hansenii* G3PDH (partial)

FIGURES

FIG. 1: Oil content in transgenic GPD1p lines

Measurement of the TAG content in T2 seeds of transgenic *Arabidopsis* lines with the *Saccharomyces cerevisiae* Gpd1p gene (G2 to G30). The content in corresponding untransformed plants (wild-type plants; W1 to W10) has been determined for comparison. 8 *Arabidopsis* lines with a significantly increased oil content were identified. The error deviation stated is the result of 3 independent measurements in each case.

Figure 2:
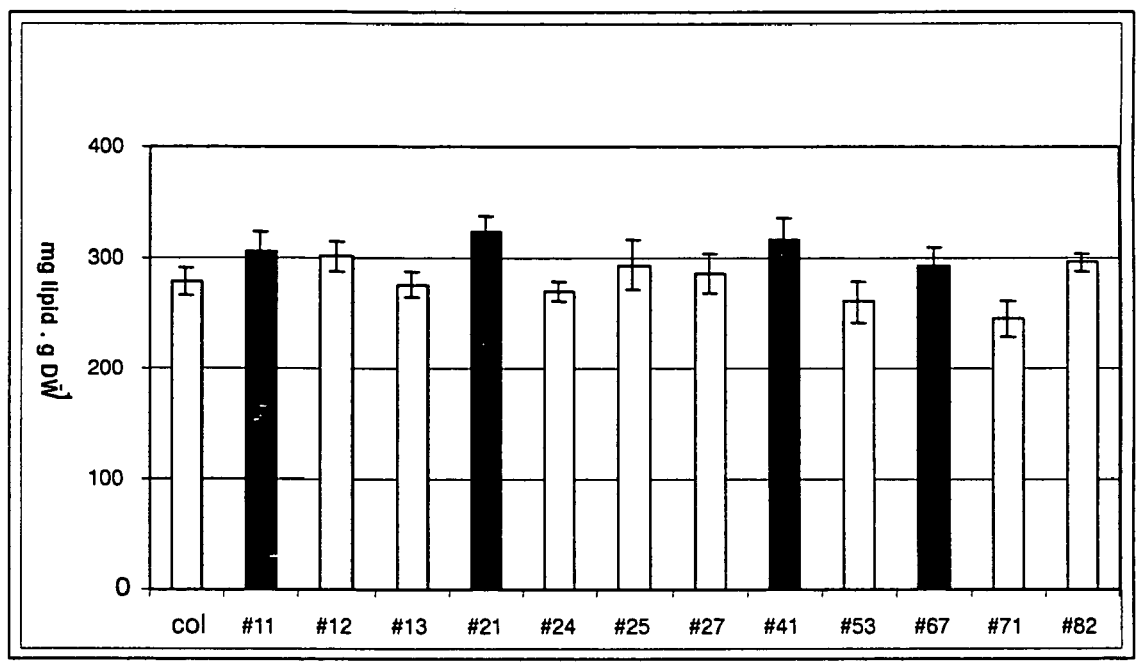
FIG. 2. Determination of oil content in seeds of T3 generation.

FIG. 2: Determination of the oil content in seeds of the T3 generation

The data shown are the oil content (in mg lipid per g dry matter (DM)) of individual *Arabidopsis* lines. Each column represents the mean of 6 individual plants per independent line. Each plant was analysed in triplicate. The error bars denote the standard deviation over all values. The control plants are identified by "col". The numerical values of the individual data are additionally shown in the following table (the control was set as 100% oil content):

| Lines | Oil content (mg/g) | STD | Rel. increase in % |
|---|---|---|---|
| col | 278.1 | 12.2 | 100 |
| #11 | 304.6 | 18.3 | 110 |
| #12 | 301.4 | 19.0 | 108 |
| #13 | 275.2 | 89.7 | 99 |
| #21 | 323.2 | 77.0 | 116 |
| #24 | 268.9 | 15.1 | 97 |
| #25 | 293.6 | 23.0 | 106 |
| #27 | 285.6 | 18.4 | 103 |
| #41 | 316.1 | 19.1 | 114 |
| #53 | 260.3 | 16.4 | 94 |
| #67 | 292.0 | 13.8 | 105 |
| #71 | 244.1 | 11.6 | 88 |
| #82 | 295.6 | 16.8 | 106 |

Lines with a statistically significantly increased lipid content (lines #11, #21, #41 and #67) are presented as a black bar.

Figure 3:
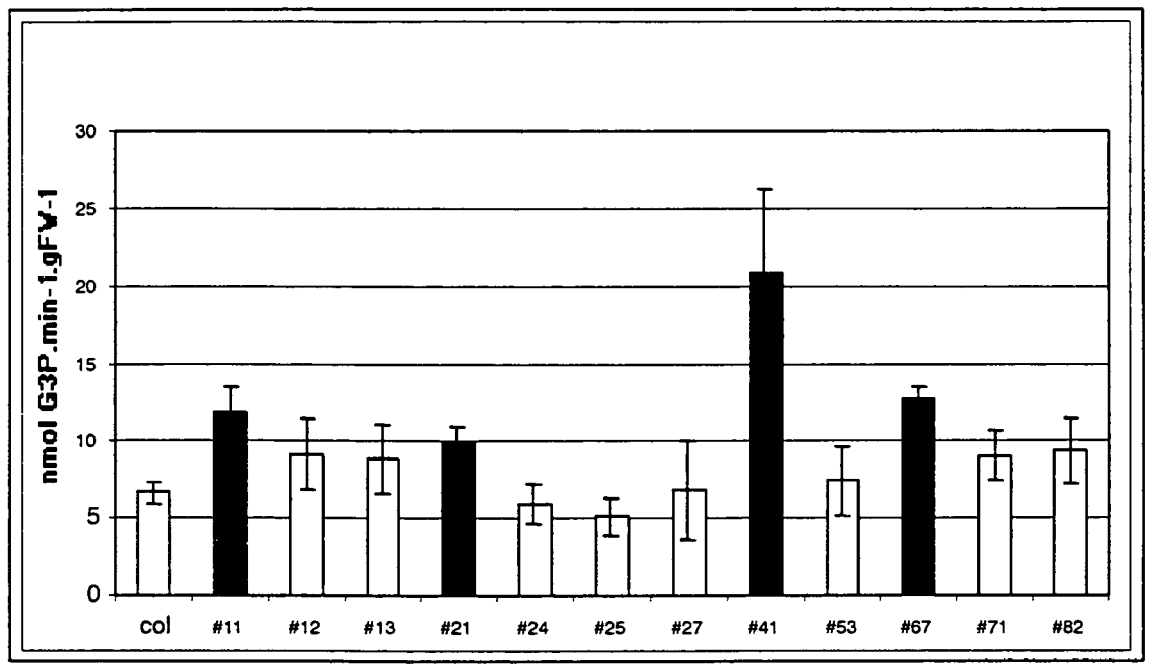
FIG. 3. Determination of the G3PDH activity in control and gdp1-transformed plants.

FIG. 3: Determination of the G3PDH activity in the control ("col") and the gdp1-transformed plants.

The G3PDG activity of the individual lines was determined as decribed in Example 8 and is shown in nmol G3P per minute per g of fresh weight (FW).

| | G3PDH Activity | STD |
|---|---|---|
| col | 6.68337432 | 0.71785229 |
| #11 | 11.8958635 | 1.67941604 |
| #12 | 9.14226124 | 2.25411878 |
| #13 | 8.8210768 | 2.19519777 |
| #21 | 9.88435444 | 1.04798566 |
| #24 | 5.89378595 | 1.26005769 |
| #25 | 5.14179348 | 1.22845409 |
| #27 | 6.77303725 | 3.22220935 |
| #41 | 20.8325636 | 5.42018531 |
| #53 | 7.45794947 | 2.25573816 |
| #67 | 12.7670015 | 0.74678353 |
| #71 | 9.04748534 | 1.59829185 |
| #82 | 9.37260033 | 2.1356558 |

Lines with a statistically significantly increased G3PDH activity (lines #11, #21, #41 and #67) are presented as a black bar. It can be seen that an increased G3PDG activity correlates with an increased lipid content.

EXAMPLES

General Methods

Unless otherwise specified, all chemicals were from Fluka (Buchs), Merck (Darmstadt), Roth (Karlsruhe), Serva (Heidelberg) and Sigma (Deisenhofen). Restriction enzymes, DNA-modifying enzymes and molecular biological kits were from Amersham-Pharmacia (Freiburg), Biometra (Gbttingen), Roche (Mannheim), New England Biolabs (Schwalbach), Novagen (Madison, Wis., USA), Perkin-Elmer (Weiterstadt), Qiagen (Hilden), Stratagen (Amsterdam, Netherlands), Invitrogen (Karlsruhe) and Ambion (Cambridgeshire, United Kingdom). The reagents used were employed in accordance with the manufacturer's instructions.

For example, oligonucleotides can be synthesized chemically in the known manner using the phosphoamidite method (Voet, Voet, 2nd edition, Wiley Press New York, pages 896-897). The cloning steps carried out for the purposes of the present invention such as, for example, restriction cleavages, agarose gel electrophoreses, purification of DNA fragments, transfer of nucleic acids to nitrocellulose and nylon membranes, linking DNA fragments, transformation of *E. coli* cells, bacterial cultures, multiplication of phages and sequence analysis of recombinant DNA, are carried out as decribed by Sambrook et al. (1989) Cold Spring Harbor Laboratory Press; ISBN 0-87969-309-6. Recombinant DNA molecules were sequenced using an ABI laser fluorescence DNA sequencer following the method of Sanger (Sanger et al. (1977) Proc Natl Acad Sci USA 74:5463-5467).

Example 1

General Methods

The plant *Arabidopsis thaliana* belongs to the higher plants (flowering plants). This plant is closely related to other plant species from-the Cruciferae family such as, for example, *Brassica napus*, but also to other families of dicotyledonous plants. Owing to the high degree of homology of its DNA sequences or its polypeptide sequences, *Arabidopsis thaliana* can be employed as model plant for other plant species.

a) Culture of *Arabidopsis* plants

The plants are grown either on Murashige-Skoog medium supplemented with 0.5% sucrose (Ogas et al. (1997) Science 277:91-94) or in soil (Focks & Benning (1998) Plant Physiol 118:91-101). To achieve uniform germination and flowering times, the seeds are first placed on medium or scattered on the soil and then stratified for two days at 4° C. After flowering, the pods are labeled. According to the labels, pods aged 6 to 20 days post-anthesis are then harvested.

Example 2

Cloning the Yeast Gpd1 Gene

Genomic DNA from *Saccharomyces cerevisiae* strain S288C (Mat alpha. SUC2 mal mel gal2 CUP1 flo1 flo8-1; Invitrogen, Karlsruhe, Germany) was isolated following the protocol described hereinbelow:

A 100 ml culture was grown at 30° C. to an optical density of 1.0. 60 ml of the culture were spun down for 3 minutes at 3000×g. The pellet was resuspended in 6 ml of twice-distilled $H_2O$ and the suspension was divided between 1.5 ml containers and spun down, and the supernatant was discarded. The pellets were resuspended in 200 µl of solution A, 200 µl phenol/chloroform (1:1) and 0.3 g of glass beads by vortexing and then lysed. After addition of 200 µl of TE buffer, pH 8.0, the lysates were spun for 5 minutes. The supernatant was subjected to ethanol precipitation with 1 ml of ethanol. After the precipitation, the resulting pellet was dissolved in 400 µl of TE buffer pH 8.0+30 µg/ml RNase A. Following incubation for 5 minutes at 37° C., 18 µl 3 M sodium acetate solution pH 4.8 and 1 ml of ethanol were added, and the precipitated DNA was pelleted by spinning. The DNA pellet was dissolved in 25 µl of twice-distilled $H_2O$. The concentration of the genomic DNA was determined by its absorption at 260 nm.

Solution A:
2% Trition-X100
1% SDS
0.1 M NaCl
0.01 M Tris-HCl pH 8.0
0.001 M EDTA To clone the Gpd1 gene, the yeast DNA which has been isolated was employed in a PCR reaction with the oligonucleotide primers ONP1 and ONP2.

```
ONP1:
5'-ACTAGTATGTCTGCTGCTGCTGATAG-3'   (SEQ ID NO: 18)

ONP2:
5'-CTCGAGATCTTCATGTAGATCTAATT-3'  (SEQ ID NO: 19)
```

Composition of the PCR reaction (50 µl):
5.00 µl 5 µg genomic yeast-DNA
5.00 µl 10× buffer (Advantage polymerase)+25 mM $MgCl_2$
5.00 µl 2 mM dNTP
1.25 µl each primer (10 pmol/uL)
0.50 µl Advantage polymerase The Advantage polymerase employed was from Clontech.

PCR-Program:
Initial denaturation for 2 min at 95° C., then 35 cycles of 45 sec at 95° C., 45 sec at 55° C. and 2 min at 72° C. Final extension for 5 min at 72° C.

The PCR products were cloned into the vector pCR2.1-TOPO (Invitrogen) following the manufacturer's instructions, resulting in the vector pCR2.1-gpd1, and the sequence was verified by sequencing.

Cloning into the agro transformation vector PGPTV involved incubating 0.5 µg of the vector pCR2.1-gpd1 with the restriction enzyme XhoI (New England Biolabs) for 2 hours and subsequent incubation for 15 minutes with Klenow fragment (New England Biolabs). After incubation for 2 hours with SpeI, the DNA fragments were separated by gel electrophoresis. The 1185 bp segment of the gpd1 sequence next to the vector (3.9 kb) was excized from the gel, purified with the "Gel Purification" kit from Qiagen following the manufacturer's instructions and eluted with 50 µl of elution buffer. 0.1 µg of the vector PGPTV was first digested for 1 hour with the restriction enzyme SacI and then incubated for 15 minutes with Klenow fragment (New England Biolabs). 10 µl of the eluate of the gpdl fragments and 10 ng of the treated pGPTV vector were ligated overnight at 16° C. (T4 ligase, New England Biolabs). The ligation products were then transformed into TOP10 cells (Stratagene) following the manufacturer's instructions and suitably selected, resulting in the vector pGPTV-gpd1. Positive clones are verified by sequencing and PCR using the primers ONP1 and ONP2.

To generate the vector pSUN-USP-gpd1, a PCR was carried out with the vector pCR2.1-gpd1 using the primers ONP3 and ONP4.

```
                                        (SEQ ID NO: 20)
ONP3:    5'-GCGGCCGCCATGTCTGCTGCTGCTGATAG-3'

(SEQ ID NO: 21)
ONP4:    5'-GCGGCCGCATCTTCATGTAGATCTAATT-3'
```

Composition of the PCR reaction (50 µl):

5 ng DNA plasmid pCR2.1-gpd1

5.00 µl 10× buffer (Advantage polymerase)+25 mM MgCl$_2$ 5.00 µl 2 mM dNTP 1.25 µl each primer (10 pmol/uL)

0.50 µl Advantage polymerase

The Advantage polymerase employed was from Clontech.

PCR-Program:

Initial denaturation for 2 min at 95° C., then 35 cycles of 45 sec at 95° C., 45 sec at 55° C. and 2 min at 72° C. Final extension for 5 min at 72° C.

The 1190 bp PCR product was digested for 24 hours with the restriction enzyme NotI. The vector pSUN-USP was digested for 2 hours with NotI and then incubated for 15 minutes with alkaline phosphatase (New England Biolabs). 100 ng of the pretreated gpd1 fragment and 10 ng of the treated vector PGPTV were ligated overnight at 16° C. (T4 Ligase from New England Biolabs). The ligation products were then transformed into TOP10 cells (Stratagene) following the manufacturer's instructions and suitably selected, resulting in the vector pSUN-USP-gpd1. Positive clones are verified by sequencing and PCR using the primers ONP3 and ONP4.

Example 3

Plasmids for the Transformation of Plants

Binary vectors such as pBinAR can be used for the transformation of plants (Höfgen und Willmitzer (1990) Plant Science 66: 221-230). The binary vectors can be constructed by ligating the cDNA into T-DNA in sense and antisense orientation. 5' of the cDNA, a plant promoter activates the transcription of the cDNA. A polyadenylation sequence is located 3' of the cDNA.

Tissue-specific expression can be achieved using a tissue-specific promoter. For example, seed-specific expression can be achieved by cloning in the napin or the LeB4- or the USP promoter 5' of the cDNA. Any other seed-specific promoter element can also be used. The CaMV 35S promoter can be used for constitutive expression in the whole plant.

A further example of binary vectors is the vector pSUN-USP and pGPTV-napin, into which the fragment of Example 2 was cloned. The vector pSUN-USP contains the USP promoter and the OCS terminator. The vector pGPTV-napin contains a truncated version of the napin promoter, and the nos terminator.

The fragments of Example 2 were cloned into the multiple cloning site of the vector pSUN-USP and pGPTV-napin respectively, to make possible the seed-specific expression of the gdpl gene. The corresponding construct pSUN-USP-gpd1 is described with the SEQ ID NO: 17, and the construct of G3PDH in pGPTV-napin (pGPTV-gpd1) by SEQ ID NO: 36.

Example 4

Transformation of *Agrobacterium*

*Agrobacterium*-mediated plant transformation can be carried out for example using the *Agrobacterium tumefaciens* strains GV3101 (pMP90) (Koncz und Schell (1986) Mol Gen Genet 204: 383-396) or LBA4404 (Clontech). Standard transformation techniques may be used for the transformation (Deblaere et al.(1984) Nucl Acids Res 13:4777-4788).

Example 5

Transformation of Plants

*Agrobacterium*-mediated plant transformation can be effected using standard transformation and regeneration techniques (Gelvin S B, Schilperoort R, Plant Molecular Biology Manual, 2nd ed., Dordrecht: Kluwer Academic Publ., 1995, in Sect, Ringbuch Zentrale Signatur: BT11-P ISBN 0-7923-2731-4; Glick B R, Thompson J E, Methods in Plant Molecular Biology and Biotechnology, Boca Raton: CRC Press, 1993, 360 pp., ISBN 0-8493-5164-2).

The transformation of *Arabidopsis thaliana* by means of *Agrobacterium* was carried out by the method of Bechthold et al., 1993 (C.R. Acad. Sci. Ser. III Sci. Vie., 316, 1194-1199). For example, oilseed rape can be transformed by cotyledon or hypocotyl transformation (Moloney et al.(1989) Plant Cell Report 8:238-242; De Block et al.(1989) Plant Physiol 91: 694-701). The use of antibiotics for the selection of agrobacteria and plants depends on the binary vector used for the transformation and the agrobacterial strain. The selection of oilseed rape is usually carried out using kanamycin as-selectable plant marker.

*Agrobacterium*-mediated gene transfer into linseed (*Linum usitatissimum*) can be carried out for example using a technique described by Mlynarova et al. (1994) Plant Cell Report 13:282-285. Soya can be transformed for example using a technique described in EP-A-0 0424 047 (Pioneer Hi-Bred International) or in EP-A-0 0397 687, U.S. Pat. No. 5,376, 543, U.S. Pat. No. 5,169,770 (University of Toledo).

The transformation of plants using particle bombardment, polyethylene glycol mediated DNA uptake or via the silicon carbonate fiber technique is described, for example, by Freeling and Walbot "The Maize Handbook" (1993) ISBN 3-540-97826-7, Springer Verlag New York).

Example 6

Studying the Expression of a Recombinant Gene Product in a Transformed Organism

The activity of a recombinant gene product in the transformed host organism was measured at the transcription and/or translation level.

A suitable method for determining the level of transcription of the gene (which indicates the amount of RNA available for translating the gene product) is to carry out a Northern blot as described hereinbelow (for reference see Ausubel et al. (1988) Current Protocols in Molecular Biology, Wiley: N.Y., or the above examples section), where a primer which is designed such that it binds to the gene of interest is labeled with a detectable label (usually a radiolabel or chemiluminescent label) so that, when the total RNA of a culture of the organism is extracted, separated on a gel, transferred to a stable matrix and incubated with this probe, binding and the extent of binding of the probe indicates the presence and the amount of mRNA for this gene. This information indicates the degree of transcription of the transformed gene. Cellular total RNA can be prepared from cells, tissues or organs using several methods, all of which are known in the art, for example the method Bormann, E. R., et al. (1992) Mol. Microbiol. 6:317-326.

Northern Hybridization:

To carry out the RNA hybridization, 20 µg of total RNA or 1 µg of poly(A)+RNA were separated by means of gel electrophoresis in 1.25% strength agarose gels using formaldehyde and following the method described by Amasino (1986, Anal. Biochem. 152, 304), transferred to positively charged nylon membranes (Hybond N+, Amersham, Brunswick) by capillary force using 10×SSC, immobilized by UV light and prehybridized for 3 hours at 68° C. using hybridization buffer (10% dextran sulfate w/v, 1 M NaCl, 1% SDS, 100 mg herring sperm DNA). The DNA probe was labeled with the Highprime DNA labeling kit (Roche, Mannheim, Germany) during the prehybridization step, using alpha-$^{32}$P-dCTP (Amersham Pharmacia, Brunswick, Germany). Hybridization was carried out overnight at 68° C. after addition of the labeled DNA probe in the same buffer. The wash steps were carried out twice for 15 minutes using 2×SSC and twice for 30 minutes using 1×SSC, 1% SDS, at 68° C. The sealed filters were exposed at −70° C. for a period of 1 to 14 days.

To study the presence or the relative amount of protein translated from this mRNA, standard techniques such as a Western blot may be employed (see, for example, Ausubel et al. (1988) Current Protocols in Molecular Biology, Wiley: N.Y.). In this method, the cellular total proteins are extracted, separated by means of gel electrophoresis, transferred to a matrix like nitrocellulose and incubated with a probe such as an antibody which binds specifically to the desired protein. This probe is usually provided with a chemiluminescent or colorimetric label which can be detected readily. The presence and the amount of the label observed indicates the presence and the amount of the desired mutated protein which is present in the cell.

Example 7

Analysis of the Effect of the Recombinant Proteins on the Production of the Desired Product The effect of genetic modification in plants, fungi, algae, ciliates or on the production of a desired compound (such as a fatty acid) can be determined by growing the modified microorganisms or the modified plant under suitable conditions (as described above) and examining the medium and/or the cellular components for increased production of the desired product (i.e. lipids or a fatty acid). These analytical techniques are known to the skilled worker and comprise spectroscopy, thin-layer chromatography, various staining methods, enzymatic and microbiological methods, and analytical chromatography such as high-performance liquid chromatography (see, for example, Ullmann, Encyclopedia of Industrial Chemistry, vol. A2, pp. 89-90 and pp. 443-613, VCH: Weinheim (1985); Fallon A et al. (1987) "Applications of HPLC in Biochemistry" in: Laboratory Techniques in Biochemistry and Molecular Biology, vol. 17; Rehm et al. (1993) Biotechnology, vol. 3, chapter III: "Product recovery and purification", pp. 469-714, VCH: Weinheim; Belter P A et al. (1988) Bioseparations: downstream processing for Biotechnology, John Wiley and Sons; Kennedy J F und Cabral J M S (1992) Recovery processes for biological Materials, John Wiley and Sons; Shaeiwitz J A and Henry J D (1988) Biochemical Separations, in: Ullmann's Encyclopedia of Industrial Chemistry, vol. B3; chapter 11, p. 1-27, VCH: Weinheim; and Dechow, F. J. (1989) Separation and purification techniques in biotechnology, Noyes Publications).

In addition to the abovementioned methods, plant lipids are extracted from plant material as described by Cahoon et al. (1999) Proc. Natl. Acad. Sci. USA 96 (22):12935-12940, and Browse et al. (1986) Analytic Biochemistry 152:141-145. Qualitative and quantitative lipid or fatty acid analysis is described by Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 pp. (Oily Press Lipid Library; 1); "Progress in Lipid Research, Oxford: Pergamon Press, 1 (1952)-16 (1977) under the title: Progress in the Chemistry of Fats and Other Lipids CODEN.

In addition to measuring the end product of the fermentation, it is also possible to analyze other components of the metabolic pathways which are used for producing the desired compound, such as intermediates and secondary products, in order to determine the overall efficacy of the production of the compound. The analytical methods encompass measurements of the nutrient quantities in the medium (for example sugars, carbohydrates, nitrogen sources, phosphate and other ions), measurements of the biomass compositions and of the growth, analysis of the production of customary metabolites of biosynthetic pathways, and measurements of gases produced during fermentation. Standard methods for these measurements are described in Applied Microbial Physiology; A Practical Approach, P. M. Rhodes and P. F. Stanbury, ed., IRL Press, pp. 103-129; 131-163 and 165-192 (ISBN: 0199635773) and references cited therein.

One example is the analysis of fatty acids (abbreviations: FAME, fatty acid methyl esters; GC-MS, gas-liquid chromatography/mass spectrometry; TAG, triacylglycerol; TLC, thin-layer chromatography).

Unambiguous proof for the presence of fatty acid products can be obtained by analyzing recombinant organisms by analytical standard methods: GC, GC-MS or TLC, as described variously by Christie and the references cited therein (1997, in: Advances on Lipid Methodology, fourth edition: Christie, Oily Press, Dundee, 119-169; 1998, Gaschromatographie-Massenspektrometrie-Verfahren [gas-chromatographic/ mass-spectrometric methods], Lipide 33:343-353).

The material to be analyzed can be disrupted by sonication, milling in the glass mill, liquid nitrogen and milling or other applicable methods. After disruption, the material must be centrifuged. The sediment is resuspended in distilled water, heated for 10 minutes at 100° C., cooled on ice and recentrifuged, followed by extraction in 0.5 M sulfuric acid in methanol with 2% dimethoxypropane for 1 hour at 90° C., which gives hydrolyzed oil and lipid compounds, which give transmethylated lipids. These fatty acid methyl esters are extracted in petroleum ether and finally subjected to GC analysis using a capillary column (Chrompack, WCOT Fused Silica, CP-Wax-52 CB, 25 mm, 0.32 mm) at a temperature gradient of between 170° C. and 240° C. for 20 minutes and for 5 minutes at 240° C. The identity of the fatty acid methyl esters obtained must be defined using standards which are available from commercial sources (i.e. Sigma).

The following protocol was used for the quantitative oil analysis of the *Arabidopsis* plants transformed with the Gpd1 gene:

Lipid extraction from the seeds is carried out by the method of Bligh & Dyer (1959) Can J Biochem Physiol 37:911. To this end, 5 mg of *Arabidopsis* seeds are weighed into 1.2 ml Qiagen microtubes (Qiagen, Hilden) using a Sartorius (Göttingen) microbalance. The seed material is homogenized with 500 µl chloroform/methanol (2:1; contains mono-C17-glycerol from Sigma as internal standard) in an MM300 Retsch mill from Retsch (Haan) and incubated for 20 minutes at RT. The phases were separated after addition of 500 µl 50 mM potassium phosphate buffer pH 7.5. 50 µl are removed from the organic phase, diluted with 1500 µl of chloroform, and 5 µl are applied to Chromarods SIII capillaries from Iatroscan (SKS, Bechenheim). After application of the samples, they are separated in a first step for 15 mins in a thin-layer chamber saturated with 6:2:2 chloroform: methanol: toluene. After the time has elapsed, the capillaries are dried for 4 minutes at room temperature and then placed for 22 minutes into a thin-layer chamber saturated with 7:3 n-hexane:diethyl ether. After a further drying step for 4 minutes at room temperature, the samples are analyzed in an Iatroscan MK-5 (SKS, Bechenheim) following the method of Fraser & Taggart, 1988 J. Chromatogr. 439:404. The following parameters were set for the measurements: slice width 50 msec, threshold 20 mV, noise 30, skim ratio 0. The data were quantified with reference to the internal standard mono-C17-glycerol (Sigma) and a calibration curve established with tri-C17-glycerol (Sigma), using the program ChromStar (SKS, Beichenheim).

T2 seeds of several independent transgenic lines with the constructs pSUN-USP-gpd1 or pGPTV-gpd1 were analyzed to determine the oil contents quantitatively. Three independent extractions were carried out with the seed pools of each line, and the extracts were measured independently. The three independent measurements were used to calculate the mean and the standard deviation.

The result of the measurements for the lines with the construct pGPTV-gpd1 showed a significantly higher oil content in several (10) transgenic lines (FIG. 1) compared to the measurements of 10 wild-type plants. Similar oil contents are measured for the construct pSUN-USP-gpd1 (not shown).

The average oil content of the above lines is 34.86±1.56%, while the average of the wild-type plants is 27.75±2.64%. This corresponds to an absolute increase in the oil content of 7.1% (relative: 25.6%).

To verify the heritability of the gdp1 effect (increased oil content), T2 seeds from the lines with increased oil contents and from lines with unchanged oil contents were planted. In each case 6 plants per line were planted out and the seeds were analyzed for oil content and enzyme activity. The oil content was determined by the methodology described above. The data obtained are shown in FIG. 2. Col-0 and C24 Arabidopsis ecotypes act as controls. C24 is an ecotype which is distinguished by a higher oil content than Col-0. It was possible to characterize lines whose oil contents exceeds that of Col-0. The heritability of the increased oil content as the effect of the expression of the gdp1 genes was thus demonstrated.

Example 8

Determination of glycerol-3-phosphate dehydrogenase Activity

A further aim was the demonstration of the direct effect of the enzyme in the transgenic plants, in addition to the increased oil content. To determine the glycerol-3-phosphate dehydrogenase activity, two *Arabidopsis* seed pods were harvested per plant and extracted by the method of Geigenberger and Stitt ((1993) Planta 189:329-339). To this end, the pods were ground in a mortar under liquid nitrogen and taken up in 200 µl 50 mM HEPES pH 7.4 5 mM 20 $MgCl_2$, 1 mM EDTA, 1 mM EGTA, 5 mM DTT, 0.1% (w/w) of bovine serum albumin, 2 mM benzamidine, 2 mM amino-n-caproic acid, 0.5 mM phenylmethylsulphonyl, 0.1% Triton X-100 and 10% (w/w) glycerol and spun down for 5 minutes, and the supernatant was divided into aliquots. The production of G3P (glycerol-3-phosphate) from the substrates DHAP (dihydroxyacetone phosphate) and NADH was measured to determine the G3PDH activity. To this end, the oxidation of NADH was monitored at 340 nm.

The reaction mixture for the activity determination contained 50 mM HEPES pH 7.4, 4 mM DHAP, 0.2 mM NADH and 10 µl of the extraction mix in final volume of 100 µl. After incubation for 30 minutes at room temperature, the reaction was stopped by heating (20 min, 95° C.). In the control reaction, the reaction was stopped immediately by heating.

Glycerol-3-phosphate "cycling assay": 10 µl of the reaction mixture were added to 45 µl of a solution comprising 200 mM Tricin, $MgCl_{2.5}$ mM (pH 8.5) and heated (20 min, 95° C.) to destroy remaining DHAP. The supernatant was transferred into a 96-well microtiter plate, treated with 45 µl of a mixture comprising 2 units G3Pox, 130 units catalase, 0.4 unit G3PDH and 0.12 µmol NADH. The reaciton was carried out at 30° C. and the resulting absorption monitored at 340 nm in an Anthos htII microplate reader. Reaction rates were calculated on the basis of the decrease in absorption in (mOD*min-1) using the Biolise software (gibon Y et al. (2002) Plant J 30(2):221-235).

The enzyme activity in the transgenic lines #11, #21, #41 and #67 is significantly higher than in control plants (FIG. 3). The plants with increased oil contents correlate with plants with increased enzyme activites. It was thus demonstrated that the increased oil content can be attributed to the increased conversion of DHAP into G3P, the precursor of oil synthesis.

We claim:

1. A method of increasing total oil content in a plant organism or a tissue, organ, part, cell or propagation material thereof, comprising:
    expressing a transgenic yeast glycerol-3-phosphate dehydrogenase in said plant organism or in said tissue, organ, part, cell or propagation material thereof; and
    selecting the plant organism or the tissue, organ, part, cell or propagation material thereof in which the total oil content in said plant organism or in said tissue, organ, part, cell or propagation material thereof is increased in comparison with a corresponding plant organism or a tissue organ, part, cell or propagation material thereof that is not expressing the transgenic yeast glycerol-3-phosphate dehydrogenase.

2. The method of claim 1, wherein the glycerol-3-phosphate dehydrogenase is derived from a yeast selected from the genera consisting of *Cryptacoccus, Torulopsis, Pityrosporum, Brettanomyces, Candida, Kloeckera, Trigonopsis, Trichosporon, Rhodotorul, Sporobolomyces, Bullera, Saccharomyces, Debaromyces, Lipomyces, Hansenula, Endomycopsis, Pichia* and *Hanseniaspora*.

3. The method of claim 1, wherein the glycerol-3-phosphate dehydrogenase is derived from a yeast selected from the species consisting of *Saccharomyces cerevisiae, Pichia pastoris, Hansenula polymorpha, Schizosaccharomyces pombe, Kluyveromyces lactis, Zygosaccharomyces rouxii, Yarrowia lipolitica, Emericella nidulans, Aspergillus nidulans, Debaryomyces hansenii* and *Torulaspora hansenii*.

4. The method of claim 1, wherein the glycerol-3-phosphate dehydrogenase brings about the conversion of dihydroxyacetone phosphate to glycerol-3-phosphate using NADH as cosubstrate and has a peptide sequence encompassing at least one sequence motif selected from the group of sequence motifs consisting of:

```
i)      GSGNWGT(A/T)IAK;           (SEQ ID NO: 22)

ii)     CG(V/A)LSGAN(L/I/V)AXE(V/I)A;  (SEQ ID NO: 26)
and iii)    (L/V)FXRPYFXV.             (SEQ ID NO: 27)
```

5. The method of claim 1, wherein the glycerol-3-phosphate dehydrogenase brings about the conversion of dihydroxyacetone phosphate to glycerol-3-phosphate using NADH as cosubstrate and has a peptide sequence encompassing at least one sequence motif selected from the group of sequence motifs consisting of:

```
iv)     GSGNWGTTIAKV(V/I)AEN;      (SEQ ID NO: 29)

v)      NT(K/R)HQNVKYLP;           (SEQ ID NO: 30)

vi)     D(I/V)LVFN(I/V)PHQFL;      (SEQ ID NO: 31)

vii)    RA(I/V)SCLKGFE;            (SEQ ID NO: 32)

viii)   CGALSGANLA(P/T)EVA;        (SEQ ID NO: 33)

ix)     LFHRPYFHV;                 (SEQ ID NO: 34)
and x)      GLGEII(K/R)FG.             (SEQ ID NO: 35)
```

6. The method of claim 4, wherein the glycerol-3-phosphate dehydrogenase additionally encompasses at least one sequence motif selected from the group of sequence motifs consisting of:

```
                                   (SEQ ID NO: 23)
xi)     H(E/Q)NVKYL;

(SEQ ID NO: 23)
xii)    (D/N)(I/V)(L/I)V(F/W)(V/N)(L/I/V)PHQF(V/L/
        I);

(SEQ ID NO: 25)
xiii)   (A/G)(I/V)SC(L/I)KG;
and (SEQ ID NO: 28)
xiv)    G(L/M)(L/G)E(M/I)(I/Q)(R/K/N)F(G/S/A).
```

7. The method of claim 1, wherein the amino acid sequence of the yeast glycerol-3-phosphate dehydrogenase comprises:
    the sequence of SEQ ID NO: 2, 4, 5, 7, 9, 11, 12, 14, 16, 38 or 40; or
    a functional equivalent of said sequence, which has an amino acid identity of at least 60% to the sequence of SEQ ID NO: 2.

8. The method of claim 1, wherein the plant is an oil crop.

9. The method of claim 1, wherein the total oil content in the seed of a plant is increased.

10. A transgenic expression cassette comprising, a nucleic acid sequence encoding a yeast glycerol-3-phosphate dehydrogenase under the control of a functional promoter, wherein the promoter is a seed-specific promoter.

11. The transgenic expression cassette of claim 10, wherein the nucleic acid sequence comprises:
    the sequence of SEQ ID NO: 1, 3, 6, 8, 10, 13, 15, 37 or 39; or
    a sequence derived from the sequence of SEQ ID NO: 1, 3, 6, 8, 10, 13, 15, 37 or 39 in accordance with degeneracy of the genetic code; or
    a sequence which has at least 60% identity with the sequence of SEQ ID NO: 1.

12. A transgenic vector comprising the expression cassette of claim 10.

13. A transgenic plant organism, tissue, organ, part, cell or propagation material thereof, comprising a recombinant yeast glycerol-3-phosphate dehydrogenase.

14. The transgenic plant organism of claim 13, which is an oil crop selected from the group of the oil crops consisting of *Borago officinalis, Brassica campestris, Brassica napus,*

*Brassica rapa, Cannabis sativa, Carthamus tinctorius, Cocos nucifera, Crambe abyssinica, Cuphea species, Elaeis guinensis, Elaeis oleifera, Glycine max, Gossypium hirsutum, Gossypium barbadense, Gossypium herbaceum, Helianthus annuus, Linum usitatissimum, Oenothera biennis, Olea europaea, Oryza sativa, Ricinus communis, Sesamum indicum, Triticum* species, *Zea mays*, walnut and almond.

15. A method for the production of oils, fats, free fatty acids or derivatives thereof, comprising expressing a transgenic yeast glycerol-3-phosphate dehydrogenase in a plant organism or tissue, organ, part, cell or propagation material thereof.

16. The method of claim 1, wherein the amino acid sequence of the yeast glycerol-3-phosphate dehydrogenase contains one or more sequences selected from the group consisting of: SEQ ID NOS. 22-35.

17. The method of claim 1, wherein the total oil content in said plant organism or in said tissue, organ, part, cell or propagation material thereof, is increased by at least 10%.

18. The method of claim 1, wherein the total oil content in said plant organism or in said tissue, organ, part, cell or propagation material thereof is increased by at least 25%.

19. The transgenic plant organism, tissue, organ, part, cell or propagation material thereof of claim 13, wherein the recombinant yeast glycerol-3-phosphate dehydrogenase is a part of an expression cassette.

20. The transgenic plant organism, tissue, organ, part, cell or propagation material thereof of claim 13, wherein the recombinant yeast glycerol-3-phosphate dehydrogenase is a part of a vector.

21. The transgenic expression cassette of claim 11, wherein the nucleic acid sequence contains at least 80% identity with the sequence of SEQ ID NO: 1.

22. A transgenic expression cassette which contains a seed specific promoter and a nucleic acid sequence which comprises a nucleic acid sequence that encodes:
   the sequence of SEQ ID NO; 2, 4, 5, 7, 9, 11, 12, 14, 16, 38 or 10; or
   an amino acid which has at least 60% identity to the sequence of SEQ ID NO: 2.

23. The transgenic expression cassette of claim 22, wherein the amino acid sequence has at least 80% identity to the sequence of SEQ ID NO: 2.

24. A transgenic expression cassette that contains a seed specific promoter and a nucleic acid sequence which encodes one or more of the amino acid sequences selected from the group consisting of: SEQ ID NOS. 22-35.

25. The transgenic expression cassette of claim 24, wherein the one or more amino acid sequences comprises at least three of the amino acid sequences.

26. The transgenic expression cassette of claim 24, wherein the one or more amino acid sequences comprises at least five of the amino acid sequences.

* * * * *

UNITED STATES PATENT AND TRADEMARK OFFICE
CERTIFICATE OF CORRECTION

PATENT NO. : 7,579,517 B2
APPLICATION NO. : 10/513412
DATED : August 25, 2009
INVENTOR(S) : Andreas Renz et al.

Page 1 of 1

It is certified that error appears in the above-identified patent and that said Letters Patent is hereby corrected as shown below:

In Claim 2, in column 107, on line 28, "*Cryptacoccus*" should read -- *Cryptococcus* --.

In Claim 6, in column 108, on line 27, "SEQ ID NO: 23" should read -- SEQ ID NO: 24 --.

In Claim 22, in column 110, on line 8, "or 10; or" should read -- or 40; or --.

Signed and Sealed this

Twenty-fourth Day of November, 2009

David J. Kappos
*Director of the United States Patent and Trademark Office*

UNITED STATES PATENT AND TRADEMARK OFFICE
CERTIFICATE OF CORRECTION

PATENT NO. : 7,579,517 B2  Page 1 of 1
APPLICATION NO. : 10/513412
DATED : August 25, 2009
INVENTOR(S) : Renz et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1315 days.

Signed and Sealed this

Fourteenth Day of December, 2010

David J. Kappos
*Director of the United States Patent and Trademark Office*